United States Patent
Suzuki

(10) Patent No.: US 8,771,981 B2
(45) Date of Patent: Jul. 8, 2014

(54) METHOD FOR PRODUCING AN L-AMINO ACID

(75) Inventor: Shigeo Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/360,016

(22) Filed: Jan. 27, 2012

(65) Prior Publication Data

US 2012/0202255 A1 Aug. 9, 2012

Related U.S. Application Data

(63) Continuation of application No. PCT/JP2010/062708, filed on Jul. 28, 2010.

(30) Foreign Application Priority Data

Jul. 29, 2009 (JP) ................................. 2009-176518

(51) Int. Cl.
*C12P 21/00* (2006.01)

(52) U.S. Cl.
USPC ........................................ 435/68.1; 435/71.1

(58) Field of Classification Search
USPC .................... 435/71.1, 68.1, 110, 106, 112
See application file for complete search history.

(56) References Cited

U.S. PATENT DOCUMENTS

| | | | |
|---|---|---|---|
| 5,407,957 A | 4/1995 | Kyle et al. | |
| 5,661,012 A | 8/1997 | Sano et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 7,306,933 B2 | 12/2007 | Dien et al. | |
| 7,723,081 B1 | 5/2010 | Nakanishi et al. | |
| 8,193,383 B2 * | 6/2012 | Saft et al. ...................... | 554/167 |
| 2002/0160461 A1 | 10/2002 | Nakai et al. | |
| 2004/0067550 A1 | 4/2004 | Costa Perez et al. | |
| 2004/0197882 A1 | 10/2004 | Saitoh et al. | |
| 2006/0019355 A1 | 1/2006 | Ueda et al. | |
| 2009/0093029 A1 | 4/2009 | Usuda et al. | |
| 2009/0291478 A1 | 11/2009 | Usuda et al. | |
| 2010/0173368 A1 | 7/2010 | Nakanishi et al. | |
| 2011/0014663 A1 | 1/2011 | Suzuki et al. | |
| 2011/0117613 A1 | 5/2011 | Hoshino et al. | |

FOREIGN PATENT DOCUMENTS

| | | |
|---|---|---|
| JP | 2004-504853 | 2/2004 |
| JP | 2005-176851 | 7/2005 |
| JP | 2008-167746 | 7/2008 |
| WO | WO01/04339 | 1/2001 |
| WO | WO01/53459 | 7/2001 |
| WO | WO 2008002053 A1 * | 1/2008 |
| WO | WO2009/011354 | 1/2009 |
| WO | WO2009/093703 | 7/2009 |

OTHER PUBLICATIONS

Chisti, Y., "Biodiesel from microalgae." Biotechnology Advances. vol. 25 (2007) pp. 294-306.*
Department of Health and Human Services, NIOSH Skin Notation Profiles, Sodium Hydroxide, 2011 (retrieved on Sep. 18, 2012). Retrieved from the internet<URL: http://www.cdc.gov/niosh/docs/2011-150/pdfs/2011-150.pdf>.*
Hernawan, T., et al., "Chemical and cytological changes during the autolysis of yeasts," J. Industrial Microbiol. 1995;14:440-450.
Liu, X., et al., "$CO_2$-limitation-inducible Green Recovery of fatty acids from cyanobacterial biomass," PNAS 2011;108(17):6905-6908.
International Preliminary Report on Patentability for PCT Patent App. No. PCT/JP2010/062708 (Feb. 16, 2012).
Chisti, Y., "Biodiesel from microalgae," Biotechnol. Adv. 2007 25:294-306.
International Search Report for PCT Patent App. No. PCT/JP2010/062708 (Oct. 26, 2010).

* cited by examiner

*Primary Examiner* — Jon P Weber
*Assistant Examiner* — Kara Johnson
(74) *Attorney, Agent, or Firm* — Shelly Guest Cermak; Cermak Nakajima LLP

(57) ABSTRACT

A method for producing an L-amino acid by preparing a processed product of a microalgae, which promotes production and accumulation of the L-amino acid by a bacterium having an ability to produce the L-amino acid, by culturing the microalgae in a medium, and processing the resulting culture at a midtemperature; culturing the bacterium in a medium containing the processed product of the microalgae to produce and accumulate the L-amino acid in culture; and collecting the L-amino acid from the culture.

7 Claims, 4 Drawing Sheets

METHOD FOR PRODUCING AN L-AMINO ACID

This application is a Continuation of, and claims priority under 35 U.S.C. §120 to, International Application No. PCT/JP2010/062708, filed Jul. 28, 2010, and claims priority therethrough under 35 U.S.C. §119 to Japanese Patent Application No. 2009-176518, filed Jul. 29, 2009, the entireties of which are incorporated by reference herein. Also, the Sequence Listing filed electronically herewith is hereby incorporated by reference (File name: 2012-01-27; File size: 77 KB; Date recorded: Jan. 27, 2012).

BACKGROUND OF THE INVENTION

1. Field of the Invention

The present invention relates to a method for producing an L-amino acid using a microorganism. L-amino acids are used in various fields such as for use in seasonings, food additives, feed additives, chemicals, and drugs.

2. Brief Description of the Related Art

L-amino acids such as L-threonine and L-lysine are industrially produced by fermentation using amino acid-producing bacteria such as *Escherichia* bacteria. As these amino acid-producing bacteria, bacterial strains isolated from nature, artificial mutants of those bacterial strains, recombinants of those bacterial strains in which L-amino acid biosynthetic enzymes are enhanced by gene recombination, or the like, are used. Examples of the methods for producing L-threonine include, for example, the methods described in Japanese Patent Laid-open (Kokai) No. 5-304969, International Publication WO98/04715, Japanese Patent Laid-open No. 05-227977, and U.S. Patent Published Application No. 2002/0110876. Examples of the methods for producing L-lysine include, for example, the methods described in Japanese Patent Laid-open No. 10-165180, Japanese Patent Laid-open No. 11-192088, Japanese Patent Laid-open No. 2000-253879, and Japanese Patent Laid-open No. 2001-057896.

In the industrial production of L-amino acids by fermentation, saccharides, i.e., glucose, fructose, sucrose, blackstrap molasses, starch hydrolysate, and so forth, are used as carbon sources. Frequently used in methods for producing an L-amino acid by fermentation as a carbon source are saccharification products of starches derived from higher plants such as corn and cassava. These have low moisture content and high starch content, and therefore it is easy to industrially obtain starches from them. On the other hand, although starches contained in microalgae are present at an amount per dry weight unit comparable to that of corn or cassava, the dry weight of the algae per weight unit of culture medium does not reach 1%. The process of separating alga bodies, dehydrating them, disrupting the cells, extracting starches, and purifying the starches is complicated and difficult. Although ethanol fermentation using starches of microalgae is described in U.S. Patent Published Application No. 2006/0135308, U.S. Patent Published Application No. 2007/0202582, and Matsumoto, M. et al., 2003, Appl. Biochem. Biotechnol., 105-108:247-254, the results of the ethanol fermentation are not described. Further, any example of use of saccharified starches of microalgae for amino acid production has not been shown so far.

It is known that *Escherichia coli*, which is a typical amino acid-producing bacterium, can grow using glycerol as a sole carbon source (Lin, E. C. C., 1996, pp. 307-342, In F. D. Neidhardt (ed.), *Escherichia coli* and *Salmonella* Cellular and Molecular Biology/Second Edition, American Society for Microbiology Press, Washington, D.C.), and can grow using long chain fatty acids having 12 or more carbon atoms as the sole carbon source (Clark, D. P. and Cronan Jr., J. E., 1996, pp. 343-357, In F. D. Neidhardt (ed.), *Escherichia coli* and *Salmonella* Cellular and Molecular Biology/Second Edition, American Society for Microbiology Press, Washington, D.C.). Therefore, it is described in Brenner, D. J. and Farmer III J. J. (Family I., 2005, pp. 587-669, In: D. J. Brenner, N. R. Krieg and J. T. Staley, Editors, Bergey's Manual of Systematic Bacteriology, Volume Two: The Proteobacteria Part B: The Gammaproteobacteria, Springer, New York), that *Escherichia coli* can assimilate both long chain fatty acids and glycerol, which are the hydrolysis products of fats and oils, but *Escherichia coli* does not have lipase activity, and therefore it cannot directly assimilate fats and oils. Furthermore, it is also known that solubility of long chain fatty acids is generally extremely low, and the measurement results of the solubility are described in Vorum, H. et al., 1992, Biochimica et Biophysica Acta, 1126:135-142, i.e., although solubility of lauric acid is not lower than 0.1 g/L or more, solubility of oleic acid is not higher than 0.0003 g/L, and that of palmitic acid is not higher than 0.00000003 g/L. Therefore, it is difficult to simultaneously assimilate highly water-soluble glycerol and fatty acids, and there has not been reported to date L-amino acid production based on direct fermentation utilizing hydrolysates of fats and oils, which is a mixture of long chain fatty acids and glycerol, as a carbon source.

As for soybean and *Elaeis guineensis* (oil palm), which are oil plants generally used for production of edible oil, beans or fruits thereof contain about 20% of fats and oils. As for microalgae, there are known microalgae producing fats or oils, and the yield of fats and oils per area much exceeds that obtainable with the oil plants as reported in Chisti Y., 2007, Biotechnol. Adv., 25:294-306. However, the process of separating algae, dehydrating them, disrupting the cells, extracting fats and oils and purifying them is complicated and difficult, as in the case of starches. Therefore, there have so far been no reports about L-amino acid production based on direct fermentation utilizing fats and oils originating in algae.

Further, although methods for extracting organic substances derived from *chlorella* have been reported (Japanese Patent Laid-open No. 9-75094, International Publication WO2006/095964, and U.S. Patent Published Application No. 2007/0202582), it has been considered that disruption is preferably performed by a high temperature reaction. Moreover, there has so far been no report about production of L-amino acids by direct fermentation utilizing a processed product obtained by the aforementioned methods as a carbon source. Furthermore, it has also been known that nucleic acid-related compounds can be increased by autolysis of *chlorella* (Japanese Patent Laid-open No. 62-278977), but there has so far been no report about production of L-amino acids by direct fermentation utilizing a processed product obtained by such a method as mentioned above as a carbon source.

SUMMARY OF THE INVENTION

An aspect of the present invention is to provide a more efficient method for producing an L-amino acid, especially a method for producing an L-amino acid at a lower cost by using a carbon source derived from microalgae as compared with conventional methods for producing an L-amino acid by fermentation using microorganisms, which are performed by using mainly saccharides derived from higher plants as the carbon source.

The present invention demonstrates that L-amino acids can be efficiently produced by utilizing, as a carbon source, a processed product of a culture of a microalga obtained by reacting the culture at a midtemperature, from which organic substances can be obtained without adding lipase or amylase, or with adding a small amount of lipase or amylase. It is an aspect of the present invention to provide a method for producing an L-amino acid, which comprises:

preparing a processed product of a microalga, which promotes production and accumulation of the L-amino acid by a bacterium having an ability to produce the L-amino acid, by culturing the microalga in a first medium, and followed by processing at a midtemperature, culturing the bacterium in a second medium comprising the processed product of the microalga to produce and accumulate the L-amino acid in the second medium, and collecting the L-amino acid from the second medium.

It is a further aspect of the present invention to provide a method as described above, wherein said mid-temperature is 40° C. or higher.

It is a further aspect of the present invention to provide a method as described above, wherein said mid-temperature is 70° C. or lower.

It is a further aspect of the present invention to provide a method as described above, wherein the processed product comprises a) a precipitate obtained by centrifugation of the product of the processing at a mid-temperature, and b) a fatty acid.

It is a further aspect of the present invention to provide a method as described above, wherein the processed product comprises a) a supernatant obtained by centrifugation of the product of the processing at a mid-temperature, and b) glucose or glycerol.

It is a further aspect of the present invention to provide a method as described above, wherein the processed product comprises an extract comprising a fatty acid obtained by subjecting the product of the processing at a mid-temperature to a treatment with an alkali or an organic solvent.

It is a further aspect of the present invention to provide a method as described above, wherein the precipitate obtained by centrifuging the product of the processing at a mid-temperature is subjected to a treatment with an alkali or an organic solvent.

It is a further aspect of the present invention to provide a method as described above, wherein the treatment with an alkali is performed at a pH of 10.5 or higher.

It is a further aspect of the present invention to provide a method as described above, wherein the treatment with an alkali is performed at 60° C. or higher.

It is a further aspect of the present invention to provide a method as described above, wherein organic solvent is selected from the group consisting of methanol, ethanol, 2-propanol, acetone, butanol, pentanol, hexanol, heptanol, octanol, chloroform, methyl acetate, ethyl acetate, dimethyl ether, diethyl ether, and hexane.

It is a further aspect of the present invention to provide a method as described above, wherein temperature is lowered during the processing at a mid-temperature.

It is a further aspect of the present invention to provide a method as described above, wherein the microalga is an alga belonging to the division Chlorophyta or Heterokontophyta.

It is a further aspect of the present invention to provide a method as described above, wherein the microalga is an alga belonging to the class Chlorophyceae, Trebouxiophyceae, or Bacillariophyceae.

It is a further aspect of the present invention to provide a method as described above, wherein the microalga is an alga belonging to the class Chlorophyceae.

It is a further aspect of the present invention to provide a method as described above, wherein the bacterium is a bacterium belonging to the family Enterobacteriaceae or a coryneform bacterium.

It is a further aspect of the present invention to provide a method as described above, wherein the bacterium belonging to the family Enterobacteriaceae is *Escherichia coli*.

By utilizing the present invention, L-amino acids can be efficiently produced.

DESCRIPTION OF THE PREFERRED EMBODIMENTS

Figure 1:
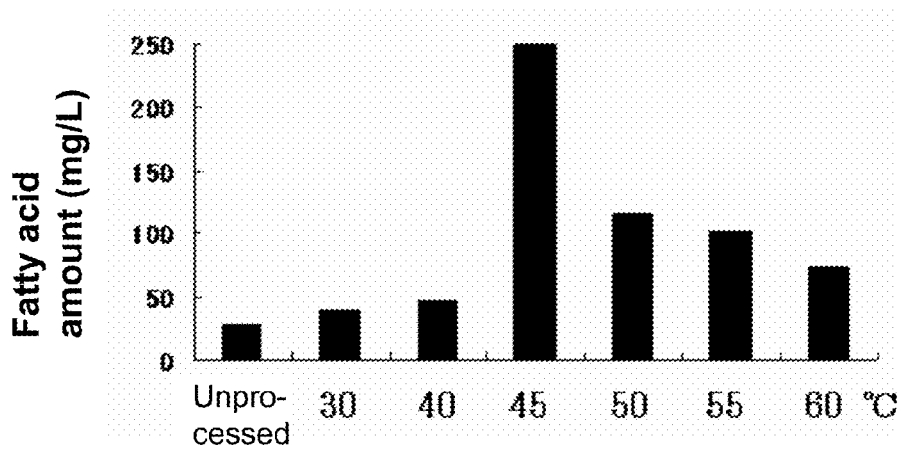
FIG. 1 shows the amount of fatty acids obtained by processing *Chorella kessleri* at a mid-temperature.

Hereafter, the present invention will be explained in detail.

<1> Microalgae and Culture Method Therefore

As the microalga used in the present invention, any algae can be used. However, microalgae which accumulates starches and/or fats and oils in alga bodies are particular examples.

Algae can refer to all the organisms performing oxygen generating type photosynthesis except for Bryophyta, Pteridophyta and Spermatophyta, which live mainly on the ground. Algae can include various unicellular organisms and multicellular organisms such as cyanobacteria (blue-green algae), which are prokaryotes, as well as those classified into the phylum Glaucophyta, Rhodophyta (red algae), Chlorophyta, Cryptophyta (crypt algae), Haptophyta (haptophytes), Heterokontophyta, Dinophyta (dinoflagellates), Euglenophyta, or Chlorarachniophyta, which are eukaryotes. Microalgae can refer to algae having a microscopic structure among these algae except for marine algae, which are multicellular organisms (Biodiversity Series (3) Diversity and Pedigree of Algae, edited by Mitsuo Chihara, Shokabo Publishing Co., Ltd. (1999)).

Many plants, including algae, produce starches as storage polysaccharides (Ball, S. G. and Morell, M. K., 2003, Annual Review of Plant Biology, 54:207-233). Many algae which accumulate starches are known, and typical algae include those of the class Prasinophyceae, Chlorophyceae, Trebouxiophyceae, Ulvophyceae, Charophyceae, or the like, which all belong to the phylum Chlorophyta. Among these, algae belonging to the class Chlorophyceae or Trebouxiophyceae have been well studied. Examples of algae belonging to the class Chlorophyceae include those of the genus *Chlamy-*

*domonas*, and examples of algae belonging to the class Trebouxiophyceae include those of the genus *Chlorella*. Specifically, examples of algae belonging to the genus *Chlamydomonas* include *Chlamydomonas reinhardtii* (Ball, S. G., 1998, The Molecular Biology of Chloroplasts and Mitochondria in *Chlamydomonas*, pp. 549-567, Rochaix J.-D., Goldschmidt-Clermont M., and Merchant S. (Eds), Kluwer Academic Publishers), and examples of algae belonging to the genus *Chlorella* include *Chlorella kessleri* (formerly *Chlorella vulgaris*, Izumo A. et al, 2007, Plant Science, 172:1138-1147). More specifically, examples of *Chlamydomonas reinhardtii* include the *Chlamydomonas reinhardtii* CC125 strain, and examples of *Chlorella kessleri* include the *Chlorella kessleri* 11h strain. These strains are stored at, for example, The University of Texas at Austin, The Culture Collection of Algae (UTEX) (1 University Station A6700, Austin, Tex. 78712-0183, USA) with accession numbers of UTEX 2244 and UTEX 263, respectively, and can be obtained from UTEX. The *Chlorella kessleri* 11h strain was stored at the independent administrative agency, the IAM Culture Collection, Institute of Molecular and Cellular Biosciences, The University of Tokyo with a storage number of C-531, and then transferred to the Microbial Culture Collection at the National Institute for Environmental Studies (NIES). Further, this strain is stored at the American Type Culture Collection (ATCC, P.O. Box 1549, Manassas, Va. 20108, 1, United States of America) under an accession number of ATCC 11468, and can also be obtained from ATCC.

It is further known that microalgae include those that accumulate fats and oils as storage substances (Chisti Y., 2007, Biotechnol. Adv., 25:294-306). As such algae, those belonging to the phylum Chlorophyta or Heterokontophyta are well known. Examples of the algae belonging to the phylum Chlorophyta include those belonging to the class Chlorophyceae, and examples of algae belonging to the class Chlorophyceae include *Neochloris oleoabundans* (Tornabene, T. G. et al., 1983, Enzyme and Microb. Technol., 5:435-440), *Nannochloris* sp. (Takagi, M. et al., 2000, Appl. Microbiol. Biotechnol., 54:112-117) and so forth. In the phylum Heterokontophyta, the classes Chrysophyceae, Dictyochophyceae, Pelagophyceae, Rhaphidophyceae, Bacillariophyceae, Phaeophyceae, Xanthophyceae, and Eustigmatophyceae are classified. Examples of frequently used algae belonging to the class Bacillariophyceae include *Thalassiosira pseudonana* (Tonon, T. et al., 2002, Phytochemistry, 61:15-24). Specific examples of *Neochloris oleoabundans* include the *Neochloris oleoabundans* UTEX 1185 strain, specific examples of *Nannochloris* sp. include the *Nannochloris* sp. UTEX LB 1999 strain, and specific examples of *Thalassiosira pseudonana* include the *Thalassiosira pseudonana* UTEX LB FD2 strain. These strains can be obtained from the University of Texas at Austin, The Culture Collection of Algae (UTEX), 1 University Station A6700, Austin, Tex. 78712-0183, USA.

There is much information about culturing microalgae, and those of the genus *Chlorella* or *Arthrospira* (*Spirulina*), *Dunaliella salina* and so forth are industrially cultured on a large scale (Spolaore, P. et al., 2006, J. Biosci. Bioeng., 101:87-96). For *Chlamydomonas reinhardtii*, for example, the 0.3×HSM medium (Oyama Y. et al., 2006, Planta, 224:646-654) can be used, and for *Chlorella kessleri*, the 0.2× Gamborg's medium (Izumo A. et al., 2007, Plant Science, 172:1138-1147) and so forth can be used. *Neochloris oleoabundans* and *Nannochloris* sp. can be cultured by using the modified NORO medium (Yamaberi, K. et al., 1998, J. Mar. Biotechnol., 6:44-48; Takagi, M. et al., 2000, Appl. Microbiol. Biotechnol., 54:112-117) or the Bold's basal medium (Tornabene, T. G. et al., 1983, Enzyme and Microb. Technol., 5:435-440; Archibald, P. A. and Bold, H. C., 1970, Phytomorphology, 20:383-389). For *Thalassiosira pseudonana* as an alga belonging to the class Bacillariophyceae, the F/2 medium (Lie, C.-P. and Lin, L.-P., 2001, Bot. Bull. Acad. Sin., 42:207-214) and so forth can be used. Further, a photobioreactor can also be used for culturing microalgae (WO2003/094598).

The culture is performed by adding 1 to 50% of precultured cell suspension based on the volume of the main culture in many cases. Initial pH can be around neutral, i.e., 7 to 9, and the pH is not adjusted during the culture in many cases. However, the pH may be adjusted if needed. The culture temperature can be 25 to 35° C., and in particular, a temperature around 28° C. is generally frequently used. However, the culture temperature may be a temperature suitable for the chosen alga. Air is blown into the culture medium in many cases, and as an aeration rate, an aeration volume per unit volume of culture medium per minute of 0.1 to 2 vvm (volume per volume per minute) is frequently used. Further, $CO_2$ may also be blown into the medium in order to promote growth, and it can be blown at about 0.5 to 5% of the aeration rate. Although optimum illumination intensity of light also differs depending on type of microalgae, an illumination intensity of about 1,000 to 10,000 lux is frequently used. As the light source, it is common to use a white fluorescent lamp indoors, but the light source is not limited to it. It is also possible to perform the culture outdoors with sunlight. The culture medium may be stirred at an appropriate intensity, or circulated, if needed. Further, it is known that algae accumulate fats and oils in alga bodies when the nitrogen source is depleted (Thompson G. A. Jr., 1996, Biochim. Biophys. Acta, 1302:17-45), and a medium of a limited nitrogen source concentration can also be used for the main culture.

The culture of microalga can include a culture medium containing alga bodies, and alga bodies which have been collected from a culture medium.

Alga bodies can be collected from a culture medium by typical techniques, such as centrifugation, filtration, gravitational precipitation using a flocculant, or the like (Grima, E. M. et al., 2003, Biotechnol. Advances, 20:491-515).

When fatty acids present in the processed product are used as the carbon source, the microalga can be concentrated by centrifugation or the like before the processing at a mid-temperature. The concentration of the alga bodies includes obtaining a concentration of dry weight of the microalga per unit volume of solution of 25 g/L or higher, or 250 g/L or higher by the removal of solution components (including separating alga bodies from a culture medium by centrifugation or the like and suspending the alga bodies in a liquid at a desired concentration), and using alga bodies precipitated and separated from the medium.

<2> Method for Processing Microalga and Obtaining the Processed Product of Microalga The culture of a microalga can be processed at a mid-temperature, and the processed product of the microalga can be used as a nutrient source for L-amino acid fermentation.

The processed product of microalga can mean a reaction mixture obtained by processing the culture of the microalga at a mid-temperature. Therefore, the terms "to process at a mid-temperature" and "to react at a mid-temperature" have the same meaning. The processed product can include one obtained by further subjecting the reaction mixture processed at a mid-temperature to extraction or fractionation, and/or another treatment, which contains a mixture of organic substances originating in the cells of the microalga, and promotes production and accumulation of an L-amino acid by a bacterium having an ability to produce the L-amino acid.

The expression "to promote production and accumulation of an L-amino acid" means that the mixture of organic substances derived from disrupted cells of microalga contained in the processed product substantially contributes to proliferation of a bacterium and L-amino acid production as a supply source of carbon constituting cell components and L-amino acids. Any processed products which can contribute in such a manner as described above can be included in the "processed product which promotes production and accumulation of an L-amino acid".

Whether a processed product promotes production and accumulation of an L-amino acid can be confirmed by culturing the bacterium under the same conditions in the presence and absence of the processed product, and comparing production and accumulation amounts of the L-amino acid in culture.

Although the L-amino acid accumulation may be improved in any degree as compared with L-amino acid accumulation observed without addition of the processed product, the L-amino acid accumulation can be improved by 10% or more, 20% or more, or even 30% or more, as compared with the culture not containing the processed product.

Improvement of growth rate of a microorganism and increase of cell amount of a microorganism in a culture medium by the addition of the processed product are also included in the results of "to promote production and accumulation of an L-amino acid", and the growth rate and cell amount can be increased by 10% or more, 20% or more, or even 30% or more, as compared with the culture not containing the processed product.

Further, when the processed product contains a carbon source, if it can substantially contribute to growth of a bacterium and L-amino acid production as a supply source of carbon constituting cell components and L-amino acids, it can be included in the processed product which promotes production and accumulation of an L-amino acid. Therefore, although any processed product which increases L-amino acid production and accumulation amounts, as compared with when the processed product is not added, can be a processed product, a processed product which improves L-amino acid production and accumulation amounts as compared with when a carbon source comprising purified substances is added in the same amount as the carbon source contained in the processed product is one particular example.

Further, if the processing steps for purifying the carbon source is shortened as compared with that for using a carbon source consisting of purified substances, it can be said that L-amino acid production and accumulation are improved. In this case, the time of the processing steps can be shortened by 10% or more, 20% or more, or even 30% or more.

The midtemperature can mean a temperature sufficient for increasing the amount of fatty acids, glycerol or glucose in the processed product, and the processing may be continuously performed at the same temperature, or the temperature maybe lowered in the middle of the processing. As an example of lowering the temperature in the middle of the processing, the processing may be performed once at a midtemperature as a first step, and then performed at a constant midtemperature which is lower than the first step temperature as a second step. The continuous processing at a midtemperature, or the first step midtemperature processing, can be performed usually at 40° C. or higher, 45° C. or higher, or even 50° C. or higher, as for the minimum temperature, and usually at 70° C. or lower, 65° C. or lower, or even 60° C. or lower, as for the maximum temperature. The second step can be performed usually at 30° C. or higher, 35° C. or higher, or even 40° C. or higher, as for the minimum temperature, and usually at 55° C. or lower, 50° C. or lower, or even 45° C. or lower, as for the maximum temperature.

Although the culture of the alga obtained by the aforementioned culturing method per se may be subjected to the reaction at a midtemperature, it may be concentrated as described above and then used. For example, the culture may be once centrifuged, and the precipitated alga bodies may be used for the reaction.

Moreover, before the reaction at a midtemperature, the pH for the reaction may be adjusted to be weakly acidic, or the alga bodies may be once frozen.

The weakly acidic pH mentioned above can be 3.0 to 7.0, or 4.0 to 6.0.

The temperature for freezing usually can mean a temperature of from −80 to 0° C., and the reaction can be conducted at −20° C. or lower, or −50° C. or lower, for 1 hour or more.

For the continuous processing at a mid-temperature, the reaction can be performed for at least 1 hour or more, or even 5 hours or more. The reaction at a mid-temperature is usually performed for 48 hours or less, or 24 hours or less. For the first step mid-temperature processing, the reaction can be performed for at least 1 minute or more, 10 minutes or more, or even 20 minutes or more. The first step mid-temperature processing can be performed for 120 minutes or less, or 60 minutes or less. The second step mid-temperature processing can be performed for at least 1 hour or more, 4 hours or more, as for the minimum reaction time, and can be performed for 20 hours or less, or 15 hours or less, as for the maximum reaction time.

When an alkali treatment or organic solvent treatment is performed after the processing at a mid-temperature, the solution processed at a mid-temperature as it is having the same volume may be subjected to the treatment, the solution may be subjected to the treatment after dilution, or a precipitate separated from the supernatant may be subjected to the treatment. The treatment can be performed at a concentration of precipitate per unit volume of the solution of 250 g/L or lower, or 125 g/L or lower. In the case of the alkali treatment, it can be performed at a concentration of 125 g/L or lower, and in the case of the organic solvent treatment, the precipitates can be separated from the supernatant.

The pH for the alkali treatment performed after the processing at a mid-temperature can be 10.5 or higher and 14 or lower, or 11.5 or higher, or even 12.5 or higher.

The temperature of the alkali treatment can be 60° C. or higher, 80° C. or higher, or even 90° C. or higher. The temperature of the alkali treatment can be 120° C. or lower.

The time of the alkali treatment can be at least 10 minutes or more, 30 minutes or more, or even 60 minutes or more. Time of the alkali treatment can be 150 minutes or less.

The processed product obtained by the processing at a mid-temperature may be subjected to the organic solvent treatment for extraction after drying, or may be extracted without drying. Examples of the organic solvent mentioned above include methanol, ethanol, 2-propanol, acetone, butanol, pentanol, hexanol, heptanol, octanol, chloroform, methyl acetate, ethyl acetate, dimethyl ether, diethyl ether, hexane, and so forth.

After the processing at a mid-temperature, the reaction mixture can be separated into precipitate and supernatant by centrifugation. Moreover, after the processing at a mid-temperature, the processed product per se can be used as a medium component for L-amino acid fermentation.

The precipitate can contain much fatty acids, and they can be subjected to an alkali treatment in order to form micelles of the fatty acids in water. Further, in order to obtain more efficient assimilation as the carbon source, the precipitate can be subjected to an emulsification treatment. Examples of the emulsification treatment can include addition of an emulsification enhancer, stirring, homogenization, ultrasonication, and so forth. It is considered that the emulsification treatment makes it easier for the bacteria to assimilate fatty acids, and L-amino acid fermentation becomes more effective. The emulsification treatment can be of any type, so long as it makes it easier for bacteria having an L-amino acid-producing ability to assimilate fatty acids. As the emulsification method, for example, addition of an emulsification enhancer or a surfactant etc. can be contemplated. Examples of emulsification enhancer can include phospholipids and sterols. Examples of the surfactant include, as nonionic surfactants, polyoxyethylene sorbitan fatty acid esters such as poly(oxyethylene) sorbitan monooleic acid ester (Tween 80), alkyl glucosides such as n-octyl β-D-glucoside, sucrose fatty acid esters such as sucrose stearate, polyglyceryl fatty acid esters such as polyglycerin stearic acid ester, and so forth. Examples of the surfactant can include, as ampholytic surfactants, N,N-dimethyl-N-dodecylglycine betaine, which is an alkylbetaine, and so forth. Besides these, surfactants generally used in the field of biology such as Triton X-100, polyoxyethylene (20) cetyl ether (Brij-58) and nonylphenol ethoxlate (Tergitol NP-40) can be used.

Furthermore, an operation for promoting emulsification and homogenization of hardly soluble substances, i.e., fatty acids, is also effective. This operation may be any operation which promotes emulsification and homogenization of a mixture of a fatty acid and glycerol. Specific examples include stirring, homogenizer treatment, homomixer treatment, ultrasonication, high pressure treatment, high temperature treatment, and so forth, and stifling, homogenizer treatment, ultrasonication, and a combinations of these are particular examples.

The treatment can be used with the aforementioned emulsification enhancer and stirring, homogenizer treatment and/or ultrasonication in combination, and these treatments can be carried out under alkaline conditions, under which fatty acids are more stable. As the alkaline condition, pH of 9 or higher can be used, and pH of 11 or higher is another example.

When the precipitate contains fats and oils produced by microalgae, a hydrolysate thereof can also be added to the medium as a carbon source. A mixed solution of organic substances extracted with a solvent such as ethanol, a mixture of methanol and chloroform or acetone can also be subjected to hydrolysis. These solutions can be used as they are, or they can also be concentrated by a processing such as lyophilization and evaporation. This solution contains components that can be used as an organic nitrogen source such as amino acids and components effective for growth of bacteria having an amino acid-producing ability such as metals, and can also be used as a medium component other than the carbon source.

Fats and oils are esters formed from fatty acids and glycerol, and are also called triglycerides. Fats and oils produced by microalgae can be fatty acid species generated by hydrolysis which can be utilized by a chosen bacterium as a carbon source, and higher contents thereof can be used. Examples of long chain fatty acid species assimilable by bacteria having an L-amino acid-producing ability include lauric acid, myristic acid, palmitic acid, stearic acid, oleic acid, and so forth. Further, besides fats and oils, organisms generally contain lipids, which release fatty acids by hydrolysis, and fatty acids produced by hydrolysis of lipids can also be used as a carbon source. Examples of the lipid include waxes and ceramides, which are simple lipids, as well as phospholipids and glycolipids, which are complex lipids, and so forth.

In order to further hydrolyze fats and oils, the precipitate may be reacted with a lipase. Lipases are enzymes that hydrolyze fat or oil into fatty acids and glycerol, and are also called triacylglycerol lipases, or triacylglyceride lipases.

Lipases are found in various organisms, and lipases derived from any species may be used so long as a lipase which catalyzes the aforementioned reaction is used. In recent years, various attempts have also been made to produce biodiesel fuel, which is fatty acid esters, from fat or oil and an alcohol by using a lipase enzyme (Fukuda, H., Kondo, A., and Noda, H., 2001, J. Biosci. Bioeng., 92, 405-416).

As typical lipases derived from microorganisms, many lipases derived from those of the genus *Bacillus, Burkholderia, Pseudomonas* or *Staphylococcus* are known (Jaeger, K. E., and Eggert, T., 2002, Curt Opin. Biotechnol., 13:390-397).

As examples, the nucleotide sequence of the gene coding for LipA derived from *Bacillus subtilis* (GenBank Accession No. M74010) and the amino acid sequence thereof are shown in SEQ ID NOS: 1 and 2, respectively.

The nucleotide sequence of the gene coding for LipA derived from *Burkholderia glumae*(GenBank Accession No. X70354) and the amino acid sequence thereof are shown in SEQ ID NOS: 3 and 4, respectively.

The nucleotide sequence of the gene coding for LipA derived from *Pseudomonas aeruginosa* (GenBank Accession No. D50587) and the amino acid sequence thereof are shown in SEQ ID NOS: 5 and 6, respectively.

The nucleotide sequence of the lipase derived from *Staphylococcus aureus* (GenBank Accession No. M12715) and the amino acid sequence thereof are shown in SEQ ID NOS: 7 and 8, respectively.

The lipase derived from the yeast *Candida antarctica* (GenBank Accession No. Z30645) is also one of the lipases which can be used (Breivik, H., Haraldsson, G. G., and Kristinsson, B., 1997, J. Am. Oil Chem. Soc., 74, 1425-1429). The nucleotide sequence of the gene coding for this lipase and the amino acid sequence thereof are shown in SEQ ID NOS: 9 and 10, respectively.

Furthermore, as for the yeast, of five or more kinds of lipases encoded by separate genes are known to be present in *Candida rugosa* (*Candida cylindracea*) (Alberghina, L. and Lotti, M., 1997, Methods Enzymol., 284:246-260). As major lipases, LIP1 and LIP2 are known, and the nucleotide sequence of the lip1 gene (GenBank Accession No. X64703) coding for LIP1 and the amino acid sequence thereof are shown in SEQ ID NOS: 11 and 12, respectively. The nucleotide sequence of the lip2 gene (GenBank Accession No. X64703) coding for LIP2 and the amino acid sequence thereof are shown in SEQ ID NOS: 13 and 14, respectively. In addition, it is known that, in yeasts of the genus *Candida* such as *Candida cylindracea*, the CTG codon, which codes for leucine according to the universal codes, codes for serine (Kawaguchi, Y. et al., 1989, Nature, 341:164-166; Ohama, T. et al., 1993, Nucleic Acids Res., 21:4039-4045). In SEQ ID NOS: 11 to 14, although the amino acids corresponding to CTG are indicated as Leu for convenience, they are actually Ser.

Furthermore, lipases derived from *Cryptococcus* bacteria, for example, the lipase produced by *Cryptococcus* sp. S-2, and lipases having a primary structure similar to those of the foregoing lipases may also be used (Japanese Patent Laid-open No. 2004-73123). As a gene coding for a lipase derived from a *Cryptococcus* bacterium, the lipase gene CS2 of *Cryptococcus* sp. S-2 (FERM P-15155) is known (Japanese Patent Laid-open No. 2004-73123). The nucleotide sequence of this CS2 gene is shown in SEQ ID NO: 18, and the amino acid sequence of the precursor of the lipase encoded by this CS2 gene is shown in SEQ ID NO: 19. It is expected that, in the amino acid sequence of SEQ ID NO: 2, the sequence of the −34 to −1 positions is a signal peptide, and the sequence of the 1 to 205 positions corresponds to the mature protein. *Cryptococcus* sp. S-2 was deposited on Sep. 5, 1995 at the National Institute of Bioscience and Human-Technology, Agency of Industrial Science and Technology (presently, the independent administrative agency, the International Patent Organism Depository, National Institute of Advanced Industrial Science and Technology (Central 6, 1-1, Higashi 1-Chome, Tsukuba-shi, Ibaraki-ken, 305-8566, Japan)), and assigned an accession number of FERM P-15155. The deposit was converted to an international deposit based on the Budapest Treaty on Apr. 25, 2008, and assigned an accession number of FERM BP-10961.

As the aforementioned lipases, those prepared from cells or culture of the aforementioned microorganisms can be used, or they may be prepared by expressing a gene coding for each lipase in another host microorganism using genetic engineering techniques. When a gene derived from yeast in which CTG codon codes for serine, such as *Candida rugosa*(*Candida cylindracea*), is expressed in another host, it is necessary to change CTG into another universal codon coding for serine (Schmidt-Dannert, C., 1999, Bioorg. Med. Chem., 7:2123-2130).

Examples of the characteristics of sequences of lipases include the presence of the GXSXG motif called a lipase box near Ser of the active center, and conservation of three residues of Ser, Asp and His called the catalytic triad, which are common to lipases, esterases and serine proteases. For example, in the amino acid sequence of LipA derived from *Bacillus subtilis* shown in SEQ ID NO: 2, the lipase box corresponds to the positions 106 to 110, and the catalytic triad corresponds to the three residues: Ser at the position 108, Asp at the position 164, and His at the position 187.

Furthermore, in order to reduce the cost for the enzyme, a lipase modified so that the activity and stability thereof are improved may also be used. Examples include the lipase A of *Bacillus subtilis* modified by the phage display method (Droge et al., ChemBioChem, 2006, 7:149-157), a modified lipase of which activity and stability are improved by DNA shuffling (Suen et al., Protein Eng. Design & Selection, 2004, 17:133-140), the *C. antactica* lipase B modified by the CALB method (Zhang et al., Protein Eng., 2003, 16:599-605), the *Pseudomonas aeruginosa* lipase modified by the CAST method (Reets et al., Angew. Chem. Int. Ed., 2005, 44:4192-4196), and so forth.

If fats and oils in the precipitate obtained by centrifugation of the processed product obtained by the reaction at a midtemperature are decomposed, they decompose into fatty acids and glycerol. Therefore, glycerol may be used as a carbon source for the amino acid fermentation.

The supernatant obtained by centrifugation of the processed product obtained by the reaction at a midtemperature may also be used as the processed product. The supernatant obtained by centrifugation of the processed product contains fragments of starches and glucose as well as glycerol, which are produced through decomposition of starches and oils and fats, respectively, by the processing at a mid-temperature according to the present invention. Therefore, glucose and glycerol may be used as the carbon source.

The supernatant obtained by centrifugation of the processed product obtained the reaction at a moderate temperature contains fragments of starches. Therefore, a processed product obtained by saccharifying the fragments of starches in the supernatant with an amyloglucosidase or the like to further increase the glucose amount may also be used.

Starches are high molecular weight polysaccharides made up of amylose, which includes glucose residues linearly linked by α-1,4-glycoside linkages and amylopectin, which includes glucose residues linearly linked by α-1,4-glycoside linkages and branching by α-1,6-glycoside linkages. Amylase is a generic name for enzymes that hydrolyze glycoside linkages of starches etc. Because of a difference in the action site, they are roughly classified into α-amylase (EC 3.2.1.1), β-amylase (EC 3.2.1.2), and glucoamylase (EC 3.2.1.3) or amyloglucosidase (amylo-alpha-1,6-glucosidase, EC: HYPERLINK www.genome.jp/dbget-bin/www#bget?3.2.1.33" 3.2.1.33. α-Amylase is an endo-type enzyme which randomly cleaves α-1,4-glycoside linkages of starches, glycogen, and so forth. β-Amylase is an exo-type enzyme which cleaves α-1,4-glycoside linkage to excise a maltose unit one by one from the non-reducing end of starches. The glucoamylase or amyloglucosidase is an exo-type enzyme which cleaves α-1,4-glycoside linkages to excise a glucose unit one by one from the non-reducing end of starches, and also cleaves α-1,6-glycoside linkages contained in amylopectin. In order to directly produce glucose from starches, glucoamylase or amyloglucosidase is widely used for the production of glucose.

There are many examples of saccharification reactions of starches derived from grains, which can also be industrially implemented (Robertson, G. H. et al., 2006, J. Agric. Food Chem., 54:353-365). In the same manner as these examples, a saccharification product can be obtained from alga bodies by an enzymatic reaction. When a solution containing disrupted alga bodies is subjected to an enzyme treatment, a pretreatment such as boiling, ultrasonication, an alkaline treatment, and so forth can be used in combination (Izumo A. et al., 2007, Plant Science, 172:1138-1147).

Conditions of the enzymatic reaction can be suitably determined according to the characteristics of the chosen enzyme. For example, for amyloglucosidase (Sigma Aldrich, A-9228), an enzyme concentration of 2 to 20 U/mL, a temperature of 40 to 60° C., and pH 4 to 6 are particular examples. If an organic acid that can be assimilated by a bacterium used for the L-amino acid production is used for adjusting pH as a buffer, the organic acid can be used as a carbon source together with the saccharification product of starches. For example, the enzyme reaction product as it is can be added to the medium.

<4> Bacteria Used in the Present Inventions

A bacterium having an L-amino acid-producing ability is used. The bacterium is not particularly limited, so long as it can efficiently produce an L-amino acid from organic substances produced by microalgae, in particular, a saccharification product of starches or a hydrolysate of fat or oil. Examples of the bacterium include, for example, bacteria belonging to the family Enterobacteriaceae such as those of the genus *Escherichia, Pantoea, Enterobacter*, and so forth, and so-called coryneform bacteria such as those belonging to the genus *Brevibacterium, Corynebacterium, Microbacterium*, or the like, but the bacterium is not limited to these.

The L-amino acid-producing bacterium can be modified to increase an ability to utilize hydrolysate of fats or oils or fatty acids. Examples of such modification include, for example, deletion of the gene coding for the transcription factor FadR having a DNA-binding ability for controlling the fatty acid metabolism observed in enterobacteria (DiRusso, C. C. et al., 1992, J. Biol. Chem., 267:8685-8691; DiRusso, C. C. et al., 1993, Mol. Microbiol., 7:311-322). Specifically, the fadR gene of *Escherichia coli* is a gene located at the nucleotide numbers 1,234,161 to 1,234,880 of the genome sequence of

*Escherichia coli* MG1655 strain registered with Genbank Accession No. U00096, and coding for the protein registered with GenBank accession No. AAC74271. The fadR gene sequence of *Escherichia coli* is shown in SEQ ID NO: 16.

In order to enhance the ability to assimilate hydrolysates of fats and oils or fatty acids, expression amounts of one or more of genes selected from fadA, fadB, fadI, fadJ, fadL, fadE and fadD can be increased.

The "fadL gene" can mean a gene encoding a transporter of the outer membrane having an ability to take up a long chain fatty acid, which is found in the Enterobacteriaceae family bacteria (Kumar, G. B. and Black, P. N., 1993, J. Biol. Chem., 268:15469-15476; Stenberg, F. et al., 2005, J. Biol. Chem., 280:34409-34419). Specific examples of gene encoding FadL include the gene located at the nucleotide numbers 2459322 to 2460668 of the *Escherichia coli* genomic sequence (Genbank Accession No. U00096) as the fadL gene of *Escherichia coli*.

The "fadD gene" can mean a gene coding for an enzyme having the fatty acyl-CoA synthetase activity, which generates fatty acyl-CoA from a long chain fatty acid and facilitates uptake through the inner membrane, which is found in the Enterobacteriaceae family bacteria (Dirusso, C. C. and Black, P. N., 2004, J. Biol. Chem., 279:49563-49566; Schmelter, T. et al., 2004, J. Biol. Chem., 279: 24163-24170). Specific examples of the gene encoding FadD include the gene located at the nucleotide numbers 1887770 to 1886085 (complementary strand) of *Escherichia coli* genomic sequence (GenBank Accession No. U00096) as the fadD gene of *Escherichia coli*.

The "fadE gene" can mean a gene encoding an enzyme having the acyl-CoA dehydrogenase activity, which oxidizes fatty acyl-CoA, and is found in the Enterobacteriaceae family bacteria (O'Brien, W. J. and Frerman, F. E. 1977, J. Bacteriol., 132:532-540; Campbell, J. W. and Cronan, J. E., 2002, J. Bacteriol., 184:3759-3764).

Specific examples of the gene coding for FadE include the gene located at the nucleotide numbers 243303 to 240859 (complementary strand) of *Escherichia coli* genomic sequence (GenBank Accession No. U00096) and having the nucleotide sequence shown in SEQ ID NO: 7 as the fadE gene of *Escherichia coli*. The amino acid sequence encoded by this gene is shown in SEQ ID NO: 8.

The "fadB gene" can mean a gene coding for an enzyme which is the α component of a fatty acid oxidation complex found in the Enterobacteriaceae family bacteria and has four different activities, that is, of enoyl-CoA hydratase, 3-hydroxyacyl-CoA dehydrogenase, 3-hydroxyacyl-CoA epimerase and Δ3-cis-Δ2-trans-enoyl-CoA isomerase (Pramanik, A. et al., 1979, J. Bacteriol., 137:469-473; Yang, S. Y. and Schulz, H., 1983, J. Biol. Chem., 258:9780-9785). Specific examples of the gene coding for FadB include the gene located at the nucleotide numbers 4028994 to 4026805 (complementary strand) of *Escherichia coli* genomic sequence (GenBank Accession No. U00096) as the fadB gene of *Escherichia coli*.

The "fadA gene" referred to in the present invention means a gene coding for an enzyme which is the β component of the fatty acid oxidation complex found in the Enterobacteriaceae family bacteria and shows the 3-ketoacyl-CoA thiolase activity (Pramanik, A. et al., 1979, J. Bacteriol., 137: 469-473). Specific examples of the gene coding for FadA include the gene located at the nucleotide numbers 4026795 to 4025632 (complementary strand) of the *Escherichia coli* genomic sequence (GenBank Accession No. U00096) as the fadA gene of *Escherichia coli*.

It is known that FadB and FadA form a complex in the fatty acid oxidation complex found in the Enterobacteriaceae family bacteria, and the genes also form the fadBA operon (Yang, S. Y. et al., 1990, J. Biol. Chem., 265:10424-10429). Therefore, as the fadBA operon, the whole operon can also be amplified.

The ability to assimilate hydrolysates of fats and oils or fatty acids can also be enhanced by enhancing the cyo operon (cyoABCDE). The "cyoABCDE" can mean a group of genes coding for the subunits of the cytochrome bo terminal oxidase complex as one of the terminal oxidases found in the Enterobacteriaceae family bacteria. The cyoB is a gene coding for the subunit I, cyoA is a gene encoding the subunit II, cyoC is a gene encoding the subunit III, cyoC is a gene encoding the subunit IV, and cyoE is a gene encoding an enzyme showing the heme O synthase activity (Gennis, R. B. and Stewart, V., 1996, pp. 217-261, In F. D. Neidhardt (ed.), *Escherichia coli* and *Salmonella* Cellular and Molecular Biology/Second Edition, American Society for Microbiology Press, Washington, D.C; Chepuri et al., 1990, J. Biol. Chem., 265:11185-11192).

Specific examples of the gene coding for cyoA include the gene located at the nucleotide numbers 450834 to 449887 (complementary strand) of the *Escherichia coli* genomic sequence (GenBank Accession No. U00096) as the cyoA gene of *Escherichia coli*. Specific examples of gene coding for cyoB include the gene located at the nucleotide numbers 449865 to 447874 (complementary strand) of *Escherichia coli* genomic sequence (GenBank Accession No. U00096) as the cyoB gene of *Escherichia coli*. Specific examples of gene coding for cyoC include the gene located at the nucleotide numbers 447884 to 447270 (complementary strand) of the *Escherichia coli* genomic sequence (GenBank Accession No. U00096) as the cyoC gene of *Escherichia coli*. Specific examples of gene coding for cyoD include the gene located at the nucleotide numbers 447270 to 446941 (complementary strand) of the *Escherichia coli* genomic sequence (GenBank Accession No. U00096) as cyoD gene of *Escherichia coli*. Specific examples of gene coding for cyoE include the gene located at the nucleotide numbers 446929 to 446039 (complementary strand) of the *Escherichia coli* genomic sequence (GenBank Accession No. U00096) as the cyoE gene of *Escherichia coli*.

The bacterium can be modified so that the activity of pyruvate synthase or pyruvate:NADP$^+$ oxidoreductase is enhanced (refer to WO2009/031565).

The "pyruvate synthase" can mean an enzyme which can reversibly catalyze the following reaction, which generates pyruvic acid from acetyl-CoA and $CO_2$ in the presence of an electron donor such as ferredoxin and flavodoxin (EC 1.2.7.1). Pyruvate synthase may be abbreviated as PS, and may be designated pyruvate oxidoreductase, pyruvate ferredoxin oxidoreductase, pyruvate flavodoxin oxidoreductase, or pyruvate oxidoreductase. As the electron donor, ferredoxin or flavodoxin can be used.

Reduced ferredoxin+acetyl-CoA+$CO_2$->oxidized ferredoxin+pyruvic acid+CoA

Enhancement of the pyruvate synthase activity can be confirmed by preparing crude enzyme solutions from the microorganism before and after the enhancement, and comparing the pyruvate synthase activities. The activity of pyruvate synthase can be measured by, for example, the method of Yoon et al. (Yoon, K. S. et al., 1997, Arch. Microbiol. 167:275-279). For example, the measurement can be taken by adding pyruvic acid to a reaction mixture containing oxidized methylviologen as an electron acceptor, CoA, and a crude enzyme solution, and spectroscopically measuring the amount of reduced methylviologen, which increases due to the decarboxylation of pyruvic acid. One unit (U) of the enzymatic activity is defined as the activity of reducing 1 μmol of methylviologen per 1 minute. When the parent strain has the pyruvate synthase activity, the activity desirably increases, for example, 1.5 times or more, 2 times or more, or even 3 times or more, compared with that of the parent strain. When the parent strain does not have the pyruvate synthase activity, although it is sufficient that pyruvate synthase is produced by the introduction of the pyruvate synthase gene, the activity can be enhanced to such an extent that the enzymatic activity can be measured, and the activity can be 0.001 U/mg (cell protein) or higher, 0.005 U/mg or higher, or even 0.01 U/mg or higher. Pyruvate synthase is sensitive to oxygen, and activity expression and measurement are generally often difficult (Buckel, W. and Golding, B. T., 2006, Ann. Rev. of Microbiol., 60:27-49). Therefore, when the enzymatic activity is measured, the enzymatic reaction can be performed by reducing oxygen concentration in a reaction vessel.

As the gene encoding the pyruvate synthase, pyruvate synthase genes from bacteria having the reductive TCA cycle, such as the pyruvate synthase genes of *Chlorobium tepidum* and *Hydrogenobacter thermophilus*, can be used. Moreover, pyruvate synthase genes from bacteria belonging to the Eenterobacteriaceae family bacteria, including *Escherichia coli*, can be used. Furthermore, as the gene coding for pyruvate synthase, pyruvate synthase genes of autotrophic methanogens such as *Methanococcus maripaludis*, *Methanocaldococcus jannaschii*, and *Methanothermobacter thermautotrophicus*, can be used.

The "pyruvate:NADP$^+$ oxidoreductase" can mean an enzyme reversibly catalyzing the following reaction, which generates pyruvic acid from acetyl CoA and $CO_2$, in the presence of an electron donor such as NADPH or NADH (EC 1.2.1.15). The pyruvate:NADP$^+$ oxidoreductase may be abbreviated as PNO, and may also be called pyruvate dehydrogenase. However, the "pyruvate dehydrogenase activity" is the activity of catalyzing the oxidative decarboxylation of pyruvic acid to generate acetyl-CoA, as described later, and pyruvate dehydrogenase (PDH) which catalyzes this reaction is an enzyme different from pyruvate:NADP$^+$ oxidoreductase. Pyruvate:NADP$^+$ oxidoreductase can use NADPH or NADH as the electron donor.

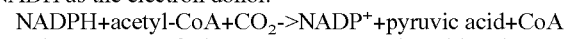
NADPH+acetyl-CoA+$CO_2$->NADP$^+$+pyruvic acid+CoA

Enhancement of the pyruvate:NADP$^+$ oxidoreductase activity can be confirmed by preparing crude enzyme solutions from the microorganism before and after the enhancement, and comparing the pyruvate:NADP$^+$ oxidoreductase activities. The activity of pyruvate:NADP$^+$ oxidoreductase can be measured by, for example, the method of Inui et al. (Inui, H., et al., 1987, J. Biol. Chem., 262:9130-9135). For example, the measurement can be attained by adding pyruvic acid to a reaction mixture containing oxidized methylviologen as an electron acceptor, CoA, and a crude enzyme solution, and spectroscopically measuring the amount of reduced methylviologen, which increases due to the decarboxylation of pyruvic acid. One unit (U) of the enzymatic activity is defined as an activity of reducing 1 μmol of methylviologen per 1 minute. When the parent strain has the pyruvate:NADP$^+$ oxidoreductase activity, the activity increases 1.5 times or more, 2 times or more, or even 3 times or more, compared with that of the parent strain. When the parent strain does not have the pyruvate:NADP$^+$ oxidoreductase activity, although it is sufficient that pyruvate:NADP$^+$ oxidoreductase is produced by the introduction of the pyruvate:NADP$^+$ oxidoreductase gene, the activity can be enhanced to such an extent that the enzymatic activity can be measured, and the activity can be 0.001 U/mg (cell protein) or higher, 0.005 U/mg or higher, or even 0.01 U/mg or higher. Pyruvate:NADP$^+$ oxidoreductase is sensitive to oxygen, and activity expression and measurement are generally often difficult (Inui, H., et al, 1987, J. Biol. Chem., 262: 9130-9135; Rotte, C. et al., 2001, Mol. Biol. Evol., 18:710-720).

As for the gene coding for pyruvate:NADP$^+$ oxidoreductase, it is known that, besides the pyruvate:NADP$^+$ oxidoreductase gene of *Euglena gracilis*, which is a photosynthetic eukaryotic microorganism and is also classified into protozoans (Nakazawa, M. et al., 2000, FEBS Lett., 479:155-156), and the pyruvate:NADP$^+$ oxidoreductase gene of a protist, *Cryptosporidium parvum* (Rotte, C. et al., 2001, Mol. Biol. Evol., 18:710-720), a homologous gene also exists in Bacillariophyta, *Tharassiosira pseudonana* (Ctrnacta, V. et al., 2006, J. Eukaryot. Microbiol., 53:225-231).

Specifically, the pyruvate:NADP$^+$ oxidoreductase gene of *Euglena gracilis* can be used (GenBank Accession No. AB021127).

The microorganism can be modified so that the pyruvate synthase activity is increased so that the activity for recycling oxidized electron donor to reduced electron donor, which is required for the pyruvate synthase activity, increases compared with a parent strain, for example, a wild-type strain or a non-modified strain. Examples of the activity for recycling oxidized electron donor to reduced electron donor include ferredoxin NADP$^+$ reductase activity. Further, the microorganism may be modified so that the activity of pyruvate synthase is increased so that pyruvate synthase activity increases, in addition to the enhancement of the electron donor recycling activity. The aforementioned parent strain can inherently have a gene coding for the electron donor recycling activity, or can be a strain which does not inherently have the electron donor recycling activity, but this activity can be imparted by introduction of a gene coding for the activity, so that the L-amino acid-producing ability is improved.

The "ferredoxin NADP$^+$ reductase" can mean an enzyme that reversibly catalyzes the following reaction (EC 1.18.1.2).

Reduced ferredoxin+NADP$^+$->Oxidized ferredoxin+NADPH+H$^+$

This reaction is a reversible reaction, and can generate the reduced ferredoxin in the presence of NADPH and the oxidized ferredoxin. Ferredoxin can be replaced with flavodoxin, and the enzyme flavodoxin NADP$^+$ reductase also has an equivalent function. The existence of ferredoxin NADP$^+$ reductase has been confirmed in a wide variety of organisms ranging from microorganisms to higher organisms (refer to Carrillo, N. and Ceccarelli, E. A., 2003, Eur. J. Biochem., 270:1900-1915; Ceccarelli, E. A. et al., 2004, Biochim. Biophys. Acta., 1698:155-165), and some of the enzymes are also named ferredoxin NADP$^+$ oxidoreductase or NADPH-ferredoxin oxidoreductase.

Enhancement of the ferredoxin NADP$^+$ reductase activity can be confirmed by preparing crude enzyme solutions from the microorganism before and after the modification, and comparing the ferredoxin NADP$^+$ reductase activities. The activity of ferredoxin NADP$^+$ reductase can be measured by, for example, the method of Blaschkowski et al. (Blaschkowski, H. P. et al., 1982, Eur. J. Biochem., 123:563-569). For example, the activity can be measured by using ferredoxin as a substrate to spectroscopically measure the decrease of the amount of NADPH. One unit (U) of the enzymatic activity is defined as the activity for oxidizing 1 μmol of NADPH per 1 minute. When the parent strain has the ferredoxin NADP$^+$ reductase activity, and the activity of the parent strain is sufficiently high, it is not necessary to enhance the activity. However, the enzymatic activity can be increased 1.5 times or more, 2 times or more, or even 3 times or more, compared with that of the parent strain.

Genes encoding the ferredoxin NADP$^+$ reductase are found in many biological species, and any which have the activity in the objective L-amino acid-producing strain can be used. As for *Escherichia coli*, the fpr gene has been identified as the gene which enocodes flavodoxin NADP$^+$ reductase (Bianchi, V. et al., 1993, 175:1590-1595). Moreover, it is known that, in *Pseudomonas putida*, an NADPH-putidaredoxin reductase gene and a putidaredoxin gene exist as an operon (Koga, H. et al., 1989, J. Biochem. (Tokyo), 106:831-836).

Examples of the flavodoxin NADP$^+$ reductase gene of *Escherichia coli* include the fpr gene which is located at the nucleotide numbers 4111749 to 4112495 (complementary strand) of the genomic sequence of the *Escherichia coli* K-12 strain (Genbank Accession No. U00096). Moreover, a ferredoxin NADP+ reductase gene (Genbank Accession No. BAB99777) is also found at the nucleotide numbers 2526234 to 2527211 of the genomic sequence of *Corynebacterium glutamicum* (Genbank Accession No. BA00036).

The pyruvate synthase activity requires the presence of ferredoxin or flavodoxin as an electron donor. Therefore, the microorganism can be modified so that the activity of pyruvate synthase is increased so that the production ability for ferredoxin or flavodoxin is improved.

Moreover, the microorganism may also be modified so that the production ability for ferredoxin or flavodoxin is improved, in addition to being modified so that pyruvate synthase activity or flavodoxin NADP$^+$ reductase and pyruvate synthase activities are enhanced.

The "ferredoxin" can refer to a protein containing non-heme iron atoms (Fe) and sulfur atoms, bound with an iron-sulfur cluster called 4Fe-4S, 3Fe-4S or 2Fe-2S cluster, and functioning as a one-electron carrier. The "flavodoxin" can refer to a protein containing FMN (flavin-mononucleotide) as a prosthetic group and functioning as a one- or two-electron carrier. Ferredoxin and flavodoxin are described in the reference of McLean et al. (McLean K. J. et al., 2005, Biochem. Soc. Trans., 33:796-801).

The parent strains to be subjected to the modification may be strains which inherently have an endogenous gene encoding ferredoxin or flavodoxin. Alternatively, the parent strains may be strains which do not inherently have a gene encoding ferredoxin or flavodoxin, but which can be imparted with the activity by introduction of a ferredoxin or flavodoxin gene to show improved L-glutamic acid-producing ability.

Improvement of ferredoxin or flavodoxin-producing ability compared with the parent strain such as a wild-type or non-modified strain can be confirmed by, for example, SDS-PAGE, two-dimensional electrophoresis, or Western blotting using antibodies (Sambrook, J. et al., 1989, Molecular Cloning A Laboratory Manual/Second Edition, Cold Spring Harbor Laboratory Press, New York). Degree of the increase of the production amount is not particularly limited so long as it increases compared with that of a wild-type strain or non-modified strain. However, it can be increased, for example, 1.5 times or more, 2 times or more, or 3 times or more, compared with that of a wild-type strain or non-modified strain.

The activities of ferredoxin and flavodoxin can be measured by adding them to an appropriate oxidation-reduction reaction system. For example, a method that includes reducing produced ferredoxin with ferredoxin NADP$^+$ reductase and quantifying reduction of cytochrome C by the produced reduced ferredoxin is disclosed by Boyer et al. (Boyer, M. E. et al., 2006, Biotechnol. Bioeng., 94:128-138). Furthermore, the activity of flavodoxin can be measured by the same method using flavodoxin NADP$^+$ reductase.

Genes encoding ferredoxin or flavodoxin are widely distributed, and any of those can be used so long as ferredoxin or flavodoxin encoded by the genes can be utilized by pyruvate synthase and an electron donor recycling system. For example, in *Escherichia coli*, the fdx gene encodes ferredoxin which has a 2Fe-2S cluster (Ta, D. T. and Vickery, L. E., 1992, J. Biol. Chem., 267:11120-11125), and the yfhL gene encodes ferredoxin which has a 4Fe-4S cluster. Furthermore, as the flavodoxin gene, the fldA gene (Osborne C. et al., 1991, J. Bacteriol., 173:1729-1737) and the fldB gene (Gaudu, P. and Weiss, B., 2000, J. Bacteriol., 182:1788-1793) are known. In the genomic sequence of *Corynebacterium glutamicum* (Genbank Accession No. BA00036), multiple ferredoxin genes exist. For example, the fdx gene (Genbank Accession No. BAB97942) is located at the nucleotide numbers of 562643 to 562963, and the fer gene is located at the nucleotide numbers of 1148953 to 1149270 (Genbank Accession No. BAB98495). Furthermore, in *Chlorobium tepidum*, many ferredoxin genes exist, and ferredoxin I and ferredoxin II have been identified and are of the 4Fe-4S type, which serves as the electron acceptor of pyruvate synthase (Yoon, K. S. et al., 2001, J. Biol. Chem., 276:44027-44036). Ferredoxin or flavodoxin genes of bacteria having the reductive TCA cycle such as *Hydrogenobacter thermophilus* can also be used.

Specific examples of the ferredoxin gene of *Escherichia coli* include the fdx gene located at the nucleotide numbers of 2654770 to 2655105 (complementary strand) of the genomic sequence of the *Escherichia coli* K-12 strain (Genbank Accession No. U00096), and the yfhL gene located at the nucleotide numbers of 2697685 to 2697945 of the same.

In the L-amino acid-producing bacterium, one or more genes involved in glycerol metabolism may be modified.

As for genes involved in the glycerol metabolism, in order to enhance glycerol assimilability, expression of the glpR gene (EP 1715056) may be attenuated, or expression of the glycerol metabolism genes (EP 1715055 A) such as glpA, glpB, glpC, glpD, glpE, glpF, glpG, glpK, glpQ, glpT, glpX, tpiA, gldA, dhaK, dhaL, dhaM, dhaR, fsa, and talC may be enhanced.

In particular, in order to enhance glycerol assimilability, the expression of the glycerol dehydrogenase gene (gldA), and the PEP-dependent dihydroxyacetone kinase gene (dhaKLM) or the ATP-dependent dihydroxyacetone kinase gene (dak) can be enhanced in combination. Furthermore, expression of fructose-6-phosphate aldolase (fsaB) may be enhanced (WO2008/102861).

Further, as for glycerol kinase (glpK), a desensitized glpK gene which is desensitized to the feedback inhibition by fructose-1,6-phosphate (WO2008/081959, WO2008/107277) can be used The family Enterobacteriaceae includes bacteria belonging to the genera *Escherichia, Enterobacter, Erwinia, Klebsiella, Pantoea, Photorhabdus, Providencia, Salmonella, Serratia, Shigella, Morganella, Yersinia*, and the like. In particular, bacteria classified into the family Enterobacteriaceae according to the taxonomy used by the NCBI (National Center for Biotechnology Information) database (www.ncbi.nlm-.nih.gov/Taxonomy/Browser/wwwtax.cgi?id=91347) can be used.

The bacterium belonging to the genus *Escherichia* is not particularly limited. However, examples include, the bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include the

*Escherichia coli* W3110 (ATCC 27325), *Escherichia coli* MG1655 (ATCC 47076) and the like derived from the prototype wild-type strain, K12 strain.

These strains are available from, for example, the American Type Culture Collection (Address: P.O. Box 1549, Manassas, Va. 20108, United States of America). That is, registration numbers are given to each of the strains, and the strains can be ordered by using these numbers. The registration numbers of the strains are listed in the catalogue of the American Type Culture Collection. The same shall apply to the strains listed below with ATCC numbers.

A bacterium belonging to the genus *Pantoea* means that the bacterium is classified into the genus *Pantoea* according to the classification known to a person skilled in the art of microbiology. Some species of *Enterobacter agglomerans* have been recently re-classified into *Pantoea agglomerans, Pantoea ananatis, Pantoea stewartii,* or the like, based on the nucleotide sequence analysis of 16S rRNA, etc. (Int. J. Syst. Bacteriol., 1993, 43, 162-173). Bacteria belonging to the genus *Pantoea* include bacteria re-classified into the genus *Pantoea* as described above.

Typical strains of the *Pantoea* bacteria include *Pantoea ananatis, Pantoea stewartii, Pantoea agglomerans,* and *Pantoea citrea*. Specific examples include the following strains:

*Pantoea ananatis* AJ13355 (FERM BP-6614, European Patent Laid-open No. 0952221)

*Pantoea ananatis* AJ13356 (FERM BP-6615, European Patent Laid-open No. 0952221)

Although these strains are described as *Enterobacter agglomerans* in European Patent Laid-open No. 0952221, they are currently classified as *Pantoea* ananatis on the basis of nucleotide sequence analysis of the 16S rRNA etc., as described above.

Examples of the *Enterobacter* bacteria include *Enterobacter agglomerans, Enterobacter aerogenes,* and the like. Specifically, the strains exemplified in European Patent Application Laid-open No. 952221 can be used. Typical strains of the genus *Enterobacter* include *Enterobacter agglomerans* ATCC 12287 strain.

Examples of the *Erwinia* bacteria include *Erwinia amylovora* and *Erwinia carotovora*, and examples of the *Klebsiella* bacteria include *Klebsiella planticola*. Specific examples include the following strains:

*Erwinia amylovora* ATCC 15580 strain

*Erwinia carotovora* ATCC 15713 strain

*Klebsiella planticola* AJ13399 strain (FERM BP-6600, European Patent Laid-open No. 955368)

*Klebsiella planticola* AJ13410 strain (FERM BP-6617, European Patent Laid-open No. 955368)

The coryneform bacteria also include bacteria which have previously been classified into the genus *Brevibacterium* but are presently united into the genus *Corynebacterium* (Liebl and W. et al, 1991, Int. J. Syst. Bacteriol., 41:255-260), and bacteria belonging to the genus *Brevibacterium*, which are closely related to the genus *Corynebacterium*. Specific examples of such coryneform bacteria include the followings:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of these bacteria include the following strains:

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067
*Brevibacterium immariophilum* ATCC 14068
*Brevibacterium lactofermentum* ATCC 13869 (*Corynebacterium glutamicum* ATCC 13869)
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

The bacterium having an amino acid-producing ability can refer to a bacterium having an ability to produce an L-amino acid and secrete it into a medium when it is cultured in the medium, and includes such a bacterium that accumulates the objective L-amino acid in the medium in an amount of 0.5 g/L or more, or 1.0 g/L or more. The L-amino acid can include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine. L-Threonine, L-lysine, and L-glutamic acid are particular examples.

Methods for imparting an L-amino acid-producing ability to such bacteria as mentioned above and methods for enhancing an L-amino acid-producing ability of such bacteria as mentioned above are described below.

To impart the ability to produce an L-amino acid, methods conventionally employed in the breeding of amino acid-producing coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include by acquiring the properties of an auxotrophic mutant, an L-amino acid analogue-resistant strain, or a metabolic regulation mutant, or by constructing a recombinant strain so that it overexpresses an L-amino acid biosynthesis enzyme. Here, in the breeding of L-amino acid-producing bacteria, one or more of the above-described properties such as auxotrophy, analogue resistance, and metabolic regulation mutation can be imparted. The expression of L-amino acid biosynthesis enzyme(s) can be enhanced alone or in combinations of two or more. Furthermore, the methods of imparting properties such as an auxotrophy, analogue resistance, or metabolic regulation mutation can be combined with enhancement of the biosynthesis enzymes.

An auxotrophic mutant strain, L-amino acid analogue-resistant strain, or metabolic regulation mutant strain with the ability to produce an L-amino acid can be obtained by subjecting a parent or wild-type strain to conventional mutatagenesis, such as exposure to X-rays or UV irradiation, or treatment with a mutagen such as N-methyl-N'-nitro-N-nitrosoguanidine, then selecting those which exhibit autotrophy, analogue resistance, or a metabolic regulation mutation and which also have the ability to produce an L-amino acid.

Moreover, the L-amino acid-producing ability can also be imparted or enhanced by increasing the enzymatic activity by gene recombination. An example of the method for increasing enzymatic activity includes modifying the bacterium so that the expression of a gene coding for an enzyme involved in the biosynthesis of an L-amino acid is enhanced. Gene expression can also be increased by introducing an amplification plasmid prepared by introducing a DNA fragment containing the gene into an appropriate plasmid which contains, for example, at least a gene responsible for replication and proliferation of the plasmid in the microorganism, increasing the copy number of the gene on the chromosome by conjugation, transfer, or the like, or introducing a mutation into the promoter region of the gene (refer to International Publication WO95/34672).

When an objective gene is introduced into the aforementioned amplification plasmid or chromosome, any promoter can be used to express the gene so long as the chosen promoter functions in the coryneform bacteria. The promoter can be the native promoter for the gene, or a modified promoter. The expression of a gene can also be controlled by suitably choosing a promoter that strongly functions in coryneform bacteria, or by making the −35 and −10 regions of the promoter closer to the consensus sequence. These methods for enhancing expression of enzyme genes are fully described in International Publication WO00/18935, European Patent Publication No. 1010755, and so forth.

Specific methods for imparting an L-amino acid-producing ability to bacteria and bacteria imparted with L-amino acid-producing ability are exemplified below.

L-Threonine-producing Bacteria

Examples of microorganisms having L-threonine-producing ability include bacteria in which one or more activities of L-threonine biosynthesis system enzymes are enhanced. Examples of L-threonine biosynthetic enzymes include aspartokinase III (lysC), aspartate semialdehyde dehydrogenase (asd), aspartokinase I (thrA), homoserine kinase (thrB), threonine synthase (thrC) encoded by thr operon, and aspartate aminotransferase (aspartate transaminase) (aspC). The names of the genes coding for the respective enzymes are mentioned in the parentheses after the names of the enzymes (the same shall apply throughout this specification). Among these enzymes, aspartate semialdehyde dehydrogenase, aspartokinase I, homoserine kinase, aspartate aminotransferase, and threonine synthase are particular examples. The genes coding for the L-threonine biosynthetic enzymes can be introduced into an *Escherichia* bacterium which has a reduced ability to decompose threonine. An example of such an *Escherichia* bacterium having a reduced ability to decompose threonine is the TDH6strain which is deficient in threonine dehydrogenase activity (Japanese Patent Laid-open No. 2001-346578).

The enzymatic activities of the L-threonine biosynthetic enzymes are inhibited by the end product, L-threonine. Therefore, for constructing L-threonine-producing strains, the genes for the L-threonine biosynthetic enzymes are modified so that the enzymes are desensitized to feedback inhibition by L-threonine in the L-threonine-producing strains. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, the threonine operon can be modified by removing the leader sequence in the attenuation region or the attenuator (refer to Lynn, S. P., et al., J. Mol. Biol. 194: 59-69 (1987); WO02/26993; WO2005/049808).

The native promoter of the threonine operon is present upstream of the threonine operon, and can be replaced with a non-native promoter (refer to WO98/04715) or a threonine operon which has been modified so that expression of the threonine biosynthesis gene is controlled by the repressor and promoter of λ-phage (EP 0593792). Furthermore, in order to modify a bacterium so that it is desensitized to feedback inhibition by L-threonine, a strain resistant to α-amino-β-hydroxyisovaleric acid (AHV) can be selected.

The copy number of the threonine operon that is modified to desensitize to feedback inhibition by L-threonine can be increased, or the expression of the threonine operon can be increased by ligating it to a potent promoter. The copy number can also be increased by, besides amplification using a plasmid, transferring the threonine operon to a genome using a transposon, Mu-phage, or the like.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of such genes effective for L-threonine production include the genes encoding transhydrogenase (pntAB, EP 733712 B), phosphoenolpyruvate carboxylase (pepC, WO95/06114), phosphoenolpyruvate synthase (pps, EP 877090 B), and a gene encoding pyruvate carboxylase from coryneform bacterium or *Bacillus* bacterium (WO99/18228, EP 1092776 A).

Resistance to L-threonine, L-homoserine, or both can be imparted to the host by, for example, enhancing expression of a gene that imparts resistance to L-threonine or L-homoserine. Examples of these genes include rhtA gene (Livshits, V. A. et al., 2003, Res. Microbiol., 154:123-135), rhtB (EP 0994190 A), rhtC gene (EP 1013765 A), yfiK, and yeaS genes (EP 1016710 A). The methods for imparting L-threonine resistance to a host are described in EP 0994190 A and WO90/04636.

Examples of L-threonine-producing bacteria and parent strains which can be used to derive such bacteria include, but are not limited to, strains belonging to the genus *Escherichia*, such as *E. coli* TDH-6/pVIC40 (VKPM B-3996) (U.S. Pat. Nos. 5,175,107, 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and so forth.

The TDH-6 strain is deficient in the thrC gene, as well as being sucrose-assimilative, and the ilvA gene has a leaky mutation. This strain also has a mutation in the rhtA gene, which imparts resistance to high concentration of threonine or homoserine. The B-3996 strain contains the plasmid pVIC40, which was obtained by inserting the thrA*BC operon, including a mutant thrA gene, into the RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

E. coli VKPM B-5318 (EP 0593792 B) can also be used as an L-threonine-producing bacterium or a parent strain. The B-5318 strain is prototrophic with regard to isoleucine, and a temperature-sensitive lambda-phage Cl repressor and PR promoter replace the regulatory region of the threonine operon in the plasmid pVIC40. The VKPM B-5318 strain was deposited as an international deposit at the Russian National Collection of Industrial Microorganisms (VKPM) (1 Dorozhny proezd., 1 Moscow 117545, Russia) on May 3, 1990 under the accession number of VKPM B-5318.

The thrA gene which encodes aspartokinase homoserine dehydrogenase I of Escherichia coli is located at the nucleotide numbers 337 to 2,799 on the genome sequence of the Escherichia coli MG1655 strain registered under Genbank Accession No. U00096, and codes for the protein registered under GenBank accession No. AAC73113. The thrB gene which encodes homoserine kinase of Escherichia coli is located at the nucleotide numbers 2,801 to 3,733 on the genome sequence of the Escherichia coli MG1655 strain registered under Genbank Accession No. U00096, and codes for the protein registered under GenBank accession No. AAC73114. The thrC gene which encodes threonine synthase of Escherichia coli is located at the nucleotide numbers 3,734 to 5,020 on the genome sequence of the Escherichia coli MG1655 strain registered under Genbank Accession No. U00096, and codes for the protein registered under GenBank accession No. AAC73115. These three genes make up the threonine operon thrLABC downstream of the thrL gene, which codes for the leader peptide. To enhance expression of the threonine operon, the attenuator region which affects the transcription can be removed from the operon (WO2005/049808, WO2003/097839).

A mutant thrA gene which codes for aspartokinase homoserine dehydrogenase I resistant to feedback inhibition by threonine, as well as the thrB and thrC genes can be obtained as one operon from the well-known pVIC40 plasmid, which is present in the threonine-producing E. coli strain VKPM B-3996. pVIC40 is described in detail in U.S. Pat. No. 5,705,371.

The rhtA gene is imparts resistance to homoserine and threonine (rht: resistant to threonine/homoserine), and is located at the nucleotide numbers 848,433 to 849,320 (complementary strand) on the genome sequence of the Escherichia coli MG1655 strain registered under Genbank Accession No. U00096, and coding for the protein registered under GenBank accession No. AAC73900. Also, the rhtA23 mutation is an A-for-G substitution at position −1 with respect to the ATG start codon (Livshits, V. A. et al., 2003, Res. Microbiol., 154:123-135, EP 1013765 A).

The asd gene of E. coli is located at the nucleotide numbers 3,571,798 to 3,572,901 (complementary strand) on the genome sequence of the Escherichia coli MG1655 strain registered under Genbank Accession No. U00096, and codes for the protein registered under GenBank accession No. AAC76458. It can be obtained by PCR (refer to White, T. J. et al., Trends Genet, 5, 185 (1989)) utilizing primers prepared based on the nucleotide sequence of the gene. The asd genes of other microorganisms can also be obtained in a similar manner.

The aspC gene of E. coli is located at the nucleotide numbers 983,742 to 984,932 (complementary strand) on the genome sequence of the Escherichia coli MG1655 strain registered under Genbank Accession No. U00096, and codes for the protein registered under GenBank accession No. AAC74014, and can be obtained by PCR. The aspC genes of other microorganisms can also be obtained in a similar manner.

L-Lysine-producing Bacteria

L-Lysine-producing bacteria and methods for constructing them are exemplified below.

Examples of strains having L-lysine-producing ability include, for example, L-lysine analogue-resistant strains and metabolic regulation mutant strains. Examples of L-lysine analogue include, but are not limited to, oxalysine, lysine hydroxamate, S-(2-aminoethyl)-L-cysteine (also abbreviated as "AEC" hereinafter), γ-methyllysine, α-chlorocaprolactam and so forth. Mutant strains having resistance to these lysine analogues can be obtained by subjecting a bacterium belonging to the family Enterobacteriaceae or a coryneform bacterium to a conventional artificial mutagenesis treatment. Specific examples of L-lysine-producing bacteria include Escherichia coli AJ11442 (FERM BP-1543, NRRL B-12185, see Japanese Patent Laid-open No. 56-18596 and U.S. Pat. No. 4,346,170), Escherichia coli VL611 strain (Japanese Patent Laid-open No. 2000-189180), and so forth. As an L-lysine-producing Escherichia coli, the WC196 strain may also be used (see International Publication WO96/17930).

Further, an L-lysine-producing bacterium can also be constructed by increasing activity of an L-lysine biosynthesis system enzyme. Increasing the activity of such an enzyme can be attained by increasing the copy number of the gene coding for the enzyme in cells, or by modifying an expression control sequence thereof.

A gene can be modified to enhance expression by, for example, increasing the copy number of the gene in the cells by means of genetic recombination techniques. For example, a recombinant DNA can be prepared by ligating a DNA fragment containing the gapA gene with a vector, such as a multi-copy vector, which is able to function in a host microorganism, and introducing the DNA into a bacterium to transform it.

Increasing the copy number of a gene can also be achieved by introducing multiple copies of the gene into a genomic DNA of a bacterium. In order to introduce multiple copies of a gene into a genomic DNA of a bacterium, homologous recombination is carried out by using a sequence which is present in multiple copies in the genomic DNA as targets. As sequences which is present in multiple copies in genomic DNA, repetitive DNA, and inverted repeats present at the end of a transposable element can be used. Another gene may be introduced next to the gapA gene on a genome in tandem, or it multiple copies may be introduced into an unnecessary gene on a genome. Such gene transfer can be attained by using a temperature sensitive vector or an integration vector.

Alternatively, as disclosed in Japanese Patent Laid-open No. 2-109985, it is also possible to incorporate the gene into a transposon, and transfer it, which results in the introduction of multiple copies of the genes into the genomic DNA. Transfer of the gene to the genome can be confirmed by performing Southern hybridization using a part of the gene as a probe.

Further, in addition to the aforementioned increase of the gene copy number, expression of gene can be enhanced by replacing an expression control sequence such as a promoter of the gene on a genome DNA or plasmid with a stronger one, by making the −35 and −10 regions of the gene closer to the consensus sequence, by amplifying a regulator that increases expression of the gene, or by deleting or attenuating a regulator that decreases expression of the gene according to the methods described in International Publication WO00/18935. For example, the lac promoter, trp promoter, trc promoter, tac promoter, araBA promoter, lambda phage PR promoter and PL promoter, tet promoter, T7 promoter, Φ10 promoter, and so forth are known as strong promoters. A promoter or SD region of the gapA gene can also be modified so as to become stronger by introducing a nucleotide substitution or the like. Examples of the method for evaluating strength of a promoter and strong promoters are described in the paper of Goldstein et al. (Prokaryotic promoters in biotechnology, Biotechnol. Annu. Rev., 1995, 1, 105-128) and so forth. In addition, it is known that substitution of several nucleotides in a spacer between the ribosome binding site (RBS) and translation initiation codon, especially a sequence immediately upstream from the initiation codon, greatly affects mRNA translation efficiency, and therefore this sequence may be modified. Expression control regions such as promoter of a gene may also be identified by using a promoter search vector or gene analysis software such as GENETYX. By such substitution or modification of promoter as described above, expression of a gene is enhanced. Substitution of an expression control sequence can also be attained by, for example, a method using a temperature sensitive plasmid or Red-driven integration (WO2005/010175).

Examples of genes coding for L-lysine biosynthetic enzymes include genes coding for enzymes of the diaminopimelate pathway such as dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934 for all the foregoing genes), phosphoenolpyrvate carboxylase gene (ppc) (Japanese Patent Laid-open No. 60-87788), aspartate aminotransferase gene (aspC) (Japanese Patent Publication (Kokoku) No. 6-102028), diaminopimelate epimerase gene (dapF) (Japanese Patent Laid-open No. 2003-135066), and aspartate semialdehyde dehydrogenease gene (asd) (WO00/61723), and genes coding for enzymes of the aminoadipic acid pathway such as homoaconitate hydratase gene (Japanese Patent Laid-open No. 2000-157276). In addition, the parent strain may show an increased level of expression of the gene involved in energy efficiency (cyo) (EP 1170376 A), the gene coding for nicotinamide nucleotide transhydrogenase (pntAB) (U.S. Pat. No. 5,830,716), the ybjE gene coding for a protein having L-lysine excretion activity (WO2005/073390), the gene coding for glutamate dehydrogenase (gdhA) (Valle F. et al., 1983, Gene 23:199-209), or an arbitrary combination of these. Abbreviations for the genes are shown in the parentheses.

It is known that the wild-type dihydrodipicolinate synthase derived from $Escherichia\ coli$ suffers from feedback inhibition by L-lysine, and it is known that the wild-type aspartokinase derived from $Escherichia\ coli$ suffers from suppression and feedback inhibition by L-lysine. Therefore, when the dapA gene and lysC gene are used, these genes can encode for mutant enzymes desensitized to the feedback inhibition by L-lysine.

Examples of DNA encoding a mutant dihydrodipicolinate synthetase desensitized to feedback inhibition by L-lysine include a DNA encoding such a protein having an amino acid sequence in which the histidine residue at the position 118 is replaced by tyrosine residue. Examples of DNA encoding a mutant aspartokinase desensitized to feedback inhibition by L-lysine include a DNA encoding an AKIII having an amino acid sequence in which the threonine residue at the position 352, the glycine residue at the position 323, and the methionine residue at the position 318 are replaced by isoleucine, asparagine and isoleucine residues, respectively (for these mutants, see U.S. Pat. Nos. 5,661,012 and 6,040,160). Such mutant DNAs can be obtained by site-specific mutagenesis using PCR or the like.

A wide host-range plasmids RSFD80, pCAB1, and pCABD2 are known which contain a mutant dapA gene encoding a mutant dihydrodipicolinate synthase and a mutant lysC gene encoding a mutant aspartokinase (U.S. Pat. No. 6,040,160). $Escherichia\ coli$ JM109 strain transformed with the plasmid was named AJ12396 (U.S. Pat. No. 6,040,160), and the strain was deposited at the National Institute of Bioscience and Human-Technology, Agency of Industrial Science and Technology, Ministry of International Trade and Industry (currently National Institute of Advanced Industrial Science and Technology, International Patent Organism Depositary) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a conventional method.

Examples of such enzymes involved in the L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of both genes can be decreased by, for example, the method described in WO2006/078039.

In order to reduce or eliminate activities of these enzymes, a mutation may be introduced into the genes which encode the enzymes on the genome by a usual mutagenesis method or gene recombination technique so that intracellular activities of the enzymes are reduced or eliminated. Such introduction of a mutation can be achieved by, for example, using genetic recombination to eliminate the genes coding for the enzymes on the genome or to modify an expression control sequence such as a promoter or the Shine-Dalgarno (SD) sequence. It can also be achieved by introducing a mutation for amino acid substitution (missense mutation), a stop codon (nonsense mutation), or a frame shift mutation for adding or deleting one or two nucleotides into regions coding for the enzymes on the genome, or partially or totally deleting the genes (Wang, J. P. et al., 2006, J. Agric. Food Chem., 54:9405-9410; Winkler W. C., 2005, Curr. Opin. Chem. Biol., 9:594-602; Qiu Z. and Goodman M. F., 1997, J. Biol. Chem., 272:8611-8617; Wente, S. R. and Schachman, H. K., 1991, J. Biol. Chem., 266:20833-20839). The enzymatic activities can also be decreased or eliminated by constructing a gene coding for a mutant enzyme in which the coding region is totally or partially deleted, and substituting it for a normal gene on the genome by homologous recombination or the like, or by introducing a transposon or IS factor into the gene.

For example, in order to introduce a mutation that decreases or eliminates the activities of the above-mentioned enzymes by genetic recombination, the following methods are used. A mutant gene is prepared by modifying a partial sequence of an objective gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the objective gene on the genome. Examples of such gene substitution using homologous recombination include methods of using a linear DNA such as the method called Red-driven integration (Datsenko, K. A, and Wanner, B. L., 2000, Proc. Natl. Acad. Sci. USA, 97:6640-6645), and the method utilizing the Red driven integration in combination with an excisive system derived from λ phage (Cho, E. H., Gumport, R. I., Gardner, J. F., 2002, J. Bacteriol., 184:5200-5203) (refer to WO2005/010175), a method of using a plasmid containing a temperature sensitive replication origin (U.S. Pat. No. 6,303,383, Japanese Patent Laid-open No. 05-007491), and so forth. Further, such site-specific mutagenesis based on gene substitution using homologous recombination can also be performed by using a plasmid that is not able to replicate in a host.

Examples of L-lysine-producing bacteria include *Escherichia coli*WC196ΔcadAΔldc/pCABD2 (WO2006/078039). The strain was constructed by introducing the plasmid pCABD2 containing lysine biosynthesis genes (U.S. Pat. No. 6,040,160) into the WC196 strain having disrupted cadA and ldcC genes, which encode lysine decarboxylase. The WC196 strain was bred from the W3110 strain, which was derived from *Escherichia coli* K-12, by replacing the wild-type lysC gene on the chromosome of the W3110 strain with a mutant lysC gene encoding a mutant aspartokinase III in which threonine at position 352 was replaced with isoleucine, resulting in desensitization of the feedback inhibition thereof by L-lysine (U.S. Pat. No. 5,661,012), and conferring AEC resistance to the resulting strain (U.S. Pat. No. 5,827,698). The WC196 strain was designated *Escherichia coli* AJ13069, deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698). The WC196ΔcadAΔldc strain itself is also a L-lysine-producing bacterium. The WC196ΔcadAΔldc was designated AJ110692, and deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit and assigned an accession number of FERM BP-11027.

The plasmid pCABD2 contains a mutant dapA gene derived from *Escherichia coli* and coding for a dihydrodipicolinate synthase (DDPS) having a mutation for desensitization to the feedback inhibition by L-lysine, a mutant lysC gene derived from *Escherichia coli* and coding for aspartokinase III having a mutation for desensitization to the feedback inhibition by L-lysine, the dapB gene derived from *Escherichia coli* and coding for dihydrodipicolinate reductase, and the ddh gene derived from *Brevibacterium lactofermentum* and coding for diaminopimelate dehydrogenase (International Publications WO95/16042 and WO01/53459).

The procedures described above for enhancing gene expression of the enzymes involved in the L-lysine biosynthesis, and the methods for reducing the enzymatic activities can similarly be applied to genes coding for other L-amino acid biosynthesis enzymes.

Examples of L-lysine producing coryneform bacteria include AEC-resistant mutant strains (*Brevibacterium lactofermentum* AJ11082 (NRRL B-11470) strain etc., refer to Japanese Patent Publication Nos. 56-1914, 56-1915, 57-14157, 57-14158, 57-30474, 58-10075, 59-4993, 61-35840, 62-24074, 62-36673, 5-11958, 7-112437 and 7-112438); mutant strains requiring an amino acid such as L-homoserine for their growth (refer to Japanese Patent Publication Nos. 48-28078 and 56-6499); mutant strains showing resistance to AEC and further requiring an amino acid such as L-leucine, L-homoserine, L-proline, L-serine, L-arginine, L-alanine and L-valine (refer to U.S. Pat. Nos. 3,708,395 and 3,825,472); L-lysine-producing mutant strains showing resistance to DL-α-amino-ε-caprolactam, α-amino-lauryllactam, aspartic acid analogue, sulfa drug, quinoid and N-lauroylleucine; L-lysine-producing mutant strains showing resistance to oxaloacetate decarboxylase or a respiratory tract enzyme inhibitor (Japanese Patent Laid-open Nos. 50-53588, 50-31093, 52-102498, 53-9394, 53-86089, 55-9783, 55-9759, 56-32995, 56-39778, Japanese Patent Publication Nos. 53-43591 and 53-1833); L-lysine-producing mutant strains requiring inositol or acetic acid (Japanese Patent Laid-open Nos. 55-9784 and 56-8692); L-lysine-producing mutant strains that are susceptible to fluoropyruvic acid or a temperature of 34° C. or higher (Japanese Patent Laid-open Nos. 55-9783 and 53-86090); L-lysine-producing mutant strains of *Brevibacterium* or *Corynebacterium* bacteria showing resistance to ethylene glycol (U.S. Pat. No. 4,411,997) and so forth.

L-Cysteine-producing Bacteria

Examples of L-cysteine-producing bacteria and parent strains which can be used to derive such bacteria include, but not limited to, *Escherichia* bacteria such as *E. coli* JM15transformed with multiple kinds of cysE gene alleles encoding serine acetyltransferase resistant to feedback inhibition (U.S. Pat. No. 6,218,168, Russian Patent Application No. 2003121601), *E. coli* W3110 in which a gene encoding a protein suitable for excretion of cytotoxic substances is overexpressed (U.S. Pat. No. 5,972,663), *E. coli* strain having decreased cysteine desulfhydrase activity (Japanese Patent Laid-open No. 11-155571), and *E. coli* W3110 in which activity of the positive transcriptional control factor of the cysteine regulon encoded by the cysB gene is increased (WO01/27307).

L-Leucine-producing Bacteria

Examples of L-leucine-producing bacteria and parent strains which can be used to derive L-leucine-producing bacteria include, but are not limited to, *Escherichia* bacterial strains, such as *E. coli* strains resistant to leucine (for example, the 57 strain (VKPM B-7386, U.S. Pat. No. 6,124, 121)) or leucine analogues including β-2-thienylalanine, 3-hydroxyleucine, 4-azaleucine, 5,5,5-trifluoroleucine, and so forth (Japanese Patent Publication No. 62-34397 and Japanese Patent Laid-open No. 8-70879), *E. coli* strains obtained by the genetic engineering method described in WO96/06926, *E. coli* H-9068 (Japanese Patent Laid-open No. 8-70879), and so forth.

The bacterium can be improved by enhancing expression of one or more genes involved in L-leucine biosynthesis. Examples of such genes include the genes of the leuABCD operon, a typical example of which is the mutant leuA gene coding for isopropyl malate synthase which has been mutated to be desensitized to feedback inhibition by L-leucine (U.S. Pat. No. 6,403,342). In addition, the bacterium can be improved by enhancing expression of one or more genes coding for proteins which increase export of L-amino acid from bacterial cells. Examples of such genes include the b2682 and b2683 genes (the ygaZH genes) (EP 1239041 A2).

Examples of L-isoleucine-producing strains of coryneform bacteria include the coryneform bacterium in which the brnE gene coding for a branched chain amino acid excretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), the coryneform bacterium of which homoserine dehydrogenase is enhanced (Japanese Patent Laid-open No. 62-91193), the threonine hydroxamete resistant strain (Japanese Patent Laid-open No 62-195293), α-ketomalonic acid resistant strain (Japanese Patent Laid-open No. 61-15695), and the methyl lysine resistant strain (Japanese Patent Laid-open No. 61-15696).

L-Histidine-producing Bacteria

Examples of L-histidine-producing bacteria and parent strains which can be used to derive L-histidine-producing bacteria include, but are not limited to, *Escherichia* bacterial strains, such as *E. coli* strain 24 (VKPM B-5945, RU2003677), *E. coli* strain 80 (VKPM B-7270, RU2119536), *E. coli* NRRL B-12116-B12121 (U.S. Pat. No. 4,388,405), *E. coli* H-9342 (FERM BP-6675), *E. coli* H-9343 (FERM BP-6676) (U.S. Pat. No. 6,344,347), *E. coli* H-9341 (FERM BP-6674) (EP 1085087 A), *E. coli* AI80/pFM201 (U.S. Pat. No. 6,258,554), and so forth.

Examples of L-histidine-producing bacteria and parent strains which can be used to derive L-histidine-producing bacteria also include strains in which the expression of one or more genes encoding L-histidine biosynthetic enzymes are enhanced. Examples of such genes include the genes encoding ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore the ability to produce L-histidine can also be efficiently enhanced by introducing a mutation which confers resistance to the feedback inhibition to the gene coding for ATP phosphoribosyltransferase (hisG) (Russian Patent Nos. 2003677 and 2119536).

Specific examples of strains which are able to produce L-histidine include *E. coli* FERM-P 5038 and 5048 which have been transformed with a vector carrying a DNA encoding an L-histidine biosynthetic enzyme (Japanese Patent Laid-open No. 56-005099), *E. coli* strains transformed with a gene encoding a protein involved in amino acid export (EP 1016710 A), *E. coli* 80 strain which is resistant to sulfaguanidine, DL-1,2,4-triazole-3-alanine, and streptomycin (VKPM B-7270, Russian Patent No. 2119536), and so forth.

L-Glutamic Acid-producing Bacteria

Examples of L-glutamic acid-producing bacteria and parent strains which can be used to derive L-glutamic acid-producing bacteria include, but are not limited to, *Escherichia* bacterial strains, such as *E. coli* VL334thrC⁺ (EP 1172433). *E. coli* VL334 (VKPM B-1641) is auxotrophic for L-isoleucine and L-threonine and contains mutant thrC and ilvA genes (U.S. Pat. No. 4,278,765). A wild-type allele of the thrC gene was transferred by general transduction using bacteriophage P1 grown on wild-type *E. coli* K12 (VKPM B-7) cells, resulting in the L-isoleucine auxotrophic L-glutamic acid-producing strain VL334thrC⁺ (VKPM B-8961).

Examples of L-glutamic acid-producing bacteria and parent strains which can be used to derive L-glutamic acid-producing bacteria also include, but are not limited to, strains in which expression of one or more genes encoding an L-glutamic acid biosynthetic enzyme is enhanced. Examples of such genes include the genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), methyl citrate synthase (prpC), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth. Among these enzymes, glutamate dehydrogenase, citrate synthase, phosphoenolpyruvate carboxylase, and methyl citrate synthase are particular examples.

Examples of strains which have been modified so that expression of the citrate synthetase gene, the phosphoenolpyruvate carboxylase gene, and/or the glutamate dehydrogenase gene is enhanced include those disclosed in EP 1078989 A, EP 955368 A, and EP 952221 A.

Examples of L-glutamic acid-producing bacteria and parent strains which can be used to derive L-glutamic acid-producing bacteria also include strains in which the activity of one or more enzymes that catalyze one or more reactions which direct synthesis of one or more compounds other than L-glutamic acid, for example, by directing synthesis away from the biosynthetic pathway of L-glutamic acid, is reduced or eliminated. Examples of these enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and so forth. *Escherichia* bacteria without α-ketoglutarate dehydrogenase activity or with reduced α-ketoglutarate dehydrogenase activity and methods to obtain such bacteria are described in U.S. Pat. Nos. 5,378,616 and 5,573,945.

Specifically, these strains include the following:
*E. coli* W3110sucA::Km^r
*E. coli* AJ12624 (FERM BP-3853)
*E. coli* AJ12628 (FERM BP-3854)
*E. coli* AJ12949 (FERM BP-4881)

*E. coli* W3110sucA::Km^r is obtained by disrupting the α-ketoglutarate dehydrogenase gene (hereinafter also referred to as the "sucA gene") of *E. coli* W3110. This strain is completely deficient in α-ketoglutarate dehydrogenase.

Examples of coryneform bacteria with decreased α-ketoglutarate dehydrogenase activity include, for example, the following strains:

*Brevibacterium lactofermentum* L30-2 strain (Japanese Patent Laid-open No. 2006-340603)
*Brevibacterium lactofermentum* ΔS strain (WO95/34672)
*Brevibacterium lactofermentum* AJ12821 (FERM BP-4172, French Patent No. 9401748)
*Brevibacterium flavum* AJ12822 (FERM BP-4173, French Patent No. 9401748)
*Corynebacterium glutamicum* AJ12823 (FERM BP-4174, French Patent No. 9401748)
*Corynebacterium glutamicum* L30-2 strain (Japanese Patent Laid-open No. 2006-340603)

Other examples of L-glutamic acid-producing bacterium include *Escherichia* bacteria that are resistant to an aspartic acid antimetabolite. These strains can also be deficient in α-ketoglutarate dehydrogenase and include, for example, *E. coli* AJ13199 (FERM BP-5807) (U.S. Pat. No. 5,908,768); FFRM P-12379, which additionally is decreased in an activity to decompose L-glutamic acid (U.S. Pat. No. 5,393,671); AJ13138 (FERM BP-5565) (U.S. Pat. No. 6,110,714), and so forth.

An example of an L-glutamic acid-producing bacterium which belongs to *Pantoea ananatis* is the *Pantoea ananatis* AJ13355 strain. This strain was isolated from soil in Iwata-shi, Shizuoka-ken, Japan, and was identified as being able to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was originally identified as *Enterobacter agglomerans* when it was isolated, and deposited as *Enterobacter agglomerans* AJ13355. However, it was recently re-classified as *Pantoea ananatis* on the basis of nucleotide sequencing of 16S rRNA and so forth.

Furthermore, examples of an L-glutamic acid-producing bacterium of *Pantoea ananatis* also include *Pantoea* bacteria deficient in α-ketoglutarate dehydrogenase (αKGDH) activity or having reduced αKGDH activity. Examples of such a strain include AJ13356 (U.S. Pat. No. 6,331,419), which was derived by deleting the αKGDH-E1 subunit gene (sucA) in AJ13355, and the SC17sucA strain (U.S. Pat. No. 6,596,517), which is a sucA gene deficient strain derived from the SC17 strain, selected from AJ13355 for its low phlegm production properties. The AJ13356 strain was deposited at the National Institute of Bioscience and Human-Technology, Agency of Industrial Science and Technology (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains were deposited at the aforementioned depository as *Enterobacter agglomerans*, they are referred to as *Pantoea* ananatis in this specification. The SC17sucA strain was assigned the private number of AJ417, and deposited at the National Institute of Advanced Industrial Science and Technology, International Patent Organism Depositary on Feb. 26, 2004, under an accession number of FERM BP-08646.

Examples of L-glutamic acid-producing *Pantoea* ananatis bacteria further include SC17sucA/RSFCPG+pSTVCB, AJ13601, NP106, and NA1 strains. The SC17sucA/RSFCPG+pSTVCB strain was obtained by introducing the plasmid RSFCPG containing the citrate synthase gene (gltA), phosphoenolpyruvate carboxylase gene (ppsA), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain for its resistance to high concentration of L-glutamic acid at a low pH. Furthermore, the NP106 strain was derived from the AJ13601 strain by eliminating the RSFCPG+pSTVCB plasmid. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned accession number FERM P-17516. Then, the deposit was converted into an international deposit under the provisions of the Budapest Treaty on Jul. 6, 2000, and assigned an accession number FERM BP-7207.

Furthermore, the ability to produce L-glutamic acid can also be imparted to coryneform bacteria by a method of amplifying the yggB gene coding for the mechanosensitive channel (WO2006/070944), and a method of introducing a mutant yggB gene in which a mutation is introduced into the coding region. The yggB gene is a gene located at the nucleotide numbers 1,337,692 to 1,336,091 (complementary strand) of the genome sequence of *Corynebacterium glutamicum* ATCC 13032 strain registered with Genbank Accession No. NC_003450, and coding for a membrane protein also called NCgl1221 and registered with GenBank accession No. NP_600492.

Examples of other methods for imparting or enhancing L-glutamic acid-producing ability also include a method of imparting resistance to an organic acid analogue, a respiratory chain inhibitor, etc., and a method of imparting sensitivity to a cell wall synthesis inhibitor. Examples of such methods include the methods of imparting resistance to monofluoroacetic acid (Japanese Patent Laid-open No. 50-113209), the method of imparting resistance to adenine or thymine (Japanese Patent Laid-open No. 57-065198), the method of attenuating urease (Japanese Patent Laid-open No. 52-038088), the method of imparting resistance to malonic acid (Japanese Patent Laid-open No. 52-038088), the method of imparting resistance to benzopyrones or naphthoquinones (Japanese Patent Laid-open No. 56-1889), the method of imparting resistance to HOQNO (Japanese Patent Laid-open No. 56-140895), the method of imparting resistance to α-ketomalonic acid (Japanese Patent Laid-open No. 57-2689), the method of imparting resistance to guanidine (Japanese Patent Laid-open No. 56-35981), the method of imparting sensitivity to penicillin (Japanese Patent Laid-open No. 4-88994), and so forth.

Specific examples of such resistant strains include the following strains:

*Brevibacterium flavum* AJ3949 (FERM BP-2632; Japanese Patent Laid-open No. 50-113209)

*Corynebacterium glutamicum* AJ11628 (FERM P-5736; Japanese Patent Laid-open No. 57-065198)

*Brevibacterium flavum* AJ11355 (FERM P-5007; Japanese Patent Laid-open No. 56-1889)

*Corynebacterium glutamicum* AJ11368 (FERM P-5020; Japanese Patent Laid-open No. 56-1889)

*Brevibacterium flavum* AJ11217 (FERM P-4318; Japanese Patent Laid-open No. 57-2689)

*Corynebacterium glutamicum* AJ11218 (FERM P-4319; Japanese Patent Laid-open No. 57-2689)

*Brevibacterium flavum* AJ11564 (FERM BP-5472; Japanese Patent Laid-open No. 56-140895)

*Brevibacterium flavum* AJ11439 (FERM BP-5136; Japanese Patent Laid-open No. 56-35981)

*Corynebacterium glutamicum* H7684 (FERM BP-3004; Japanese Patent Laid-open No. 04-88994)

*Brevibacterium lactofermentum* AJ11426 (FERM P-5123; Japanese Patent Laid-open No. 56-048890)

*Corynebacterium glutamicum* AJ11440 (FERM P-5137; Japanese Patent Laid-open No. 56-048890)

*Brevibacterium lactofermentum* AJ11796 (FERM P-6402; Japanese Patent Laid-open No. 58-158192)

L-Phenylalanine-Producing Bacteria

Examples of L-phenylalanine-producing bacteria and parent strains which can be used to derive L-phenylalanine-producing bacteria include, but are not limited to, *Escherichia* bacterial strains, such as *E. coli* AJ12739 (tyrA::Tn10, tyrR) (VKPM B-8197) which lacks chorismate mutase-prephenate dehydrogenase and the tyrosine repressor (WO03/044191), *E. coli* HW1089 (ATCC 55371) which contains the pheA34 gene coding for chorismate mutase-prephenate dehydratase which has been mutated to be desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Also, the following strains can be used to derive L-phenylalanine-producing bacteria: *E. coli* K-12 [W3110(tyrA)/pPHAB (FERM BP-3566) which contains genes coding for chorismate mutase-prephenate dehydratase which has been mutated to be desensitized to feedback inhibition, *E. coli* K-12 [W3110(tyrA)/pPHAD] (FERM BP-12659), *E. coli* K-12 [W3110(tyrA)/pPHATerm] (FERM BP-12662), and *E. coli* K-12 [W3110(tyrA)/pBR-aroG4, pACMAB] (also known as AJ12604 (FERM BP-3579) (EP 488424 B1). Furthermore, *Escherichia* L-phenylalanine-producing bacteria with enhanced activity of the protein encoded by the yedA gene or the yddG gene can also be used (U.S. Patent Published Applications Nos. 2003/0148473 and 2003/0157667, WO03/044192).

As phenylalanine-producing coryneform bacteria, the *Cornebacterium glutamicum* BPS-13 (FERM BP-1777), K77 (FERM BP-2062), and K78 (FERM BP-2063) (European Patent Laid-open No. 331145, Japanese Patent Laid-open No. 02-303495), of which phosphoenolpyruvate carboxylase or pyruvate kinase activity is reduced, tyrosine-auxotrophic strain (Japanese Patent Laid-open No. 05-049489), and so forth can be used.

A bacterium which efficiently produces phenylalanine can also be obtained by modifying a bacterium so that the bacterium incorporates by-products, for example, by increasing the expression amount of the L-tryptophan uptake gene, tnaB or mtr, or the L-tyrosine uptake gene, tyrP (European Patent No. 1484410).

L-Tryptophan-producing Bacteria

Examples of L-tryptophan-producing bacteria and parent strains which can be used to derive L-tryptophan-producing bacteria include, but are not limited to, *Escherichia* bacterial strains, such as *E. coli* JP4735/pMU3028 (DSM10122) and *E. coli* JP6015/pMU91 (DSM10123) which lack tryptophanyl-tRNA synthetase encoded by a mutant trpS gene (U.S. Pat. No. 5,756,345), *E. coli* SV164 (pGH5) which contains the serA allele encoding phosphoglycerate dehydrogenase and the trpE allele encoding anthranilate synthase, which are desensitized to feedback inhibition by serine and tryptophan, respectively (U.S. Pat. No. 6,180,373), *E. coli* AGX17 (pGX44) (NRRL B-12263), and *E. coli* AGX6(pGX50)aroP (NRRL B-12264) which lack tryptophanase (U.S. Pat. No. 4,371,614), and *E. coli* AGX17/pGX50, pACKG4-pps in which phosphoenolpyruvate-producing ability is enhanced (WO97/08333, U.S. Pat. No. 6,319,696). L-Tryptophan-producing bacteria belonging to the genus *Escherichia* with enhanced activity of the protein encoded by the yedA gene or the yddG gene can also be used (U.S. Patent Published Application Nos. 2003/0148473 and 2003/0157667).

Examples of L-tryptophan-producing bacteria and parent strains which can be used to derive L-tryptophan-producing bacteria also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (chorismate mutase/prephenate dehydratase, CM/PDH). Among these enzymes, phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, and chorismate mutase-prephenate dehydratase are particular examples. Anthranilate synthase and phosphoglycerate dehydrogenase both suffer from feedback inhibition by L-tryptophan and L-serine, and therefore a mutation desensitizing the feedback inhibition can be introduced into the genes encoding these enzymes. Specific examples of strains having such a mutation include *E. coli* SV164 having a desensitized type anthranilate synthase and a transformant strain obtained by introducing pGH5 (WO94/08031) containing a mutant serA gene coding for phosphoglycerate dehydrogenase desensitized to the feedback inhibition into *E. coli* SV164.

Examples of L-tryptophan-producing bacteria and parent strains which can be used to derive L-tryptophan-producing bacteria also include strains which have been transformed with the tryptophan operon, which contains a gene encoding inhibition-desensitized anthranilate synthase (Japanese Patent Laid-open Nos. 57-71397, 62-244382, U.S. Pat. No. 4,371,614). Moreover, L-tryptophan-producing ability can be imparted by enhancing expression of a gene which encodes tryptophan synthase in the tryptophan operon (trpBA). Tryptophan synthase includes both α and β subunits, which are encoded by trpA and trpB, respectively. In addition, L-tryptophan-producing ability can be improved by enhancing expression of the isocitrate lyase-malate synthase operon (WO2005/103275).

As coryneform bacteria, *Corynebacterium glutamicum* AJ12118 (FERM BP-478, Japanese Patent No. 01681002), which is resistant to sulfaguanidine, the coryneform bacterium introduced with the tryptophan operon (Japanese Patent Laid-open No. 63-240794), and the coryneform bacterium introduced with a gene coding for shikimate kinase derived from a coryneform bacterium (Japanese Patent Laid-open No. 01-994749) can be used.

L-Proline-producing Bacteria

Examples of L-proline-producing bacteria and parent strains which can be used to derive L-proline-producing bacteria include, but are not limited to, *Escherichia* bacterial strains, such as *E. coli* 702ilvA (VKPM B-8012) which lacks the ilvA gene and can produce L-proline (EP 1172433).

The bacterium can be improved by enhancing expression of one or more genes involved in L-proline biosynthesis. Examples of genes for L-proline-producing bacteria include the proB gene coding for glutamate kinase which is desensitized to feedback inhibition by L-proline (DE Patent 3127361). In addition, the bacterium can be improved by enhancing expression of one or more genes coding for proteins responsible for secretion of L-amino acids from the bacterial cell. Examples of such genes are the b2682 and b2683 genes (ygaZH genes) (EP 1239041 A2).

*Escherichia* bacteria which produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al. (The 15th Miami Winter Symposium, 1983, p. 34), and so forth.

L-Arginine-producing Bacteria

Examples of L-arginine-producing bacteria and parent strains which can be used to derive L-arginine-producing bacteria include, but are not limited to, *Escherichia* bacterial strains, such as *E. coli* strain 237 (VKPM B-7925) (U.S. Patent Published Application No. 2002/058315 A1) and its derivative strains harboring mutant N-acetylglutamate synthase (Russian Patent Application No. 2001112869), *E. coli* strain 382 (VKPM B-7926) (EP 1170358 A1), and an arginine-producing strain transformed with an argA gene encoding N-acetylglutamate synthetase (EP 1170361 A1).

Examples of L-arginine-producing bacteria and parent strains which can be used to derive L-arginine-producing bacteria also include strains in which the expression of one or more genes encoding an L-arginine biosynthetic enzyme are enhanced. Examples of such genes include the N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Valine-producing Bacteria

Examples of L-valine-producing bacteria and parent strains which can be used to derive L-valine-producing bacteria include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by the produced L-valine. Furthermore, the ilvA gene in the operon is desirably disrupted so that threonine deaminase activity is decreased.

Examples of L-valine-producing bacteria and parent strains which can be used to derive L-valine-producing bacteria also include mutants having amino-acyl t-RNA synthetase mutations (U.S. Pat. No. 5,658,766). An example is *E. coli* VL1970, which has a mutation in the ileS gene encoding isoleucine tRNA synthetase. *E. coli* VL1970 was deposited at the Russian National Collection of Industrial Microorganisms (VKPM) (1 Dorozhny proezd., 1 Moscow 117545, Russia) on Jun. 24, 1988 under the accession number VKPM B-4411.

Furthermore, mutant strains which require lipoic acid for growth and/or lack $H^+$-ATPase (WO96/06926) are also effective to derive L-valine-producing bacteria.

Examples of L-valine-producing bacteria of coryneform bacteria include, for example, strains modified so that expression of a gene encoding an L-valine biosynthetic enzyme is enhanced. Examples of the L-valine biosynthesis enzyme include enzymes encoded by genes present on the ilvBNC operon, that is, acetohydroxy acid synthetase encoded by ilvBN and isomero-reductase encoded by ilvC (WO00/50624). Since the ilvBNC operon is subject to expression regulation by L-valine and/or L-isoleucine and/or L-leucine, attenuation can be eliminated to avoid expression suppression by L-valine that is produced.

Impartation of L-valine-producing ability to coryneform bacteria may be performed by decreasing or eliminating activity of at least one kind of enzyme which is involved in a metabolic pathway that decreases L-valine production. For example, decrease of the activity of threonine dehydratase involved in the L-leucine synthesis, or activity of an enzyme that involved in D-panthothenate synthesis is contemplated (WO00/50624).

Examples of methods for imparting L-valine-producing ability also include imparting resistance to an amino acid analogue or the like.

Examples include, for example, mutant strains which are auxotrophic for L-isoleucine and L-methionine, and resistant to D-ribose, purine ribonucleoside or pyrimidine ribonucleoside, and have an ability to produce L-valine (FERM P-1841, FERM P-29, Japanese Patent Publication No. 53-025034), mutant strains resistant to polyketides (FERM P-1763, FERM P-1764, Japanese Patent Publication No. 06-065314), and mutant strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007, Japanese Patent No. 3006929).

L-Isoleucine-producing Bacteria

Examples of L-isoleucine producing bacteria and parent strains which can be used to derive L-isoleucine-producing bacteria include, but are not limited to, mutants which are resistant to 6-dimethylaminopurine (Japanese Patent Laid-open No. 5-304969), mutants which are resistant to isoleucine analogues such as thiaisoleucine and isoleucine hydroxamate, and mutants which are additionally resistant to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxate synthase, are also effective to derive L-isoleucine-producing bacteria (Japanese Patent Laid-open No. 2-458, FR 0356739, and U.S. Pat. No. 5,998,178).

Examples of L-isoleucine-producing strains of coryneform bacteria include the coryneform bacterium of which brnE gene coding for a branched chain amino acid excretion protein is amplified (Japanese Patent Laid-open No. 2001-169788), the coryneform bacterium imparted with L-isoleucine-producing ability by protoplast fusion with an L-lysine-producing bacterium (Japanese Patent Laid-open No. 62-74293), the coryneform bacterium in which homoserine dehydrogenase is enhanced (Japanese Patent Laid-open No. 62-91193), the threonine hydroxamete resistant strain (Japanese Patent Laid-open No 62-195293), α-ketomalonic acid resistant strain (Japanese Patent Laid-open No. 61-15695), and the methyl lysine resistant strain (Japanese Patent Laid-open No. 61-15696).

L-Methionine-producing Bacteria

Examples of L-methionine-producing bacteria and parent strains which can be used to derive L-methionine producing bacteria include, but are not limited to, L-threonine-auxotrophic mutant strain and norleucine-resistant mutant strain (Japanese Patent Laid-open No. 2000-139471). Furthermore, a methionine repressor-deficient strain and recombinant strains transformed with genes encoding proteins involved in L-methionine biosynthesis such as homoserine transsuccinylase and cystathionine γ-synthase (Japanese Patent Laid-open No. 2000-139471) can also be used as parent strains.

When the aforementioned L-amino acid-producing bacteria are bred by gene recombination, the genes are not limited to genes having the genetic information described above or genes having known sequences, but also include genes having conservative mutations, such as homologues or artificially modified genes, can also be used so long as the functions of the encoded proteins are not degraded. That is, they may be genes encoding a known amino acid sequence containing one or more substitutions, deletions, insertions, additions or the like of one or several amino acid residues at one or several positions.

Although the number of the "one or several" amino acid residues may differ depending on the position in the three-dimensional structure or the types of amino acid residues of the protein, specifically, it may be 1 to 20, 1 to 10, or even 1 to 5. The conservative mutation is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. The conservative mutation is typically a conservative substitution, and substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like may be a result of a naturally-occurring mutation or a variation due to an individual difference or difference of species of a microorganism from which the genes are derived (mutant or variant). Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, such genes having conservative mutation(s) as described above may encode a protein having a homology of 80% or more, 90% or more, 95% or more, or even 97% or more, to the entire encoded amino acid sequence and have a function equivalent to that of the wild-type protein.

Moreover, codons in the gene sequences may be replaced with other codons which are easily used in the host into which the genes are introduced.

The genes having conservative mutation(s) may be obtained by methods usually used in mutagenesis treatments such as treatments with mutagenesis agents.

Furthermore, the genes may be a DNA which can hybridize with a complementary sequence of a known gene sequence or a probe which can be prepared from the complementary sequence under stringent conditions and encodes a protein having a function equivalent to that of the known gene product. The "stringent conditions" can be conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, or even not less than 97% homologous, hybridize to each other, and DNAs less homologous than the above do not hybridize to each other, or conditions of washing once, or 2 or 3 times, at a salt concentration and temperature corresponding to washing typical of Southern hybridization, i.e., 1×SSC, 0.1% SDS at 60° C.; 0.1×SSC, 0.1% SDS at 60° C.; or even 0.1×SSC, 0.1% SDS at 68° C.

As the probe, a part of the sequence which is complementary to the gene can also be used. Such a probe can be prepared by PCR using oligonucleotides prepared on the basis of the known gene sequence as primers and a DNA fragment containing the nucleotide sequences as a template. For example, when a DNA fragment having a length of about 300 bp is used as the probe, the washing conditions of hybridization may be 50° C., 2×SSC and 0.1% SDS.

The aforementioned descriptions concerning gene homologues and conservative mutations are similarly applied to the aforementioned lipase genes.

<3> Method for Producing L-Amino Acid

The method for producing an L-amino acid includes the steps of preparing a processed product of a microalga, which promotes production and accumulation of the L-amino acid by a bacterium having an ability to produce the L-amino acid, by culturing the microalga in a medium, and processing the culture at a midtemperature, culturing the bacterium in a medium containing the processed product of the microalga to produce and accumulate the L-amino acid in the culture, and collecting the L-amino acid from the culture. Since the processed product is a reaction mixture in which the culture of the microalga is processed at a midtemperature or a product obtained by further subjecting the reaction mixture to extraction or fractionation and/or another treatment as described above, it is considered that the processed product contains organic substances produced from organic substances produced by the microalga by the reaction at a midtemperature, or organic substances obtained by further conversion of the foregoing organic substance by another treatment.

The processed product (henceforth also referred to as "mid temperature-processed product") can be a carbon source, and in this case, fatty acids, glucose and glycerol are included as the carbon source.

The expression "as a carbon source" mentioned above means that the processed product can substantially contribute carbon constituting cell components and L-amino acids in proliferation of the bacterium and L-amino acid production. If bacterial growth or L-amino acid production and accumulation are more favorable in culture in a medium to which the midtemperature-processed product is added compared with culture in a medium to which the moderate temperature-processed product is not added, the midtemperature-processed product is estimated to be a carbon source. The medium may contain only the midtemperature-processed product as a carbon source, or may contain other carbon sources.

For the method, batch culture, fed-batch culture and continuous culture may be used. The moderate temperature-processed product in the medium may be present in a starting medium or feed medium, or may be present in both.

The fed-batch culture can refer to a culture method in which a medium is continuously or intermittently fed into a culture vessel, and the medium is not extracted until the end of culture. A continuous culture can mean a method in which a medium is continuously or intermittently fed into a culture vessel, and the medium is extracted from the vessel (usually in a volume equivalent to the volume of fed medium) at the same time. The starting medium can mean the medium used in batch culture, the fed-batch culture, or continuous culture before feeding the feed medium (medium used at the time of the start of the culture), and feed medium can mean a medium which is supplied to a fermentation tank in the fed-batch culture or continuous culture. The batch culture means a method in which fresh medium is prepared for every culture, and a strain is inoculated into the medium, which medium is not changed until harvest.

The midtemperature-processed product may be used at any concentration so long as it is used at a concentration suitable for producing an L-amino acid. Concentrations of the components of the midtemperature-processed product are as follows. Concentration of glucose as a saccharification product of starches in the medium can be about 0.05 to 50 w/v %, about 0.1 to 40 w/v %, or even about 0.2 to 20 w/v %. As for the amount of glycerol and fatty acids as a hydrolysate of fat or oil, about 0.01 to 10 w/v %, about 0.02 to 5 w/v %, or even about 0.05 to 2 w/v % can be present in the medium. The midtemperature-processed product may be independently used, or may also be used in combination with other carbon sources such as glucose, fructose, sucrose, blackstrap molasses, and starch hydrolysate. In this case, although the midtemperature-processed product and other carbon sources may be mixed at an arbitrary ratio, it is desirable that the ratio of the moderate temperature-processed product in the carbon source is 10% by weight or more, 50% by weight or more, 70% by weight or more. Other carbon sources can include saccharides such as glucose, fructose, sucrose, lactose, galactose, blackstrap molasses, starch hydrolysate, and a sugar solution obtained by hydrolysis of biomass, alcohols such as ethanol and glycerol, and organic acids such as fumaric acid, citric acid, and succinic acid.

The mid-temperature-processed product may be present at a certain constant concentration throughout the culture period, it may be added only to the feed medium or the starting medium, or if other carbon sources are sufficient, there may be a period where the moderate temperature-processed product temporarily runs short. The term "temporarily" means that, for example, the moderate temperature-processed product may run short for a period corresponding to 10%, 20%, or 30% at most, of the entire fermentation period. Such a case as described above where the concentration of the midtemperature-processed product may temporarily become 0 is included in the scope of the expression "the medium contains the moderate temperature-processed product as a carbon source", so long as there is a period of culture in a medium containing the midtemperature-processed product.

As the medium to be used, media conventionally used in the production of L-amino acids by fermentation using microorganisms can be used, provided that the medium contains the moderate temperature-processed product. That is, conventional media containing, besides a carbon source, a nitrogen source, inorganic ions, and optionally other organic components as required may be used. As the nitrogen source, inorganic ammonium salts such as ammonium sulfate, ammonium chloride, ammonium phosphate, ammonium acetate, and urea, nitrates, organic nitrogen such as soybean hydrolysate, ammonia gas, aqueous ammonia, and so forth may be used. Furthermore, peptone, yeast extract, meat extract, malt extract, corn steep liquor, soybean hydrolysate and so forth can also be utilized. The medium may contain one or more types of these nitrogen sources. These nitrogen sources can also be used for both the starting medium and the feed medium. Furthermore, the same nitrogen source can be used for both the starting medium and the feed medium, or the nitrogen source of the feed medium may be different from that of the starting medium.

The medium can contain a phosphoric acid source and a sulfur source in addition to the carbon source and the nitrogen source. As the phosphoric acid source, potassium dihydrogenphosphate, dipotassium hydrogenphosphate, phosphate polymers such as pyrophosphoric acid and so forth can be utilized. Although the sulfur source may be any substance containing sulfur atoms, sulfuric acid salts such as sulfates, thiosulfates and sulfites, and sulfur-containing amino acids such as cysteine, cystine and glutathione are desirable, and ammonium sulfate is especially desirable.

Furthermore, the medium may contain a growth promoting factor (nutrient having a growth promoting effect) in addition to the aforementioned components. As the growth promoting factor, trace metals, amino acids, vitamins, nucleic acids as well as peptone, casamino acid, yeast extract, soybean protein degradation product and so forth containing the foregoing substances can be used. Examples of the trace metals include iron, manganese, magnesium, calcium and so forth. Examples of the vitamins include vitamin $B_1$, vitamin $B_2$, vitamin $B_6$, nicotinic acid, nicotinamide, vitamin $B_{12}$ and so forth. These growth promoting factors may be contained in the starting medium or the feed medium.

Furthermore, when an auxotrophic mutant that requires an amino acid or the like for growth thereof is used, a required nutrient can be supplemented to the medium. In particular, since the L-lysine biosynthetic pathway is enhanced and L-lysine degrading ability is often attenuated in L-lysine-producing bacteria that can be used for the present invention as described below, one or more types of substances selected from L-threonine, L-homoserine, L-isoleucine and L-methionine are particular examples. The starting medium and the feed medium may have the same or different medium composition. Furthermore, the starting medium and the feed medium may have the same or different sulfur concentration. Furthermore, when the feed medium is fed at multiple stages, the compositions of the feed media fed at the stages may be the same or different.

In addition, the medium used in the present invention may be either a natural medium or synthetic medium, so long as it contains a carbon source, a nitrogen source, and other components as required.

The moderate temperature-processed product may contain components used for amino acids in addition to the carbon source. The nitrogen source and other components in the medium used in the present invention can be reduced compared with usual media as required.

The culture can be performed for 1 to 7 days under aerobic conditions. The culture temperature is 20 to 45° C., 24 to 45° C., or 33 to 42° C. The culture can be performed as aeration culture, with controlling the oxygen concentration to be about 5 to 50%, or about 10%, of the saturation concentration. Furthermore, pH can be controlled to be 5 to 9 during the culture. For adjusting pH, inorganic or organic acidic or alkaline substances, such as calcium carbonate, ammonia gas, and aqueous ammonia, can be used.

If culture is performed under such conditions as described above for about 10 to 120 hours, a marked amount of L-amino acid is accumulated in the culture medium. Although the concentration of L-amino acid accumulated is not limited so long as it enables isolation and collection of the L-amino acid from the medium or cells, it can be 1 g/L or higher, 50 g/L or higher, or even 100 g/L or higher.

When a basic amino acid such as L-lysine is produced, the production may be performed by a method in which fermentation is performed by controlling pH of the medium during culture to be 6.5 to 9.0 and pH of the medium at the end of the culture to be 7.2 to 9.0 and controlling the pressure in the fermentation tank to be positive during the culture, or by supplying carbon dioxide gas or a mixed gas containing carbon dioxide gas to the medium to provide a culture period where the medium contains 2 g/L or 20 mM or more of bicarbonate ions and/or carbonate ions, so that these bicarbonate ions and/or carbonate ions serve as counter ions of cations mainly a basic amino acid, and the objective basic amino acid is then collected (Japanese Patent Laid-open No. 2002-65287, U.S. Patent Published Application No. 2002/0025564, EP 1813677 A).

Further, in L-glutamic acid fermentation, the culture can be performed with precipitating L-glutamic acid in the medium by using a liquid medium adjusted to have a condition under which L-glutamic acid is precipitated. The condition under which L-glutamic acid is precipitated is, for example, pH 5.0 to 4.0, pH 4.5 to 4.0, pH 4.3 to 4.0, or pH 4.0 (European Patent Laid-open No. 1078989).

The L-amino acid can be collected from the culture medium by a combination of known methods such as an ion exchange resin method and precipitation method. When the L-amino acid accumulates in the cells, the cells can be disrupted with, for example, supersonic waves or the like, and the L-amino acid can be collected by the ion exchange resin method or the like from the supernatant obtained by removing the cells from the cell-disrupted suspension by centrifugation. The L-amino acid to be collected may be a free L-amino acid, or may be a salt such as sulfate, hydrochloride, carbonate, ammonium salt, sodium salt, and potassium salt.

The L-amino acid composition may contain bacterial cells, medium components, moisture, and by-product metabolites of the bacterium in addition to the objective L-amino acid. Purity of the collected L-amino acid is 50% or higher, 85% or higher, or 95% or higher (Japanese Patent No. 1214636, U.S. Pat. Nos. 5,431,933, 4,956,471, 4,777,051, 4,946,654, 5,840,358, 6,238,714, U.S. Patent Published Application No. 2005/0025878).

EXAMPLES

Hereafter, the present invention will be explained more specifically with reference to the following non-limiting examples. In the examples, the *Chlorella kessleri* 11H (UTEX 263) and *Nannochloris* sp. UTEX LB 1999 strains were obtained from the University of Texas at Austin, The Culture Collection of Algae (UTEX) (1 University Station A6700, Austin, Tex. 78712-0183, USA).

Example 1

Culture of Microalga *Chlorella kessleri* 11H Strain

The *Chlorella kessleri* 11H strain was cultured at 30° C. and a light intensity of 7,000 lux (culture apparatus: CL-301, TOMY) for 7 days with shaking in 100 mL of the 0.2× Gamborg's B5 medium (NIHON PHARMACEUTICAL) contained in a 500 mL-volume conical flask, and the resultant culture was used as a preculture. The preculture in a volume of 30 mL was added to 1.5 L of the 0.2× Gamborg's B5 medium contained in a 5 L-volume mini jar fermenter (ABLE), and culture was performed at a culture temperature of 30° C. and a light intensity of 20,000 lux for 14 days with blowing 500 mL/minute of a mixed gas of air and 3% $CO_2$ into the medium. As the light source, white light from a fluorescent lamp was used.

| (0.2 × Gamborg's B5 medium) | |
|---|---|
| $KNO_3$ | 500 mg/L |
| $MgSO_4 \cdot 7H_2O$ | 50 mg/L |
| $NaH_2PO_4 \cdot H_2O$ | 30 mg/L |

-continued

| (0.2 × Gamborg's B5 medium) | |
|---|---|
| $CaCl_2 \cdot 2H_2O$ | 30 mg/L |
| $(NH_4)_2SO_4$ | 26.8 mg/L |
| $Na_2$-EDTA | 7.46 mg/L |
| $FeSO_4 \cdot 7H_2O$ | 5.56 mg/L |
| $MnSO_4 \cdot H_2O$ | 2 mg/L |
| $H_3BO_3$ | 0.6 mg/L |
| $ZnSO_4 \cdot 7H_2O$ | 0.4 mg/L |
| KI | 0.15 mg/L |
| $Na_2MoO_2 \cdot 2H_2O$ | 0.05 mg/L |
| $CuSO_4 \cdot 5H_2O$ | 0.005 mg/L |
| $CoCl_2 \cdot 6H_2O$ | 0.005 mg/L |

The medium was sterilized by autoclaving at 120° C. for 15 minutes.

Example 2

Decomposition of Oils and Fats and Starch Derived from Alga by Processing at Midtemperature The alga bodies contained in 9 L of the culture medium obtained by culture according to the method of Example 1 were precipitated by centrifugation, and stored at −80° C. for 24 hours. To the precipitate, 1 L of the culture supernatant was added again, and 2 ml of the suspension was put into a test tube, and incubated at 50° C. and 150 rpm for 18 hours. The above procedure was also performed for a group in which 10 units of amyloglucosidase (Sigma Aldrich, A-9228) was added to the suspension. Each sample was centrifuged to separate precipitate and supernatant, and then organic substances contained in them were measured. The results of the measurements are shown in Table 1. In the sample processed at a mid-temperature, the amounts of oils and fats and starch decreased, whereas the amounts of fatty acids and glycerol or glucose, which are decomposition products of oils and fats or starch, increased as compared with the unprocessed sample. Further, the fatty acids localized in the precipitate, whereas glucose and glycerol were found in the supernatant. Furthermore, with the amyloglucosidase treatment during the processing at a midtemperature, the glucose production amount was increased.

TABLE 1

| Organic substance | Unprocessed (g/L) | Processed at midtemperature (g/L) |
|---|---|---|
| Oil and fat (precipitate) | 6.6 | 2.4 |
| Starch (precipitate) | 2.5 | 0.5 |
| Glycerol (supernatant) | 0.6 | 1.3 |
| Fatty acid (precipitate) | 1.6 | 7.2 |
| Glucose (supernatant) | 0 | 1.3 |
| Glucose (supernatant) + amyloglucosidase treatment | | 2.6 |

Example 3

Production of Fatty Acid from Alga Bodies

The alga bodies contained in 9 L of the culture medium obtained by culture according to the method of Example 1 were precipitated by centrifugation, and stored at −80° C. for 24 hours. To the precipitate, 500 mL of the culture supernatant was added again, and 250 ml of the suspension was put into a 500 mL-volume jar fermenter (ABLE), and incubated at 50° C. and 100 rpm for 18 hours. The obtained sample was centrifuged for precipitation, and the precipitate was suspended in 40 mL of ultrapure water. To 12.5 ml of the suspension, 12.5 ml of ultrapure water and 25 ml of 0.2 N NaOH were added, and then the mixture was stirred at 95° C. for 3 hours. The obtained fatty acid extract was filtered by using filter paper. Fatty acid concentration of the extract was measured, and each was used as a carbon source for amino acid fermentation.

Example 4

L-Lysine Production Culture Using Fatty Acids Derived from Alga As a Carbon Source <4-1> Construction of fadR-Deficient L-Lysine-Producing *Escherichia coli* Strain The transcription factor FadR which controls fatty acid metabolism of *Escherichia coli* is encoded by the fadR gene (SEQ ID NO: 15, DiRusso, C. C. et al., 1992, J. Biol. Chem., 267:8685-8691). The parent strain used for the gene disruption in this example was the WC196ΔcadAΔldc strain described in International Publication WO2006/078039. This strain is an L-lysine-producing strain of *Escherichia coli*.

Deletion of the fadR gene coding for the transcription factor controlling fatty acid metabolism was performed by the method called "Red-driven integration", first developed by Datsenko and Wanner (Datsenko, K. A. and Wanner, B. L., 2000, Proc. Natl. Acad. Sci. USA, 97:6640-6645), and an excision system derived from λ phage (Cho E. H., Gumport R. I., and Gardner J. F., 2002, J. Bacteriol., 184:5200-5203). According to the "Red-driven integration" method, using a PCR product obtained by using synthetic oligonucleotides in which a part of a target gene is designed on the 5' side, and a part of antibiotic resistance gene is designed on the 3' side, respectively, as primers, a gene-disrupted strain can be constructed in one step. By further using the excision system derived from λ phage in combination, the antibiotic resistance gene incorporated into the gene-disrupted strain can be removed (Japanese Patent Laid-open No. 2005-058227, WO2005/010175).

As the template for PCR, the plasmid pMW118-attL-kan-attR (Japanese Patent Laid-open No. 2005-058227, WO2005/010175) was used. pMW118-attL-kan-attR is a plasmid obtained by inserting the attachment sites of λ phage, the attL and attR genes, and the kan gene as an antibiotic resistance gene into pMW118 (Takara Bio), and they are inserted in the order of attL-kan-attR.

PCR was performed by using the synthetic oligonucleotides shown in SEQ ID NOS: 16 and 17 as primers, which had sequences corresponding to the both ends of the attL and attR at the 3' ends of the primers and a sequence corresponding to a part of the fadR gene as the objective gene at the 5' ends of the primers.

The amplified PCR product was purified on agarose gel, and introduced into the *Escherichia coli* WC196ΔcadAΔldcC strain containing the plasmid pKD46 having temperature sensitive replication ability by electroporation. The plasmid pKD46 (Datsenko, K. A. and Wanner, B. L., 2000, Proc. Natl. Acad. Sci. USA., 97:6640-6645) contains the DNA fragment of 2154 nucleotides in total of λ phage (GenBank/EMBL accession number J02459, 31088th to 33241st nucleotides) containing the genes coding for the Red recombinase of λRed homologous recombination system (γ, β and exo genes) controlled by the arabinose inducible ParaB promoter. The plasmid pKD46 is required in order to incorporate the PCR product into the chromosome of the WC196ΔcadAΔldcC strain.

Competent cells for electroporation were prepared as follows. That is, the *Escherichia coli* WC196 strain cultured overnight at 30° C. in the LB medium (10 g/L of tryptone, 5 g/L of yeast extract, 10 g/L of NaCl) containing 100 mg/L of ampicillin was diluted 100 times with 5 mL of the LB medium containing ampicillin (100 mg/L) and L-arabinose (1 mM). The strain was proliferated in the diluted culture at 30° C. with aeration until the OD600 reached about 0.6, then the culture was concentrated 100 times, and the cells were washed three times with 10% glycerol and thereby made ready for use in electroporation. Electroporation was performed by using 70 μL of the competent cells and about 100 ng of the PCR product. To the cells after the electroporation were added 1 mL of the SOC medium (Sambrook, J., and Russell, D. W., 2001, Molecular Cloning A Laboratory Manual/Third Edition, Cold Spring Harbor Laboratory Press, New York), and the cells were cultured at 37° C. for 1 hour, and then cultured at 37° C. on the LB agar medium containing Km (kanamycin, 40 mg/L) as plate culture to select a Km-resistant recombinant. Then, to remove the pKD46 plasmid, the recombinant was subcultured twice at 42° C. on the LB agar medium containing Km, and the ampicillin resistance of the obtained colonies was examined to obtain an ampicillin-sensitive strain from which the pKD46 was eliminated.

Deletion of the fadR gene in the mutant identified with the kanamycin-resistant gene was confirmed by PCR. The fadR-deficient strain obtained was designated WC196ΔcadAΔldcCΔfadR::att-kan strain.

Then, to remove the att-kan gene which had been introduced into the fadR gene, a helper plasmid, pMW-intxis-ts (Japanese Patent Laid-open No. 2005-058227, WO2005/010175) was used. pMW-intxis-ts is a plasmid carrying a gene coding for λ phage integrase (Int) and a gene coding for excisionase (Xis), and having temperature sensitive replication ability.

The competent cells of the WC196ΔcadAΔldcCΔfadR::att-kan strain obtained as described above were prepared in a conventional manner, transformed with the helper plasmid pMW-intxis-ts, and cultured at 30° C. on a plate of the LB agar medium containing 100 mg/L of ampicillin to select an ampicillin-resistant strain.

Then, to remove the pMW-intxis-ts plasmid, the ampicillin-resistant transformant was subcultured twice at 42° C. on the LB agar medium, ampicillin resistance and kanamycin resistance of the obtained colonies were examined to obtain a kanamycin and ampicillin-sensitive strain which was an fadR-disrupted strain from which the att-kan and pMW-intxis-ts were eliminated. This strain was designated WC196ΔcadAΔldcCΔfadR strain.

The WC196ΔcadAΔldcCΔfadR strain was transformed with the plasmid pCABD2 (WO95/16042) for lysine production carrying the dapA, dapB, lysC, and ddh genes in a conventional manner to obtain WC196ΔcadAΔldcCΔfadR/pCABD2 strain.

The strain prepared above was cultured at 37° C. in the LB medium containing 25 mg/L of streptomycin until $OD_{600}$ became about 0.6, then a 40% glycerol solution in the same volume as that of the culture medium was added to the medium, and the mixture was stirred, then divided into appropriate volumes, and stored at −80° C. as glycerol stocks.

<4-2> L-Lysine Production Culture by L-Lysine-Producing *Escherichia coli* Strain Using Fatty Acids Derived from Alga as a Carbon Source As an L-lysine-producing bacterium, the *Escherichia coli*WC196ΔcadAΔldcCΔfadR/pCABD2 strain constructed in <4-1> mentioned above (this strain is referred to as "WC196LCR/pCABD2") was used. The glycerol stock of the WC196LCR/pCABD2 strain was thawed, 100 μL of the thawed stock was uniformly applied to an L-plate containing 25 mg/L of streptomycin, and culture was performed at 37° C. for 20 hours. About 1/8 of the cells obtained from one plate were inoculated into 20 mL of the fermentation medium described below and containing 25 mg/L of streptomycin, which was contained in a Sakaguchi flask, and cultured at 37° C. for 48 hours on a reciprocally shaking culture apparatus. As the sample derived from the alga serving as the carbon source, Tween 80 was added at a concentration of 1% to the fatty acid extract derived from the alga, and the mixture was stirred, then adjusted to pH 7.0 with 1 N HCl, autoclaved at 120° C. for 20 minutes, and used as a carbon source solution. The medium composition used for the culture is shown below.

| [L-Lysine production medium for *Escherichia* bacteria] | |
|---|---|
| Reagent oleic acid or fatty acids derived from alga | 9.9 g/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 4H_2O$ | 0.01 g/L |
| Yeast extract | 2.0 g/L |
| PIPES (pH 7.0) | 20 g/L |

The medium was adjusted to pH 7.0 with KOH, and autoclaved at 110° C. for 10 minutes, provided that the carbon source, $MgSO_4 \cdot 7H_2O$, and the PIPES buffer (pH 7.0) were separately sterilized, and then mixed.

After 24 hours, the amount of L-lysine in the culture supernatant was measured with Biotech Analyzer AS310 (Sakura Seiki). The degree of the growth in this medium was determined by measuring the live cell count. Averages of the results of the culture performed in duplicate are shown in Table 2. Favorable L-lysine production was confirmed with the fatty acids derived from the alga, and the fatty acids derived from the alga provided superior L-lysine accumulation as compared with the reagent oleic acid.

TABLE 2

| Carbon source | Culture time (h) | Live cell count (×10⁸) | L-Lysine concentration (g/L) |
|---|---|---|---|
| Reagent oleic acid (9.9 g/L) + 0.6% Tween 80 | 24 | 15.2 | 2.8 |
| fatty acids derived from alga) (9.9 g/L) + 0.6% Tween 80 | 24 | 14.4 | 3.1 |

Example 5

Culture of Microalga *Chlorella Kessleri* 11H Strain

The *Chlorella kessleri* 11H strain was cultured at 30° C. and a light intensity of 7,000 lux (culture apparatus: CL-301, TOMY) for 7 days with shaking in 100 mL of the 0.2× Gamborg's B5 medium (NIHON PHARMACEUTICAL) contained in a 500 mL-volume conical flask, and the resultant culture was used as a preculture. As the light source, white light from a fluorescent lamp was used. The preculture in a volume of 6 mL was added to 300 mL of the 0.2× Gamborg's B5 medium contained in a 500 mL-volume medium bottle, and culture was performed at a culture temperature of 30° C. and a light intensity of 7,000 lux for 12 days with blowing 250 mL/minute of a mixed gas of air and 3% $CO_2$ into the medium.

| (0.2 × Gamborg's B5 medium) | |
|---|---|
| $KNO_3$ | 500 mg/L |
| $MgSO_4 \cdot 7H_2O$ | 50 mg/L |
| $NaH_2PO_4 \cdot H_2O$ | 30 mg/L |
| $CaCl_2 \cdot 2H_2O$ | 30 mg/L |
| $(NH_4)_2SO_4$ | 26.8 mg/L |
| $Na_2$-EDTA | 7.46 mg/L |
| $FeSO_4 \cdot 7H_2O$ | 5.56 mg/L |
| $MnSO_4 \cdot H_2O$ | 2 mg/L |
| $H_3BO_3$ | 0.6 mg/L |
| $ZnSO_4 \cdot 7H_2O$ | 0.4 mg/L |
| KI | 0.15 mg/L |
| $Na_2MoO_2 \cdot 2H_2O$ | 0.05 mg/L |
| $CuSO_4 \cdot 5H_2O$ | 0.005 mg/L |
| $CoCl_2 \cdot 6H_2O$ | 0.005 mg/L |

The medium was sterilized by autoclaving at 120° C. for 15 minutes.

Example 6

Temperature Condition for Mid-Temperature Processing of Alga

The culture medium obtained in Example 5 in a volume of 125 ml was put into a 500-mL volume jar fermenter (ABLE), and incubated at various temperatures and 150 rpm for 18 hours. Each obtained sample was centrifuged, and the amount of fatty acid in the obtained precipitate was measured. The measurement results are shown in FIG. 1. The fatty acid amount increased with the processing at 40° C., and markedly increased with the processing at 45° C., compared with the sample not processed.

Example 7

Culture of Microalga *Nannochloris* sp

The *Nannochloris* sp. UTEX LB 1999 strain was cultured at 30° C. and a light intensity of 7,000 lux (culture apparatus: CL-301, TOMY) for 8 days with shaking in 10 mL of the Daigo IMK medium (NIHON PHARMACEUTICAL) contained in a 50 mL-volume conical flask. As the light source, white light from a fluorescent lamp was used. As the sea water component of the Daigo IMK medium, Daigo Artificial Sea Water SP (NIHON PHARMACEUTICAL), which is artificial sea water, was used.

| (Daigo IMK medium) | |
|---|---|
| $NaNO_3$ | 200 mg/L |
| $Na_2HPO_4$ | 1.4 mg/L |
| $K_2HPO_4$ | 5 mg/L |
| $NH_4Cl$ | 2.68 mg/L |
| Fe-EDTA | 5.2 mg/L |
| Mn-EDTA | 0.332 mg/L |
| $Na_2$-EDTA | 37.2 mg/L |
| $ZnSO_4 \cdot 7H_2O$ | 0.023 mg/L |
| $CoSO_4 \cdot 7H_2O$ | 0.014 mg/L |
| $Na_2MoO_4 \cdot 2H_2O$ | 0.0073 mg/L |
| $CuSO_4 \cdot 5H_2O$ | 0.0025 mg/L |
| $H_2SeO_3$ | 0.0017 mg/L |
| Thiamin-HCl | 0.2 mg/L |
| Biotin | 0.0015 mg/L |
| Vitamin B12 | 0.0015 mg/L |
| $MnCl_2 \cdot 4H_2O$ | 0.18 mg/L |
| Daigo Artificial Sea Water SP | 36 g/L |

The medium was adjusted to pH 8.0 with 1 N NaOH, and then sterilized by autoclaving at 120° C. for 10 minutes.

Example 8

Midtemperature Processing of *Nannochloris* sp

Figure 2:
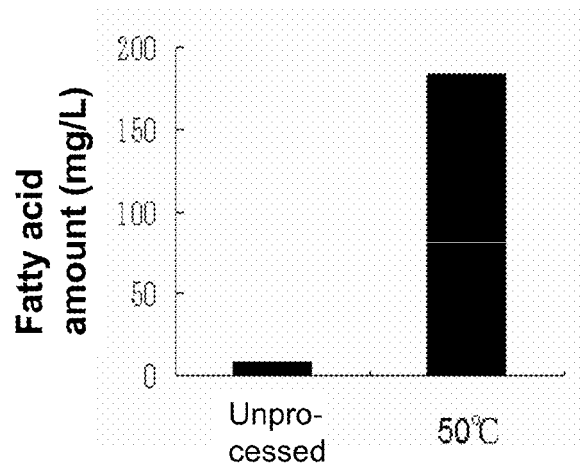
FIG. 2 shows the amount of fatty acids obtained by processing *Nannochloris* sp. at a mid-temperature.

The culture medium in a volume of 0.5 ml was put into a 1.5 ml-volume Eppendorf tube, and incubated at 50° C. and 1000 rpm for 20 hours. Each sample was centrifuged, and the amount of fatty acids in the obtained precipitate was measured. The measurement results are shown in FIG. 2. Since the amount of fatty acids markedly increased with the processing at 50° C. compared with no processing, it was confirmed that fatty acids were generated also in *Nannochloris* sp. by the moderate temperature processing.

Example 9

Culture of Microalga *Chlorella kessleri* 11H Strain

The *Chlorella kessleri* 11H strain was cultured at 30° C. and a light intensity of 7,000 lux (culture apparatus: CL-301, TOMY) for 7 days in 300 mL of the 0.2× Gamborg's B5 medium (NIHON PHARMACEUTICAL) contained in a 500 mL-volume medium bottle with blowing 250 mL/minute of a mixed gas of air and 3% $CO_2$ into the medium, and the resultant culture was used as a preculture. As the light source, white light from a fluorescent lamp was used. The preculture in a volume of 6 mL was added to 300 mL of the 0.2× Gamborg's B5 medium contained in a 500 mL-volume medium bottle, and culture was performed at a culture temperature of 30° C. and a light intensity of 7,000 lux for 12 days with blowing 250 mL/minute of a mixed gas of air and 3% $CO_2$ into the medium.

| (0.2 × Gamborg's B5 medium) | |
| --- | --- |
| $KNO_3$ | 500 mg/L |
| $MgSO_4 \cdot 7H_2O$ | 50 mg/L |
| $NaH_2PO_4 \cdot H_2O$ | 30 mg/L |
| $CaCl_2 \cdot 2H_2O$ | 30 mg/L |
| $(NH_4)_2SO_4$ | 26.8 mg/L |
| $Na_2$-EDTA | 7.46 mg/L |
| $FeSO_4 \cdot 7H_2O$ | 5.56 mg/L |
| $MnSO_4 \cdot H_2O$ | 2 mg/L |
| $H_3BO_3$ | 0.6 mg/L |
| $ZnSO_4 \cdot 7H_2O$ | 0.4 mg/L |
| KI | 0.15 mg/L |
| $Na_2MoO_2 \cdot 2H_2O$ | 0.05 mg/L |
| $CuSO_4 \cdot 5H_2O$ | 0.005 mg/L |
| $CoCl_2 \cdot 6H_2O$ | 0.005 mg/L |

The medium was sterilized by autoclaving at 120° C. for 15 minutes.

Example 10

Figure 3:
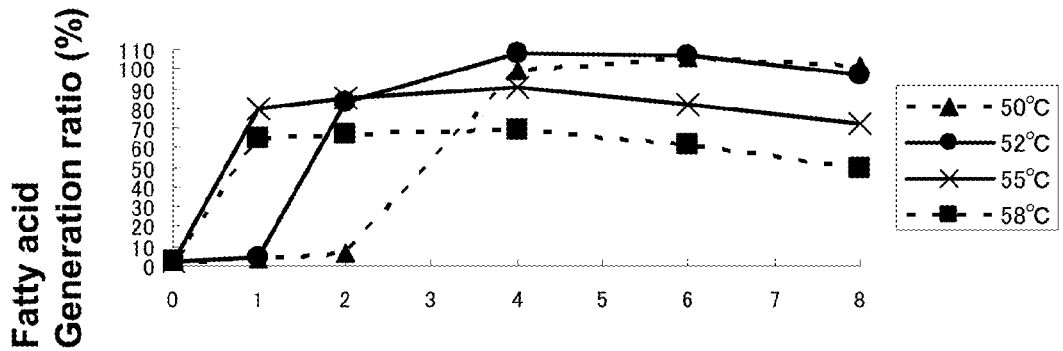
FIG. 3 shows the time course of the fatty acid generation ratio during a processing of an alga at a mid-temperature.

Time Course of Fatty Acid Generation rate in Midtemperature Processing of Algae at Various Temperatures The culture medium obtained in Example 9 was adjusted to pH 4.5 with 1 N HCl, and 1 ml of the medium was put into a 1.5 ml-volume Eppendorf tube, and incubated at various temperatures and 1000 rpm for various times. Each obtained sample was centrifuged, and the amount of fatty acid in the obtained precipitate was measured. The measurement results are shown in FIG. 3. The relative fatty acid production rate was calculated as the rate to the amount of fatty acids produced when oils and fats extracted from the untreated alga bodies with an organic solvent were completely decomposed, which was taken as 100. The fatty acid amount increased after 1 hour at a temperature of 55° C. or higher, and it markedly increased after 4 to 6 hours at a temperature of 50 to 52° C.

Example 11 pH Condition of Alkali Treatment for Fatty Acid Extraction

Figure 4:
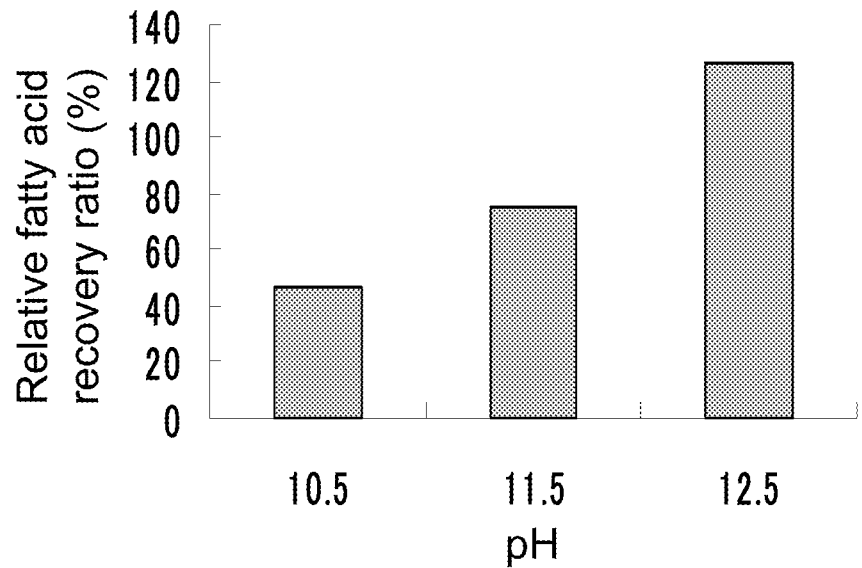
FIG. 4 shows the results of examination of the pH conditions for an alkali treatment for extracting fatty acids.

The culture medium obtained in Example 9 was centrifuged, and the culture supernatant was added to the precipitate to prepare a 20-fold concentrate of the medium. The concentrate was adjusted to pH 4.5 with 1 N HCl, and 1 ml of the concentrate was put into a 1.5 ml-volume Eppendorf tube, and incubated at 52° C. and 1000 rpm for 14 hours. The obtained sample was adjusted to various pH values with 3 N NaOH, and extracted at 90° C. and 1000 rpm for 3 hours, and the amount of fatty acid in each sample was measured. The measurement results are shown in FIG. 4. The relative fatty acid collection rate was calculated as the rate to the amount of fatty acids produced when oils and fats extracted from the untreated alga bodies with an organic solvent were completely decomposed, which was taken as 100. The fatty acids were slightly extracted at pH 10.5, and the extracted fatty acid amount increased at pH 11.5, and markedly increased at pH 12.5.

Example 12

Temperature Condition of Alkali Treatment for Fatty Acid Extraction

Figure 5:
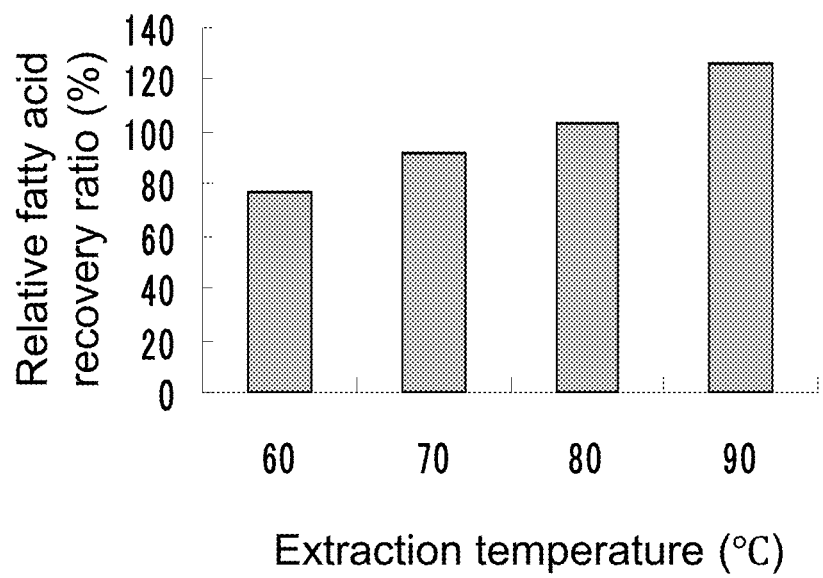
FIG. 5 shows the results of examination of the temperature conditions for an alkali treatment for extracting fatty acids.

The culture medium obtained in Example 9 was centrifuged, and the culture supernatant was added to the precipitate to prepare a 20-fold concentrate of the medium. The concentrate was adjusted to pH 4.5 with 1 N HCl, and 1 ml of the concentrate was put into a 1.5 ml-volume Eppendorf tube, and incubated at 52° C. and 1000 rpm for 14 hours. The obtained sample was adjusted to pH 12.5 with 3 N NaOH, and extracted at various temperatures and 1000 rpm for 3 hours, and the amount of fatty acid in each sample was measured. The measurement results are shown in FIG. 5. The relative fatty acid collection rate was calculated as the rate to the amount of fatty acids produced when oils and fats extracted from the untreated alga bodies with an organic solvent were completely decomposed, which was taken as 100. Extraction of the fatty acids was confirmed at 60° C., and the fatty acid amount increased with increase of the temperature, and reached the maximum at 90° C.

Example 13

Time of Alkali Treatment for Fatty Acid Extraction

Figure 6:
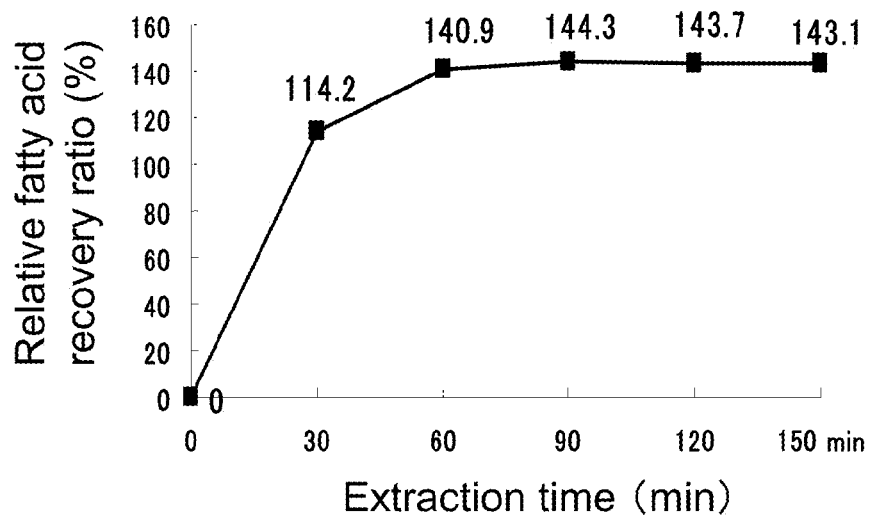
FIG. 6 shows the results of examination of time for an alkali treatment for extracting fatty acids.

The culture medium obtained in Example 9 was centrifuged, and the culture supernatant was added to the precipitate to prepare a 20-fold concentrate of the medium. The concentrate was adjusted to pH 4.5 with 1 N HCl, and 1 ml of the concentrate was put into a 1.5 ml-volume Eppendorf tube, and incubated at 52° C. and 1000 rpm for 14 hours. The obtained sample was adjusted to pH 12.5 with 3 N NaOH, and extracted at 90° C. and 1000 rpm for various times, and the amount of fatty acid in each sample was measured. The measurement results are shown in FIG. 6. The relative fatty acid collection rate was calculated as the rate to the amount of fatty acids produced when oils and fats extracted from the untreated alga bodies with an organic solvent were completely decomposed, which was taken as 100. The fatty acid amount increased with the treatment for 30 minutes, and markedly increased as the processing time became longer, i.e., the processing time was extended to 60 minutes and 90 minutes. After 120 minutes, the fatty acid amount did not further increase.

Example 14

Culture of Microalga *Chlorella kessleri* 11H Strain

The *Chlorella kessleri* 11H strain was cultured at 30° C. and a light intensity of 7,000 lux (culture apparatus: CL-301, TOMY) for 7 days in 400 mL of the 0.2× Gamborg's B5 medium (NIHON PHARMACEUTICAL) contained in a 500 mL-volume medium bottle with blowing 250 mL/minute of a mixed gas of air and 3% $CO_2$ into the medium, and the resultant culture was used as a preculture. As the light source, white light from a fluorescent lamp was used. The preculture in a volume of 8 mL was added to 400 mL of the 0.2× Gamborg's B5 medium contained in a 500 mL-volume medium bottle, and culture was performed at a culture temperature of 30° C. and a light intensity of 7,000 lux for 12 days with blowing 250 mL/minute of a mixed gas of air and 3% $CO_2$ into the medium.

| (0.2 x Gamborg's B5 medium) | |
|---|---|
| $KNO_3$ | 500 mg/L |
| $MgSO_4 \cdot 7H_2O$ | 50 mg/L |
| $NaH_2PO_4 \cdot H_2O$ | 30 mg/L |
| $CaCl_2 \cdot 2H_2O$ | 30 mg/L |
| $(NH_4)_2SO_4$ | 26.8 mg/L |
| $Na_2$-EDTA | 7.46 mg/L |
| $FeSO_4 \cdot 7H_2O$ | 5.56 mg/L |
| $MnSO_4 \cdot H_2O$ | 2 mg/L |
| $H_3BO_3$ | 0.6 mg/L |
| $ZnSO_4 \cdot 7H_2O$ | 0.4 mg/L |
| KI | 0.15 mg/L |
| $Na_2MoO_2 \cdot 2H_2O$ | 0.05 mg/L |
| $CuSO_4 \cdot 5H_2O$ | 0.005 mg/L |
| $CoCl_2 \cdot 6H_2O$ | 0.005 mg/L |

The medium was sterilized by autoclaving at 120° C. for 15 minutes.

Example 15

Figure 7:
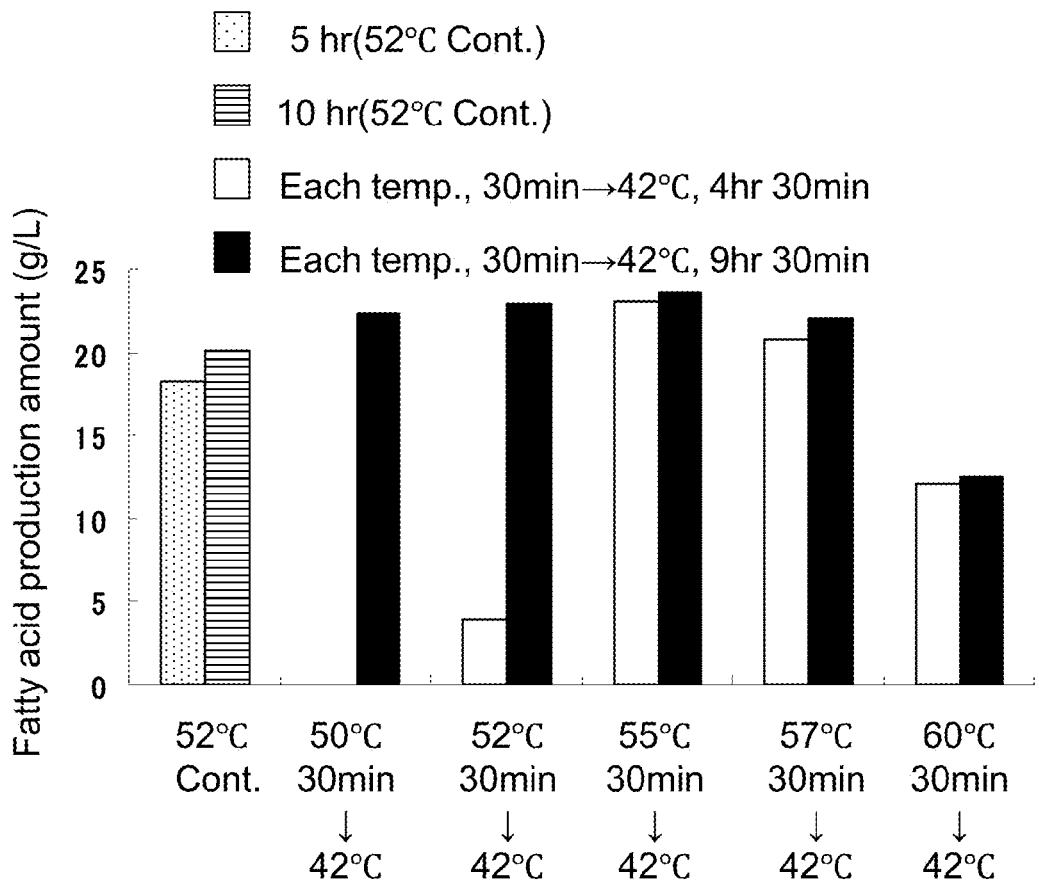
FIG. 7 shows the results of examination of the temperature conditions for first step of a two-step processing of algae at a mid-temperature.

Examination of Temperature Condition for First Step Processing in Two-Step Midtemperature Processing of Algae The culture medium obtained in Example 14 was centrifuged, and sterilized water was added to the precipitate to prepare a 40-fold concentrate of the medium. The concentrate was adjusted to pH 4.5 with 3 N HCl, and 500 µl of the concentrate was put into a 1.5 ml-volume Eppendorf tube, and preincubated with standing at 50, 52, 55, 57 or 60° C. for 5 minutes. Then, each sample was incubated at the same temperature as the above temperature and 1000 rpm for 30 minutes, and then incubated at 42° C. and 1000 rpm for 4 hours and 30 minutes or 9 hours and 30 minutes to hydrolyze oils and fats. Each obtained sample was centrifuged, and the amount of fatty acid in the precipitate was measured. The measurement results are shown in FIG. 7. It was confirmed that production of fatty acids was scarcely confirmed in the samples obtained with induction at 50 or 52° C. for 30 minutes and the subsequent incubation at 42° C. for 4 hours and 30 minutes as compared with the sample obtained with the continuous processing at 52° C., whereas the production amount of fatty acids in the sample obtained with the incubation at 42° C. for 9 hours and 30 minutes after the induction exceeded that observed in the sample obtained with the continuous processing at 52° C. Further, when the sample was subjected to induction at a temperature of 55° C. or higher for 30 minutes and then processed at 42° C., production of fatty acids was first confirmed after 4 hours and 30 minutes, and the fatty acid production amount increased with decrease of the induction temperature.

Example 16

Figure 8:
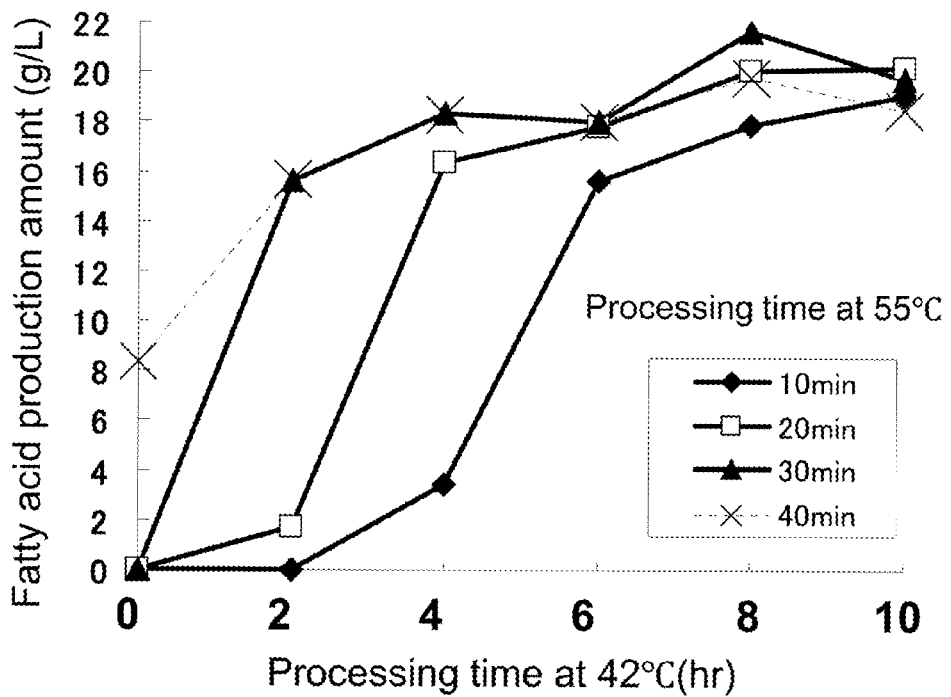
FIG. 8 shows the results of examination of time for first step and time for second step of a two-step processing of algae at a mid-temperature.

Examination of Time for First Step Processing and Time for Second Step Processing in Two-Step Mid-Temperature Processing of Algae The culture medium obtained in Example 14 was centrifuged, and sterilized water was added to the precipitate to prepare a 40-fold concentrate of the medium. The concentrate was adjusted to pH 4.5 with 3 N HCl, and 600 µl of the concentrate was put into a 1.5 ml-volume Eppendorf tube, and preincubated with standing at 55° C. for 5 minutes. Then, each sample was incubated at 55° C. and 1000 rpm for 30 minutes, and then incubated at 42° C. and 1000 rpm for various times to hydrolyze oils and fats. Each obtained sample was centrifuged, and the amount of fatty acid in the precipitate was measured. The measurement results are shown in FIG. 8. With the induction at 55° C. for 10 minutes or 20 minutes, the production amount of fatty acids increased after 4 hours and 6 hours, respectively. On the other hand, with the induction at 55° C. for 30 minutes, the production amount of fatty acids increased after 2 hours, and reached the maximum after 8 hours.

Example 17

Culture of Microalga *Chlorella kessleri* 11H Strain

The *Chlorella kessleri* 11H strain was cultured at 30° C. and a light intensity of 7,000 lux (culture apparatus: CL-301, TOMY) for 7 days in 800 mL of the 0.2× Gamborg's B5 medium (NIHON PHARMACEUTICAL) contained in a 1000 mL-volume medium bottle with blowing 400 mL/minute of a mixed gas of air and 3% $CO_2$ into the medium, and the resultant culture was used as a preculture. As the light source, white light from a fluorescent lamp was used. The preculture in a volume of 16 mL was added to 800 mL of the 0.2× Gamborg's B5 medium contained in a 1000 mL-volume medium bottle, and culture was performed at a culture temperature of 30° C. and a light intensity of 7,000 lux for 14 days with blowing 400 mL/minute of a mixed gas of air and 3% $CO_2$ into the medium.

| (0.2 x Gamborg's B5 medium) | |
|---|---|
| $KNO_3$ | 500 mg/L |
| $MgSO_4 \cdot 7H_2O$ | 50 mg/L |
| $NaH_2PO_4 \cdot H_2O$ | 30 mg/L |
| $CaCl_2 \cdot 2H_2O$ | 30 mg/L |
| $(NH_4)_2SO_4$ | 26.8 mg/L |
| $Na_2$-EDTA | 7.46 mg/L |
| $FeSO_4 \cdot 7H_2O$ | 5.56 mg/L |
| $MnSO_4 \cdot H_2O$ | 2 mg/L |
| $H_3BO_3$ | 0.6 mg/L |
| $ZnSO_4 \cdot 7H_2O$ | 0.4 mg/L |
| KI | 0.15 mg/L |
| $Na_2MoO_2 \cdot 2H_2O$ | 0.05 mg/L |

(0.2 x Gamborg's B5 medium)

| | |
|---|---|
| $CuSO_4 \cdot 5H_2O$ | 0.005 mg/L |
| $CoCl_2 \cdot 6H_2O$ | 0.005 mg/L |

The medium was sterilized by autoclaving at 120° C. for 15 minutes.

Example 18

Figure 9:
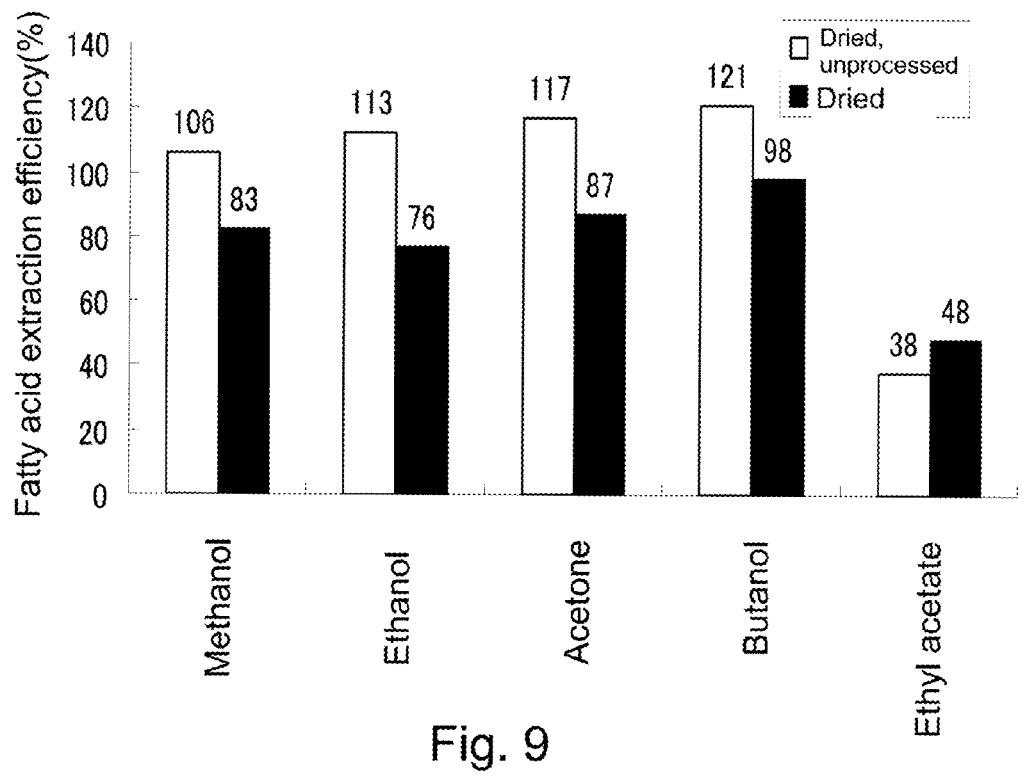
FIG. 9 shows the results of examination of the solvent used for an organic solvent treatment for extracting fatty acids.

Examination of Solvent Used for Organic Solvent Treatment for Fatty Acid Extraction The culture medium obtained in Example 17 was centrifuged, and sterilized water was added to the precipitate to prepare a 40-fold concentrate of the medium. The concentrate was adjusted to pH 4.5 with 3 N HCl, and 600 μl of the concentrate was put into a 1.5 ml-volume Eppendorf tube, preincubated with standing at 55° C. for 5 minutes, and incubated at the same temperature and 1000 rpm for 30 minutes and at 42° C. and 1000 rpm for 12 hours to hydrolyze oils and fats. The obtained sample in a volume of 250 μl was centrifuged, and the precipitate was dried at 65° C. for 50 minutes in a centrifugal evaporator to prepare a dried sample. To the dried sample or dried unprocessed sample, 500 μl of each solvent was added. Each sample was extracted at 45° C. and 1000 rpm for 30 minutes, and fatty acid amount in each sample was measured. The measurement results are shown in FIG. 9. The fatty acid extraction efficiency was calculated as a relative value to the fatty acid amount obtained by centrifuging 25 μl of the mid-temperature-processed product, suspending the precipitate in 200 μl of 1% NaCl aqueous solution, and extracting fatty acids in a bead-type cell disruption tube containing 400 μl each of methanol and chloroform, which was taken as 100. When the dried unprocessed sample was extracted with methanol, ethanol, acetone or butanol, high fatty acid extraction efficiency was obtained. On the other hand, when the dried sample was extracted with each solvent, the extraction efficiency decreased. Moreover, with ethyl acetate, the extraction efficiency decreased for the dried sample and the dried unprocessed sample.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid, which comprises:
   (a) preparing a processed product of a microalga, which promotes production and accumulation of the L-amino acid by a bacterium having an ability to produce the L-amino acid, comprising:
      (i) culturing the microalga in a first medium, followed by
      (ii) incubating the cultured microalga of step (i) at a mid-temperature of 40° C. to 70° C., and
      (iii) performing centrifugation on the product of step (ii), resulting in a precipitate and supernatant; and
   (b) culturing the bacterium in a second medium comprising the supernatant of step (iii) to produce and accumulate the L-amino acid in the second medium, wherein the supernatant comprises glucose or glycerol; and
   (c) collecting the L-amino acid from the second medium.

2. The method according to claim 1, wherein temperature is lowered the incubating of step (ii).

3. The method according to claim 1, wherein the microalga is an alga belonging to the division Chlorophyta or Heterokontophyta.

4. The method according to claim 3, wherein the microalga is an alga belonging to the class Chlorophyceae, Trebouxiophyceae, or Bacillariophyceae.

5. The method according to claim 4, wherein the microalga is an alga belonging to the class Chlorophyceae.

6. The method according to claim 1, wherein the bacterium belongs to the family Enterobacteriaceae or a coryneform bacterium.

7. The method according to claim 6, wherein the bacterium belonging to the family Enterobacteriaceae is *Escherichia coli*.

* * * * *

SEQUENCE LISTING

```
<160> NUMBER OF SEQ ID NOS: 19

<210> SEQ ID NO 1
<211> LENGTH: 639
<212> TYPE: DNA
<213> ORGANISM: Bacillus subtilis
<220> FEATURE:
<221> NAME/KEY: CDS
<222> LOCATION: (1)..(639)

<400> SEQUENCE: 1 atg aaa ttt gta aaa aga agg atc att gca ctt gta aca att ttg atg      48
Met Lys Phe Val Lys Arg Arg Ile Ile Ala Leu Val Thr Ile Leu Met
1               5                   10                  15 ctg tct gtt aca tcg ctg ttt gcg ttg cag ccg tca gca aaa gcc gct      96
Leu Ser Val Thr Ser Leu Phe Ala Leu Gln Pro Ser Ala Lys Ala Ala
            20                  25                  30 gaa cac aat cca gtc gtt atg gtt cac ggt att gga ggg gca tca ttc     144
Glu His Asn Pro Val Val Met Val His Gly Ile Gly Gly Ala Ser Phe
        35                  40                  45 aat ttt gcg gga att aag agc tat ctc gta tct cag ggc tgg tcg cgg     192
Asn Phe Ala Gly Ile Lys Ser Tyr Leu Val Ser Gln Gly Trp Ser Arg
    50                  55                  60 gac aag ctg tat gca gtt gat ttt tgg gac aag aca ggc aca aat tat     240
Asp Lys Leu Tyr Ala Val Asp Phe Trp Asp Lys Thr Gly Thr Asn Tyr
65                  70                  75                  80 aac aat gga ccg gta tta tca cga ttt gtg caa aag gtt tta gat gaa     288
Asn Asn Gly Pro Val Leu Ser Arg Phe Val Gln Lys Val Leu Asp Glu
                85                  90                  95 acg ggt gcg aaa aaa gtg gat att gtc gct cac agc atg ggg ggc gcg     336
Thr Gly Ala Lys Lys Val Asp Ile Val Ala His Ser Met Gly Gly Ala
            100                 105                 110 aac aca ctt tac tac ata aaa aat ctg gac ggc gga aat aaa gtt gca     384
Asn Thr Leu Tyr Tyr Ile Lys Asn Leu Asp Gly Gly Asn Lys Val Ala
        115                 120                 125
```

```
aac gtc gtg acg gtt ggc ggc gcg aac cgt ttg acg aca ggc aag gcg       432
Asn Val Val Thr Val Gly Gly Ala Asn Arg Leu Thr Thr Gly Lys Ala
    130                 135                 140 ctt ccg gga aca gat cca aat caa aag att tta tac aca tcc att tac       480
Leu Pro Gly Thr Asp Pro Asn Gln Lys Ile Leu Tyr Thr Ser Ile Tyr
145                 150                 155                 160 agc agt gcc gat atg att gtc atg aat tac tta tca aga tta gat ggt       528
Ser Ser Ala Asp Met Ile Val Met Asn Tyr Leu Ser Arg Leu Asp Gly
                165                 170                 175 gct aga aac gtt caa atc cat ggc gtt gga cac atc ggc ctt ctg tac       576
Ala Arg Asn Val Gln Ile His Gly Val Gly His Ile Gly Leu Leu Tyr
            180                 185                 190 agc agc caa gtc aac agc ctg att aaa gaa ggg ctg aac ggg ggc           624
Ser Ser Gln Val Asn Ser Leu Ile Lys Glu Gly Leu Asn Gly Gly
        195                 200                 205 cag aat acg aat taa                                                   639
Gln Asn Thr Asn
    210
```

```
<210> SEQ ID NO 2
<211> LENGTH: 212
<212> TYPE: PRT
<213> ORGANISM: Bacillus subtilis

<400> SEQUENCE: 2

Met Lys Phe Val Lys Arg Arg Ile Ile Ala Leu Val Thr Ile Leu Met
1               5                   10                  15

Leu Ser Val Thr Ser Leu Phe Ala Leu Gln Pro Ser Ala Lys Ala Ala
            20                  25                  30

Glu His Asn Pro Val Val Met Val His Gly Ile Gly Gly Ala Ser Phe
        35                  40                  45

Asn Phe Ala Gly Ile Lys Ser Tyr Leu Val Ser Gln Gly Trp Ser Arg
    50                  55                  60

Asp Lys Leu Tyr Ala Val Asp Phe Trp Asp Lys Thr Gly Thr Asn Tyr
65                  70                  75                  80

Asn Asn Gly Pro Val Leu Ser Arg Phe Val Gln Lys Val Leu Asp Glu
                85                  90                  95

Thr Gly Ala Lys Lys Val Asp Ile Val Ala His Ser Met Gly Gly Ala
            100                 105                 110

Asn Thr Leu Tyr Tyr Ile Lys Asn Leu Asp Gly Gly Asn Lys Val Ala
        115                 120                 125

Asn Val Val Thr Val Gly Gly Ala Asn Arg Leu Thr Thr Gly Lys Ala
    130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Arg Leu Asp Gly
                165                 170                 175

Ala Arg Asn Val Gln Ile His Gly Val Gly His Ile Gly Leu Leu Tyr
            180                 185                 190

Ser Ser Gln Val Asn Ser Leu Ile Lys Glu Gly Leu Asn Gly Gly Gly
        195                 200                 205

Gln Asn Thr Asn
    210

<210> SEQ ID NO 3
<211> LENGTH: 1077
<212> TYPE: DNA
<213> ORGANISM: Burkholderia glumae
```

```
<220> FEATURE:
<221> NAME/KEY: CDS
<222> LOCATION: (1)..(1077)

<400> SEQUENCE: 3 atg gtc aga tcg atg cgt tcc agg gtg gcg gcg agg gcg gtg gca tgg        48
Met Val Arg Ser Met Arg Ser Arg Val Ala Ala Arg Ala Val Ala Trp
1               5                   10                  15 gcg ttg gcg gtg atg ccg ctg gcc ggc gcg gcc ggg ttg acg atg gcc        96
Ala Leu Ala Val Met Pro Leu Ala Gly Ala Ala Gly Leu Thr Met Ala
            20                  25                  30 gcg tcg ccc gcg gcc gtc gcg gcg gac acc tac gcg gcg acg cgc tat       144
Ala Ser Pro Ala Ala Val Ala Ala Asp Thr Tyr Ala Ala Thr Arg Tyr
        35                  40                  45 ccg gtg atc ctc gtc cac ggc ctc gcg ggc acc gac aag ttc gcg aac       192
Pro Val Ile Leu Val His Gly Leu Ala Gly Thr Asp Lys Phe Ala Asn
    50                  55                  60 gtg gtg gac tat tgg tac gga atc cag agc gat ctg caa tcg cat ggc       240
Val Val Asp Tyr Trp Tyr Gly Ile Gln Ser Asp Leu Gln Ser His Gly
65                  70                  75                  80 gcg aag gtg tac gtc gcg aat ctc tcg gga ttc cag agc gac gac ggg       288
Ala Lys Val Tyr Val Ala Asn Leu Ser Gly Phe Gln Ser Asp Asp Gly
                85                  90                  95 ccg aac ggc cgc ggc gag cag ctg ctc gcc tac gtg aag cag gtg ctc       336
Pro Asn Gly Arg Gly Glu Gln Leu Leu Ala Tyr Val Lys Gln Val Leu
            100                 105                 110 gcg gcc acc ggc gcg acc aag gtg aac ctg atc ggc cac agc cag ggc       384
Ala Ala Thr Gly Ala Thr Lys Val Asn Leu Ile Gly His Ser Gln Gly
        115                 120                 125 ggc ctg acc tcg cgc tac gtc gcg gcc gtc gcg ccg caa ctg gtg gcc       432
Gly Leu Thr Ser Arg Tyr Val Ala Ala Val Ala Pro Gln Leu Val Ala
    130                 135                 140 tcg gtg acg acg atc ggc acg ccg cat cgc ggc tcc gag ttc gcc gac       480
Ser Val Thr Thr Ile Gly Thr Pro His Arg Gly Ser Glu Phe Ala Asp
145                 150                 155                 160 ttc gtg cag gac gtg ctg aag acc gat ccg acc ggg ctc tcg tcg acg       528
Phe Val Gln Asp Val Leu Lys Thr Asp Pro Thr Gly Leu Ser Ser Thr
                165                 170                 175 gtg atc gcc gcc ttc gtc aac gtg ttc ggc acg ctc gtc agc agc tcg       576
Val Ile Ala Ala Phe Val Asn Val Phe Gly Thr Leu Val Ser Ser Ser
            180                 185                 190 cac aac acc gac cag gac gcg ctc gcg gcg ctg cgc acg ctc acc acc       624
His Asn Thr Asp Gln Asp Ala Leu Ala Ala Leu Arg Thr Leu Thr Thr
        195                 200                 205 gcg cag acc gcc acc tac aac cgg aac ttc ccg agc gcg ggc ctg ggc       672
Ala Gln Thr Ala Thr Tyr Asn Arg Asn Phe Pro Ser Ala Gly Leu Gly
    210                 215                 220 gcg ccc ggt tcg tgc cag acg ggc gcc gcg acc gaa acc gtc ggc ggc       720
Ala Pro Gly Ser Cys Gln Thr Gly Ala Ala Thr Glu Thr Val Gly Gly
225                 230                 235                 240 agc cag cac ctg ctc tat tcg tgg ggc ggc acc gcg atc cag ccc acc       768
Ser Gln His Leu Leu Tyr Ser Trp Gly Gly Thr Ala Ile Gln Pro Thr
                245                 250                 255 tcc acc gtg ctc ggc gtg acc ggc gcg acc gac acc agc acc ggc acg       816
Ser Thr Val Leu Gly Val Thr Gly Ala Thr Asp Thr Ser Thr Gly Thr
            260                 265                 270 ctc gac gtc gcg aac gtg acc gac ccg tcc acg ctc gcg ctg ctc gcc       864
Leu Asp Val Ala Asn Val Thr Asp Pro Ser Thr Leu Ala Leu Leu Ala
        275                 280                 285
```

| | | |
|---|---|---|
| acc ggc gcg gtg atg atc aat cgc gcc tcg ggg cag aac gac ggg ctc<br>Thr Gly Ala Val Met Ile Asn Arg Ala Ser Gly Gln Asn Asp Gly Leu<br>290                         295                   300 | | 912 |
| gtc tcg cgc tgc agc tcg ctg ttc ggg cag gtg atc agc acc agc tac<br>Val Ser Arg Cys Ser Ser Leu Phe Gly Gln Val Ile Ser Thr Ser Tyr<br>305                       310                   315             320 | | 960 |
| cac tgg aac cat ctc gac gag atc aac cag ctg ctc ggc gtg cgc ggc<br>His Trp Asn His Leu Asp Glu Ile Asn Gln Leu Leu Gly Val Arg Gly<br>                 325                   330                   335 | | 1008 |
| gcc aac gcg gaa gat ccg gtc gcg gtg atc cgc acg cac gtg aac cgg<br>Ala Asn Ala Glu Asp Pro Val Ala Val Ile Arg Thr His Val Asn Arg<br>             340                   345                   350 | | 1056 |
| ctc aag ctg cag ggc gtg tga<br>Leu Lys Leu Gln Gly Val<br>             355 | | 1077 |

<210> SEQ ID NO 4
<211> LENGTH: 358
<212> TYPE: PRT
<213> ORGANISM: Burkholderia glumae

<400> SEQUENCE: 4

Met Val Arg Ser Met Arg Ser Arg Val Ala Ala Arg Ala Val Ala Trp
1                   5                  10                 15

Ala Leu Ala Val Met Pro Leu Ala Gly Ala Ala Gly Leu Thr Met Ala
                 20                  25                 30

Ala Ser Pro Ala Ala Val Ala Ala Asp Thr Tyr Ala Ala Thr Arg Tyr
            35                   40                   45

Pro Val Ile Leu Val His Gly Leu Ala Gly Thr Asp Lys Phe Ala Asn
    50                   55                   60

Val Val Asp Tyr Trp Tyr Gly Ile Gln Ser Asp Leu Gln Ser His Gly
65                  70                  75                 80

Ala Lys Val Tyr Val Ala Asn Leu Ser Gly Phe Gln Ser Asp Asp Gly
                 85                  90                 95

Pro Asn Gly Arg Gly Glu Gln Leu Leu Ala Tyr Val Lys Gln Val Leu
            100                  105                 110

Ala Ala Thr Gly Ala Thr Lys Val Asn Leu Ile Gly His Ser Gln Gly
        115                  120                 125

Gly Leu Thr Ser Arg Tyr Val Ala Ala Val Ala Pro Gln Leu Val Ala
    130                   135                  140

Ser Val Thr Thr Ile Gly Thr Pro His Arg Gly Ser Glu Phe Ala Asp
145                 150                 155              160

Phe Val Gln Asp Val Leu Lys Thr Asp Pro Thr Gly Leu Ser Ser Thr
                 165                 170               175

Val Ile Ala Ala Phe Val Asn Val Phe Gly Thr Leu Val Ser Ser Ser
        180                  185                 190

His Asn Thr Asp Gln Asp Ala Leu Ala Ala Leu Arg Thr Leu Thr Thr
    195                   200                  205

Ala Gln Thr Ala Thr Tyr Asn Arg Asn Phe Pro Ser Ala Gly Leu Gly
    210                 215                  220

Ala Pro Gly Ser Cys Gln Thr Gly Ala Ala Thr Glu Thr Val Gly Gly
225                 230                 235              240

Ser Gln His Leu Leu Tyr Ser Trp Gly Gly Thr Ala Ile Gln Pro Thr
                 245                 250               255

Ser Thr Val Leu Gly Val Thr Gly Ala Thr Asp Thr Ser Thr Gly Thr
        260                  265                 270

```
Leu Asp Val Ala Asn Val Thr Asp Pro Ser Thr Leu Ala Leu Leu Ala
            275                 280                 285

Thr Gly Ala Val Met Ile Asn Arg Ala Ser Gly Gln Asn Asp Gly Leu
        290                 295                 300

Val Ser Arg Cys Ser Ser Leu Phe Gly Gln Val Ile Ser Thr Ser Tyr
305                 310                 315                 320

His Trp Asn His Leu Asp Glu Ile Asn Gln Leu Leu Gly Val Arg Gly
                325                 330                 335

Ala Asn Ala Glu Asp Pro Val Ala Val Ile Arg Thr His Val Asn Arg
            340                 345                 350

Leu Lys Leu Gln Gly Val
        355

<210> SEQ ID NO 5
<211> LENGTH: 936
<212> TYPE: DNA
<213> ORGANISM: Pseudomonas aeruginosa
<220> FEATURE:
<221> NAME/KEY: CDS
<222> LOCATION: (1)..(936)

<400> SEQUENCE: 5
```

| | | | | | | | | | | | | | | | | |
|---|---|---|---|---|---|---|---|---|---|---|---|---|---|---|---|---|
| atg | aag | aag | aag | tct | ctg | ctc | ccc | ctc | ggc | ctg | gcc | atc | ggc | ctc | gcc | 48 |
| Met | Lys | Lys | Lys | Ser | Leu | Leu | Pro | Leu | Gly | Leu | Ala | Ile | Gly | Leu | Ala | |
| 1 | | | | 5 | | | | | 10 | | | | | 15 | | |
| tct | ctc | gct | gcc | agc | cct | ctg | atc | cag | gcc | agc | acc | tac | acc | cag | acc | 96 |
| Ser | Leu | Ala | Ala | Ser | Pro | Leu | Ile | Gln | Ala | Ser | Thr | Tyr | Thr | Gln | Thr | |
| | | | 20 | | | | | 25 | | | | | 30 | | | |
| aaa | tac | ccc | atc | gtg | ctg | gcc | cac | ggc | atg | ctc | ggc | ttc | gac | aac | atc | 144 |
| Lys | Tyr | Pro | Ile | Val | Leu | Ala | His | Gly | Met | Leu | Gly | Phe | Asp | Asn | Ile | |
| | | 35 | | | | | 40 | | | | | 45 | | | | |
| ctc | ggg | gtc | gac | tac | tgg | ttc | ggc | att | ccc | agc | gcc | ttg | cgc | cgt | gac | 192 |
| Leu | Gly | Val | Asp | Tyr | Trp | Phe | Gly | Ile | Pro | Ser | Ala | Leu | Arg | Arg | Asp | |
| | 50 | | | | | 55 | | | | | 60 | | | | | |
| ggt | gcc | cag | gtc | tac | gtc | acc | gaa | gtc | agc | cag | ttg | gac | acc | tcg | gaa | 240 |
| Gly | Ala | Gln | Val | Tyr | Val | Thr | Glu | Val | Ser | Gln | Leu | Asp | Thr | Ser | Glu | |
| 65 | | | | | 70 | | | | | 75 | | | | | 80 | |
| gtc | cgc | ggc | gag | cag | ttg | ctg | caa | cag | gtg | gag | gaa | atc | gtc | gcc | ctc | 288 |
| Val | Arg | Gly | Glu | Gln | Leu | Leu | Gln | Gln | Val | Glu | Glu | Ile | Val | Ala | Leu | |
| | | | | 85 | | | | | 90 | | | | | 95 | | |
| agc | ggc | cag | ccc | aag | gtc | aac | ctg | atc | ggc | cac | agc | cac | ggc | ggg | ccg | 336 |
| Ser | Gly | Gln | Pro | Lys | Val | Asn | Leu | Ile | Gly | His | Ser | His | Gly | Gly | Pro | |
| | | | 100 | | | | | 105 | | | | | 110 | | | |
| acc | atc | cgc | tac | gtc | gcc | gcc | gta | cgt | ccc | gac | ctg | atc | gct | tcc | gcc | 384 |
| Thr | Ile | Arg | Tyr | Val | Ala | Ala | Val | Arg | Pro | Asp | Leu | Ile | Ala | Ser | Ala | |
| | | 115 | | | | | 120 | | | | | 125 | | | | |
| acc | agc | gtc | ggc | gcc | ccg | cac | aag | ggt | tcg | gac | acc | gcc | gac | ttc | ctg | 432 |
| Thr | Ser | Val | Gly | Ala | Pro | His | Lys | Gly | Ser | Asp | Thr | Ala | Asp | Phe | Leu | |
| | 130 | | | | | 135 | | | | | 140 | | | | | |
| cgc | cag | atc | cca | ccg | ggt | tcg | gcc | ggc | gag | gca | atc | ctc | tcc | ggg | ctg | 480 |
| Arg | Gln | Ile | Pro | Pro | Gly | Ser | Ala | Gly | Glu | Ala | Ile | Leu | Ser | Gly | Leu | |
| 145 | | | | | 150 | | | | | 155 | | | | | 160 | |
| gtc | aac | agc | ctc | ggc | gcg | ctg | atc | agc | ttc | ctt | tcc | agc | ggc | agc | acc | 528 |
| Val | Asn | Ser | Leu | Gly | Ala | Leu | Ile | Ser | Phe | Leu | Ser | Ser | Gly | Ser | Thr | |
| | | | | 165 | | | | | 170 | | | | | 175 | | |
| ggt | acg | cag | aat | tca | ctg | ggc | tcg | ctg | gag | tcg | ctg | aac | agc | gag | ggg | 576 |
| Gly | Thr | Gln | Asn | Ser | Leu | Gly | Ser | Leu | Glu | Ser | Leu | Asn | Ser | Glu | Gly | |
| | | | 180 | | | | | 185 | | | | | 190 | | | |
| gcc | gcg | cgc | ttc | aac | gcc | aag | tac | ccg | cag | ggc | gtc | ccc | acc | tcg | gcc | 624 |
| Ala | Ala | Arg | Phe | Asn | Ala | Lys | Tyr | Pro | Gln | Gly | Val | Pro | Thr | Ser | Ala | |

```
                195                 200                 205
tgc ggc gag ggc gcc tac aag gtc aac ggc gtg agc tat tac tcc tgg         672
Cys Gly Glu Gly Ala Tyr Lys Val Asn Gly Val Ser Tyr Tyr Ser Trp
    210                 215                 220 agc ggt tcc tcg ccg ctg acc aac ttc ctc gat ccg agc gac gcc ttc         720
Ser Gly Ser Ser Pro Leu Thr Asn Phe Leu Asp Pro Ser Asp Ala Phe
225                 230                 235                 240 ctc ggc gcc tcg tcg ctg acc ttc aag aac ggc acc gcc aac gac ggc         768
Leu Gly Ala Ser Ser Leu Thr Phe Lys Asn Gly Thr Ala Asn Asp Gly
                245                 250                 255 ctg gtc ggc acc tgc agt tcg cac ctg ggc atg gtg atc cgc gac aac         816
Leu Val Gly Thr Cys Ser Ser His Leu Gly Met Val Ile Arg Asp Asn
            260                 265                 270 tac cgg atg aac cac ctg gac gag gtg aac cag gtc ttc ggc ctc acc         864
Tyr Arg Met Asn His Leu Asp Glu Val Asn Gln Val Phe Gly Leu Thr
        275                 280                 285 agc ctg ttc gag acc agc ccg gtc agc gtc tac cgc cag cac gcc aac         912
Ser Leu Phe Glu Thr Ser Pro Val Ser Val Tyr Arg Gln His Ala Asn
    290                 295                 300 cgc ctg aag aac gcc agc ctg tag                                         936
Arg Leu Lys Asn Ala Ser Leu
305                 310

<210> SEQ ID NO 6
<211> LENGTH: 311
<212> TYPE: PRT
<213> ORGANISM: Pseudomonas aeruginosa

<400> SEQUENCE: 6

Met Lys Lys Lys Ser Leu Leu Pro Leu Gly Leu Ala Ile Gly Leu Ala
1               5                   10                  15

Ser Leu Ala Ala Ser Pro Leu Ile Gln Ala Ser Thr Tyr Thr Gln Thr
            20                  25                  30

Lys Tyr Pro Ile Val Leu Ala His Gly Met Leu Gly Phe Asp Asn Ile
        35                  40                  45

Leu Gly Val Asp Tyr Trp Phe Gly Ile Pro Ser Ala Leu Arg Arg Asp
    50                  55                  60

Gly Ala Gln Val Tyr Val Thr Glu Val Ser Gln Leu Asp Thr Ser Glu
65                  70                  75                  80

Val Arg Gly Glu Gln Leu Leu Gln Gln Val Glu Glu Ile Val Ala Leu
                85                  90                  95

Ser Gly Gln Pro Lys Val Asn Leu Ile Gly His Ser His Gly Gly Pro
            100                 105                 110

Thr Ile Arg Tyr Val Ala Ala Val Arg Pro Asp Leu Ile Ala Ser Ala
        115                 120                 125

Thr Ser Val Gly Ala Pro His Lys Gly Ser Asp Thr Ala Asp Phe Leu
    130                 135                 140

Arg Gln Ile Pro Pro Gly Ser Ala Gly Glu Ala Ile Leu Ser Gly Leu
145                 150                 155                 160

Val Asn Ser Leu Gly Ala Leu Ile Ser Phe Leu Ser Ser Gly Ser Thr
                165                 170                 175

Gly Thr Gln Asn Ser Leu Gly Ser Leu Glu Ser Leu Asn Ser Glu Gly
            180                 185                 190

Ala Ala Arg Phe Asn Ala Lys Tyr Pro Gln Gly Val Pro Thr Ser Ala
        195                 200                 205

Cys Gly Glu Gly Ala Tyr Lys Val Asn Gly Val Ser Tyr Tyr Ser Trp
    210                 215                 220
```

-continued

```
Ser Gly Ser Ser Pro Leu Thr Asn Phe Leu Asp Pro Ser Asp Ala Phe
225                 230                 235                 240

Leu Gly Ala Ser Ser Leu Thr Phe Lys Asn Gly Thr Ala Asn Asp Gly
            245                 250                 255

Leu Val Gly Thr Cys Ser Ser His Leu Gly Met Val Ile Arg Asp Asn
        260                 265                 270

Tyr Arg Met Asn His Leu Asp Glu Val Asn Gln Val Phe Gly Leu Thr
    275                 280                 285

Ser Leu Phe Glu Thr Ser Pro Val Ser Val Tyr Arg Gln His Ala Asn
290                 295                 300

Arg Leu Lys Asn Ala Ser Leu
305                 310

<210> SEQ ID NO 7
<211> LENGTH: 2073
<212> TYPE: DNA
<213> ORGANISM: Staphylococcus aureus
<220> FEATURE:
<221> NAME/KEY: CDS
<222> LOCATION: (1)..(2073)

<400> SEQUENCE: 7 atg tta aga gga caa gaa gaa aga aag tat agt att aga aag tat tca      48
Met Leu Arg Gly Gln Glu Glu Arg Lys Tyr Ser Ile Arg Lys Tyr Ser
1               5                   10                  15 ata ggc gtg gtg tca gtg tta gcg gct aca atg ttt gtt gtg tca tca     96
Ile Gly Val Val Ser Val Leu Ala Ala Thr Met Phe Val Val Ser Ser
            20                  25                  30 cat gaa gca caa gcc tcg gaa aaa aca tca act aat gca gcg gca caa    144
His Glu Ala Gln Ala Ser Glu Lys Thr Ser Thr Asn Ala Ala Ala Gln
        35                  40                  45 aaa gaa aca cta aat caa ccg gga gaa caa ggg aat gcg ata acg tca    192
Lys Glu Thr Leu Asn Gln Pro Gly Glu Gln Gly Asn Ala Ile Thr Ser
    50                  55                  60 cat caa atg cag tca gga aag caa tta gac gat atg cat aaa gag aat    240
His Gln Met Gln Ser Gly Lys Gln Leu Asp Asp Met His Lys Glu Asn
65                  70                  75                  80 ggt aaa agt gga aca gtg aca gaa ggt aaa gat acg ctt caa tca tcg    288
Gly Lys Ser Gly Thr Val Thr Glu Gly Lys Asp Thr Leu Gln Ser Ser
                85                  90                  95 aag cat caa tca aca caa aat agt aaa aca atc aga acg caa aat gat    336
Lys His Gln Ser Thr Gln Asn Ser Lys Thr Ile Arg Thr Gln Asn Asp
            100                 105                 110 aat caa gta aag caa gat tct gaa cga caa ggt tct aaa cag tca cac    384
Asn Gln Val Lys Gln Asp Ser Glu Arg Gln Gly Ser Lys Gln Ser His
        115                 120                 125 caa aat aat gcg act aat aat act gaa cgt caa aat gat cag gtt caa    432
Gln Asn Asn Ala Thr Asn Asn Thr Glu Arg Gln Asn Asp Gln Val Gln
    130                 135                 140 aat acc cat cat gct gaa cgt aat gga tca caa tcg aca acg tca caa    480
Asn Thr His His Ala Glu Arg Asn Gly Ser Gln Ser Thr Thr Ser Gln
145                 150                 155                 160 tcg aat gat gtt gat aaa tca caa cca tcc att ccg gca caa aag gta    528
Ser Asn Asp Val Asp Lys Ser Gln Pro Ser Ile Pro Ala Gln Lys Val
                165                 170                 175 ata ccc aat cat gat aaa gca gca cca act tca act aca ccc ccg tct    576
Ile Pro Asn His Asp Lys Ala Ala Pro Thr Ser Thr Thr Pro Pro Ser
            180                 185                 190 aat gat aaa act gca cct aaa tca aca aaa gca caa gat gca acc acg    624
```

|  |  |  |  |  |  |  |  |  |  |  |  |  |  |
|---|---|---|---|---|---|---|---|---|---|---|---|---|---|
| Asn | Asp | Lys | Thr | Ala | Pro | Lys | Ser | Thr | Lys | Ala | Gln | Asp | Ala | Thr | Thr |
|  |  |  | 195 |  |  |  | 200 |  |  |  | 205 |  |  |

```
gac aaa cat cca aat caa caa gat aca cat caa cct gcg cat caa atc      672
Asp Lys His Pro Asn Gln Gln Asp Thr His Gln Pro Ala His Gln Ile
210                 215                 220 ata gat gca aag caa gat gat act gtt cgc caa agt gaa cag aaa cca      720
Ile Asp Ala Lys Gln Asp Asp Thr Val Arg Gln Ser Glu Gln Lys Pro
225                 230                 235                 240 caa gtt ggc gat tta agt aaa cat atc gat ggt caa aat tcc cca gag      768
Gln Val Gly Asp Leu Ser Lys His Ile Asp Gly Gln Asn Ser Pro Glu
                245                 250                 255 aaa ccg aca gat aaa aat act gat aat aaa caa cta atc aaa gat gcg      816
Lys Pro Thr Asp Lys Asn Thr Asp Asn Lys Gln Leu Ile Lys Asp Ala
            260                 265                 270 ctt caa gcg cct aaa aca cgt tcg act aca aat gca gca gca gat gct      864
Leu Gln Ala Pro Lys Thr Arg Ser Thr Thr Asn Ala Ala Ala Asp Ala
        275                 280                 285 aaa aag gtt cga cca ctt aaa gcg aat caa gta caa cca ctt aac aaa      912
Lys Lys Val Arg Pro Leu Lys Ala Asn Gln Val Gln Pro Leu Asn Lys
    290                 295                 300 tat cca gtt gtt ttt gta cat gga ttt tta gga tta gta ggc gat aat      960
Tyr Pro Val Val Phe Val His Gly Phe Leu Gly Leu Val Gly Asp Asn
305                 310                 315                 320 gca cct gct tta tat cca aat tat tgg ggt gga aat aaa ttt aaa gtt     1008
Ala Pro Ala Leu Tyr Pro Asn Tyr Trp Gly Gly Asn Lys Phe Lys Val
                325                 330                 335 atc gaa gaa ttg aga aag caa ggc tat aat gta cat caa gca agt gta     1056
Ile Glu Glu Leu Arg Lys Gln Gly Tyr Asn Val His Gln Ala Ser Val
            340                 345                 350 agt gca ttt ggt agt aac tat gat cgc gct gta gaa ctt tat tat tac     1104
Ser Ala Phe Gly Ser Asn Tyr Asp Arg Ala Val Glu Leu Tyr Tyr Tyr
        355                 360                 365 att aaa ggt ggt cgc gta gat tat ggc gca gca cat gca gct aaa tac     1152
Ile Lys Gly Gly Arg Val Asp Tyr Gly Ala Ala His Ala Ala Lys Tyr
    370                 375                 380 gga cat gag cgc tat ggt aag act tat aaa gga atc atg cct aat tgg     1200
Gly His Glu Arg Tyr Gly Lys Thr Tyr Lys Gly Ile Met Pro Asn Trp
385                 390                 395                 400 gaa cct ggt aaa aag gta cat ctt gta ggg cat agt atg ggt ggt caa     1248
Glu Pro Gly Lys Lys Val His Leu Val Gly His Ser Met Gly Gly Gln
                405                 410                 415 aca att cgt tta atg gaa gag ttt tta aga aat ggt aac aaa gaa gaa     1296
Thr Ile Arg Leu Met Glu Glu Phe Leu Arg Asn Gly Asn Lys Glu Glu
            420                 425                 430 att gcc tat cat aaa gcg cat ggt gga gaa ata tca cca tta ttc act     1344
Ile Ala Tyr His Lys Ala His Gly Gly Glu Ile Ser Pro Leu Phe Thr
        435                 440                 445 ggt ggt cat aac aat atg gtt gca tca atc aca aca tta gca aca cca     1392
Gly Gly His Asn Asn Met Val Ala Ser Ile Thr Thr Leu Ala Thr Pro
    450                 455                 460 cat aat ggt tca caa gca gct gat aag ttt gga aat aca gaa gct gtt     1440
His Asn Gly Ser Gln Ala Ala Asp Lys Phe Gly Asn Thr Glu Ala Val
465                 470                 475                 480 aga aaa atc atg ttc gct tta aat cga ttt atg ggt aac aag tat tcg     1488
Arg Lys Ile Met Phe Ala Leu Asn Arg Phe Met Gly Asn Lys Tyr Ser
                485                 490                 495 aat atc gat tta gga tta acg caa tgg ggc ttt aaa caa tta cca aat     1536
Asn Ile Asp Leu Gly Leu Thr Gln Trp Gly Phe Lys Gln Leu Pro Asn
            500                 505                 510
```

| | | |
|---|---|---|
| gag agt tac att gac tat ata aaa cgc gtt agt aaa agc aaa att tgg<br>Glu Ser Tyr Ile Asp Tyr Ile Lys Arg Val Ser Lys Ser Lys Ile Trp<br>515                    520                    525 | | 1584 |
| aca tca gac gac aat gct gcc tat gat tta acg tta gat ggc tct gca<br>Thr Ser Asp Asp Asn Ala Ala Tyr Asp Leu Thr Leu Asp Gly Ser Ala<br>530                    535                    540 | | 1632 |
| aaa ttg aac aac atg aca agt atg aat cct aat att acg tat acg act<br>Lys Leu Asn Asn Met Thr Ser Met Asn Pro Asn Ile Thr Tyr Thr Thr<br>545                    550                    555                    560 | | 1680 |
| tat aca ggt gta tca tct cat act ggt cca tta ggt tat gaa aat cct<br>Tyr Thr Gly Val Ser Ser His Thr Gly Pro Leu Gly Tyr Glu Asn Pro<br>                    565                    570                    575 | | 1728 |
| gat tta ggt aca ttt ttc tta atg gct aca acg agt aga att att ggt<br>Asp Leu Gly Thr Phe Phe Leu Met Ala Thr Thr Ser Arg Ile Ile Gly<br>580                    585                    590 | | 1776 |
| cat gat gca aga gaa gaa tgg cgt aaa aat gat ggt gtc gta cca gtg<br>His Asp Ala Arg Glu Glu Trp Arg Lys Asn Asp Gly Val Val Pro Val<br>                    595                    600                    605 | | 1824 |
| att tcg tca tta cat ccg tcc aat caa cca ttt gtt aat gtt acg aat<br>Ile Ser Ser Leu His Pro Ser Asn Gln Pro Phe Val Asn Val Thr Asn<br>610                    615                    620 | | 1872 |
| gat gaa cct gcc aca cgc aga ggt atc tgg caa gtt aaa cca atc ata<br>Asp Glu Pro Ala Thr Arg Arg Gly Ile Trp Gln Val Lys Pro Ile Ile<br>625                    630                    635                    640 | | 1920 |
| caa gga tgg gat cat gtc gat ttt atc ggt gtg gac ttc ctg gat ttc<br>Gln Gly Trp Asp His Val Asp Phe Ile Gly Val Asp Phe Leu Asp Phe<br>                    645                    650                    655 | | 1968 |
| aaa cgt aaa ggt gca gaa ctt gcc aac ttc tat aca ggt att ata aat<br>Lys Arg Lys Gly Ala Glu Leu Ala Asn Phe Tyr Thr Gly Ile Ile Asn<br>660                    665                    670 | | 2016 |
| gac ttg ttg cgt gtt gaa gcg act gaa agt aaa gga aca caa ttg aaa<br>Asp Leu Leu Arg Val Glu Ala Thr Glu Ser Lys Gly Thr Gln Leu Lys<br>675                    680                    685 | | 2064 |
| gca agt taa<br>Ala Ser<br>        690 | | 2073 |

<210> SEQ ID NO 8
<211> LENGTH: 690
<212> TYPE: PRT
<213> ORGANISM: Staphylococcus aureus

<400> SEQUENCE: 8

Met Leu Arg Gly Gln Glu Glu Arg Lys Tyr Ser Ile Arg Lys Tyr Ser
1                  5                       10                      15

Ile Gly Val Val Ser Val Leu Ala Ala Thr Met Phe Val Val Ser Ser
                    20                    25                    30

His Glu Ala Gln Ala Ser Glu Lys Thr Ser Thr Asn Ala Ala Ala Gln
                35                      40                    45

Lys Glu Thr Leu Asn Gln Pro Gly Glu Gln Gly Asn Ala Ile Thr Ser
    50                    55                    60

His Gln Met Gln Ser Gly Lys Gln Leu Asp Asp Met His Lys Glu Asn
65                  70                    75                    80

Gly Lys Ser Gly Thr Val Thr Glu Gly Lys Asp Thr Leu Gln Ser Ser
                    85                    90                    95

Lys His Gln Ser Thr Gln Asn Ser Lys Thr Ile Arg Thr Gln Asn Asp
                100                  105                  110

Asn Gln Val Lys Gln Asp Ser Glu Arg Gln Gly Ser Lys Gln Ser His
        115                    120                  125

```
Gln Asn Asn Ala Thr Asn Asn Thr Glu Arg Gln Asn Asp Gln Val Gln
    130                 135                 140

Asn Thr His His Ala Glu Arg Asn Gly Ser Gln Ser Thr Thr Ser Gln
145                 150                 155                 160

Ser Asn Asp Val Asp Lys Ser Gln Pro Ser Ile Pro Ala Gln Lys Val
                165                 170                 175

Ile Pro Asn His Asp Lys Ala Ala Pro Thr Ser Thr Thr Pro Pro Ser
            180                 185                 190

Asn Asp Lys Thr Ala Pro Lys Ser Thr Lys Ala Gln Asp Ala Thr Thr
        195                 200                 205

Asp Lys His Pro Asn Gln Gln Asp Thr His Gln Pro Ala His Gln Ile
    210                 215                 220

Ile Asp Ala Lys Gln Asp Asp Thr Val Arg Gln Ser Glu Gln Lys Pro
225                 230                 235                 240

Gln Val Gly Asp Leu Ser Lys His Ile Asp Gly Gln Asn Ser Pro Glu
                245                 250                 255

Lys Pro Thr Asp Lys Asn Thr Asp Asn Lys Gln Leu Ile Lys Asp Ala
            260                 265                 270

Leu Gln Ala Pro Lys Thr Arg Ser Thr Thr Asn Ala Ala Ala Asp Ala
        275                 280                 285

Lys Lys Val Arg Pro Leu Lys Ala Asn Gln Val Gln Pro Leu Asn Lys
    290                 295                 300

Tyr Pro Val Val Phe Val His Gly Phe Leu Gly Leu Val Gly Asp Asn
305                 310                 315                 320

Ala Pro Ala Leu Tyr Pro Asn Tyr Trp Gly Gly Asn Lys Phe Lys Val
                325                 330                 335

Ile Glu Glu Leu Arg Lys Gln Gly Tyr Asn Val His Gln Ala Ser Val
            340                 345                 350

Ser Ala Phe Gly Ser Asn Tyr Asp Arg Ala Val Glu Leu Tyr Tyr Tyr
        355                 360                 365

Ile Lys Gly Gly Arg Val Asp Tyr Gly Ala Ala His Ala Ala Lys Tyr
    370                 375                 380

Gly His Glu Arg Tyr Gly Lys Thr Tyr Lys Gly Ile Met Pro Asn Trp
385                 390                 395                 400

Glu Pro Gly Lys Lys Val His Leu Val Gly His Ser Met Gly Gly Gln
                405                 410                 415

Thr Ile Arg Leu Met Glu Glu Phe Leu Arg Asn Gly Asn Lys Glu Glu
            420                 425                 430

Ile Ala Tyr His Lys Ala His Gly Gly Glu Ile Ser Pro Leu Phe Thr
        435                 440                 445

Gly Gly His Asn Asn Met Val Ala Ser Ile Thr Thr Leu Ala Thr Pro
    450                 455                 460

His Asn Gly Ser Gln Ala Ala Asp Lys Phe Gly Asn Thr Glu Ala Val
465                 470                 475                 480

Arg Lys Ile Met Phe Ala Leu Asn Arg Phe Met Gly Asn Lys Tyr Ser
                485                 490                 495

Asn Ile Asp Leu Gly Leu Thr Gln Trp Gly Phe Lys Gln Leu Pro Asn
            500                 505                 510

Glu Ser Tyr Ile Asp Tyr Ile Lys Arg Val Ser Lys Ser Lys Ile Trp
        515                 520                 525

Thr Ser Asp Asp Asn Ala Ala Tyr Asp Leu Thr Leu Asp Gly Ser Ala
    530                 535                 540
```

```
Lys Leu Asn Asn Met Thr Ser Met Asn Pro Asn Ile Thr Tyr Thr Thr
545                 550                 555                 560

Tyr Thr Gly Val Ser Ser His Thr Gly Pro Leu Gly Tyr Glu Asn Pro
                565                 570                 575

Asp Leu Gly Thr Phe Phe Leu Met Ala Thr Thr Ser Arg Ile Ile Gly
            580                 585                 590

His Asp Ala Arg Glu Glu Trp Arg Lys Asn Asp Gly Val Val Pro Val
        595                 600                 605

Ile Ser Ser Leu His Pro Ser Asn Gln Pro Phe Val Asn Val Thr Asn
    610                 615                 620

Asp Glu Pro Ala Thr Arg Arg Gly Ile Trp Gln Val Lys Pro Ile Ile
625                 630                 635                 640

Gln Gly Trp Asp His Val Asp Phe Ile Gly Val Asp Phe Leu Asp Phe
                645                 650                 655

Lys Arg Lys Gly Ala Glu Leu Ala Asn Phe Tyr Thr Gly Ile Ile Asn
            660                 665                 670

Asp Leu Leu Arg Val Glu Ala Thr Glu Ser Lys Gly Thr Gln Leu Lys
        675                 680                 685

Ala Ser
    690

<210> SEQ ID NO 9
<211> LENGTH: 1029
<212> TYPE: DNA
<213> ORGANISM: Candida antarctica
<220> FEATURE:
<221> NAME/KEY: CDS
<222> LOCATION: (1)..(1029)

<400> SEQUENCE: 9 atg aag cta ctc tct ctg acc ggt gtg gct ggt gtg ctt gcg act tgc      48
Met Lys Leu Leu Ser Leu Thr Gly Val Ala Gly Val Leu Ala Thr Cys
1               5                   10                  15 gtt gca gcc act cct ttg gtg aag cgt cta cct tcc ggt tcg gac cct      96
Val Ala Ala Thr Pro Leu Val Lys Arg Leu Pro Ser Gly Ser Asp Pro
            20                  25                  30 gcc ttt tcg cag ccc aag tcg gtg ctc gat gcg ggt ctg acc tgc cag     144
Ala Phe Ser Gln Pro Lys Ser Val Leu Asp Ala Gly Leu Thr Cys Gln
        35                  40                  45 ggt gct tcg cca tcc tcg gtc tcc aaa ccc atc ctt ctc gtc ccc gga     192
Gly Ala Ser Pro Ser Ser Val Ser Lys Pro Ile Leu Leu Val Pro Gly
    50                  55                  60 acc ggc acc aca ggt cca cag tcg ttc gac tcg aac tgg atc ccc ctc     240
Thr Gly Thr Thr Gly Pro Gln Ser Phe Asp Ser Asn Trp Ile Pro Leu
65                  70                  75                  80 tca acg cag ttg ggt tac aca ccc tgc tgg atc tca ccc ccg ccg ttc     288
Ser Thr Gln Leu Gly Tyr Thr Pro Cys Trp Ile Ser Pro Pro Pro Phe
                85                  90                  95 atg ctc aac gac acc cag gtc aac acg gag tac atg gtc aac gcc atc     336
Met Leu Asn Asp Thr Gln Val Asn Thr Glu Tyr Met Val Asn Ala Ile
            100                 105                 110 acc gcg ctc tac gct ggt tcg ggc aac aac aag ctt ccc gtg ctt acc     384
Thr Ala Leu Tyr Ala Gly Ser Gly Asn Asn Lys Leu Pro Val Leu Thr
        115                 120                 125 tgg tcc cag ggt ggt ctg gtt gca cag tgg ggt ctg acc ttc ttc ccc     432
Trp Ser Gln Gly Gly Leu Val Ala Gln Trp Gly Leu Thr Phe Phe Pro
    130                 135                 140 agt atc agg tcc aag gtc gat cga ctt atg gcc ttt gcg ccc gac tac     480
Ser Ile Arg Ser Lys Val Asp Arg Leu Met Ala Phe Ala Pro Asp Tyr
```

```
aag ggc acc gtc ctc gcc ggc cct ctc gat gca ctc gcg gtt agt gca    528
Lys Gly Thr Val Leu Ala Gly Pro Leu Asp Ala Leu Ala Val Ser Ala
            165                 170                 175 ccc tcc gta tgg cag caa acc acc ggt tcg gca ctc acc acc gca ctc    576
Pro Ser Val Trp Gln Gln Thr Thr Gly Ser Ala Leu Thr Thr Ala Leu
            180                 185                 190 cga aac gca ggt ggt ctg acc cag atc gtg ccc acc acc aac ctc tac    624
Arg Asn Ala Gly Gly Leu Thr Gln Ile Val Pro Thr Thr Asn Leu Tyr
            195                 200                 205 tcg gcg acc gac gag atc gtt cag cct cag gtg tcc aac tcg cca ctc    672
Ser Ala Thr Asp Glu Ile Val Gln Pro Gln Val Ser Asn Ser Pro Leu
            210                 215                 220 gac tca tcc tac ctc ttc aac gga aag aac gtc cag gca cag gcc gtg    720
Asp Ser Ser Tyr Leu Phe Asn Gly Lys Asn Val Gln Ala Gln Ala Val
225                 230                 235                 240 tgt ggg ccg ctg ttc gtc atc gac cat gca ggc tcg ctc acc tcg cag    768
Cys Gly Pro Leu Phe Val Ile Asp His Ala Gly Ser Leu Thr Ser Gln
            245                 250                 255 ttc tcc tac gtc gtc ggt cga tcc gcc ctg cgc tcc acc acg ggc cag    816
Phe Ser Tyr Val Val Gly Arg Ser Ala Leu Arg Ser Thr Thr Gly Gln
            260                 265                 270 gct cgt agt gca gac tat ggc att acg gac tgc aac cct ctt ccc gcc    864
Ala Arg Ser Ala Asp Tyr Gly Ile Thr Asp Cys Asn Pro Leu Pro Ala
            275                 280                 285 aat gat ctg act ccc gag caa aag gtc gcc gcg gct gcg ctc ctg gcg    912
Asn Asp Leu Thr Pro Glu Gln Lys Val Ala Ala Ala Ala Leu Leu Ala
            290                 295                 300 ccg gca gct gca gcc atc gtg gcg ggt cca aag cag aac tgc gag ccc    960
Pro Ala Ala Ala Ala Ile Val Ala Gly Pro Lys Gln Asn Cys Glu Pro
305                 310                 315                 320 gac ctc atg ccc tac gcc cgc ccc ttt gca gta ggc aaa agg acc tgc   1008
Asp Leu Met Pro Tyr Ala Arg Pro Phe Ala Val Gly Lys Arg Thr Cys
            325                 330                 335 tcc ggc atc gtc acc ccc tga                                       1029
Ser Gly Ile Val Thr Pro
            340

<210> SEQ ID NO 10
<211> LENGTH: 342
<212> TYPE: PRT
<213> ORGANISM: Candida antarctica

<400> SEQUENCE: 10

Met Lys Leu Leu Ser Leu Thr Gly Val Ala Gly Val Leu Ala Thr Cys
1               5                   10                  15

Val Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
            35                  40                  45

Gly Ala Ser Pro Ser Ser Val Ser Lys Pro Ile Leu Leu Val Pro Gly
        50                  55                  60

Thr Gly Thr Thr Gly Pro Gln Ser Phe Asp Ser Asn Trp Ile Pro Leu
65              70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110
```

```
Thr Ala Leu Tyr Ala Gly Ser Gly Asn Asn Lys Leu Pro Val Leu Thr
            115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Ala Leu
                180                 185                 190

Arg Asn Ala Gly Gly Leu Thr Gln Ile Val Pro Thr Thr Asn Leu Tyr
            195                 200                 205

Ser Ala Thr Asp Glu Ile Val Gln Pro Gln Val Ser Asn Ser Pro Leu
    210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
    275                 280                 285

Asn Asp Leu Thr Pro Glu Gln Lys Val Ala Ala Ala Leu Leu Ala
290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 11
<211> LENGTH: 1650
<212> TYPE: DNA
<213> ORGANISM: Candida rugosa
<220> FEATURE:
<221> NAME/KEY: CDS
<222> LOCATION: (1)..(1650)

<400> SEQUENCE: 11 atg gag ctc gct ctt gcg ctc ctg ctc att gcc tcg gtg gct gct gcc     48
Met Glu Leu Ala Leu Ala Leu Leu Leu Ile Ala Ser Val Ala Ala Ala
1               5                   10                  15 ccc acc gcc acg ctc gcc aac ggc gac acc atc acc ggt ctc aac gcc     96
Pro Thr Ala Thr Leu Ala Asn Gly Asp Thr Ile Thr Gly Leu Asn Ala
                20                  25                  30 atc atc aac gag gcg ttc ctc ggc att ccc ttt gcc gag ccg ccg gtg    144
Ile Ile Asn Glu Ala Phe Leu Gly Ile Pro Phe Ala Glu Pro Pro Val
            35                  40                  45 ggc aac ctc cgc ttc aag gac ccc gtg ccg tac tcc ggc tcg ctc gat    192
Gly Asn Leu Arg Phe Lys Asp Pro Val Pro Tyr Ser Gly Ser Leu Asp
        50                  55                  60 ggc cag aag ttc acg ctg tac ggc ccg ctg tgc atg cag cag aac ccc    240
Gly Gln Lys Phe Thr Leu Tyr Gly Pro Leu Cys Met Gln Gln Asn Pro
65                  70                  75                  80 gag ggc acc tac gag gag aac ctc ccc aag gca gcg ctc gac ttg gtg    288
Glu Gly Thr Tyr Glu Glu Asn Leu Pro Lys Ala Ala Leu Asp Leu Val
                85                  90                  95
```

-continued

| | |
|---|---|
| atg cag tcc aag gtg ttt gag gcg gtg ctg ccg ctg agc gag gac tgt<br>Met Gln Ser Lys Val Phe Glu Ala Val Leu Pro Leu Ser Glu Asp Cys<br>               100                      105                  110 | 336 |
| ctc acc atc aac gtg gtg cgg ccg ccg ggc acc aag gcg ggt gcc aac<br>Leu Thr Ile Asn Val Val Arg Pro Pro Gly Thr Lys Ala Gly Ala Asn<br>               115                      120                  125 | 384 |
| ctc ccg gtg atg ctc tgg atc ttt ggc ggc ggg ttt gag gtg ggt ggc<br>Leu Pro Val Met Leu Trp Ile Phe Gly Gly Gly Phe Glu Val Gly Gly<br>130                      135                      140 | 432 |
| acc agc acc ttc cct ccc gcc cag atg atc acc aag agc att gcc atg<br>Thr Ser Thr Phe Pro Pro Ala Gln Met Ile Thr Lys Ser Ile Ala Met<br>145                      150                      155                  160 | 480 |
| ggc aag ccc atc atc cac gtg agc gtc aac tac cgc gtg tcg tcg tgg<br>Gly Lys Pro Ile Ile His Val Ser Val Asn Tyr Arg Val Ser Ser Trp<br>               165                      170                  175 | 528 |
| ggg ttc ttg gct ggc gac gag atc aag gcc gag ggc agt gcc aac gcc<br>Gly Phe Leu Ala Gly Asp Glu Ile Lys Ala Glu Gly Ser Ala Asn Ala<br>                   180                      185                  190 | 576 |
| ggt ttg aag gac cag cgc ttg ggc atg cag tgg gtg gcg gac aac att<br>Gly Leu Lys Asp Gln Arg Leu Gly Met Gln Trp Val Ala Asp Asn Ile<br>               195                      200                  205 | 624 |
| gcg gcg ttt ggc ggc gac ccg acc aag gtg acc atc ttt ggc gag ctg<br>Ala Ala Phe Gly Gly Asp Pro Thr Lys Val Thr Ile Phe Gly Glu Leu<br>210                      215                      220 | 672 |
| gcg ggc agc atg tcg gtc atg tgc cac att ctc tgg aac gac ggc gac<br>Ala Gly Ser Met Ser Val Met Cys His Ile Leu Trp Asn Asp Gly Asp<br>225                      230                      235                  240 | 720 |
| aac acg tac aag ggc aag ccg ctc ttc cgc gcg ggc atc atg cag ctg<br>Asn Thr Tyr Lys Gly Lys Pro Leu Phe Arg Ala Gly Ile Met Gln Leu<br>               245                      250                  255 | 768 |
| ggg gcc atg gtg ccg ctg gac gcc gtg gac ggc atc tac ggc aac gag<br>Gly Ala Met Val Pro Leu Asp Ala Val Asp Gly Ile Tyr Gly Asn Glu<br>                   260                      265                  270 | 816 |
| atc ttt gac ctc ttg gcg tcg aac gcc ggc tgc ggc agc gcc agc gac<br>Ile Phe Asp Leu Leu Ala Ser Asn Ala Gly Cys Gly Ser Ala Ser Asp<br>             275                      280                  285 | 864 |
| aag ctt gcg tgc ttg cgc ggt gtg ctg agc gac acg ttg gag gac gcc<br>Lys Leu Ala Cys Leu Arg Gly Val Leu Ser Asp Thr Leu Glu Asp Ala<br>290                      295                      300 | 912 |
| acc aac aac acc cct ggg ttc ttg gcg tac tcc tcg ttg cgg ttg ctg<br>Thr Asn Asn Thr Pro Gly Phe Leu Ala Tyr Ser Ser Leu Arg Leu Leu<br>305                      310                      315                  320 | 960 |
| tac ctc ccc cgg ccc gac ggc gtg aac atc acc gac gac atg tac gcc<br>Tyr Leu Pro Arg Pro Asp Gly Val Asn Ile Thr Asp Asp Met Tyr Ala<br>                   325                      330                  335 | 1008 |
| ttg gtg cgc gag ggc aag tat gcc aac atc cct gtg atc atc ggc gac<br>Leu Val Arg Glu Gly Lys Tyr Ala Asn Ile Pro Val Ile Ile Gly Asp<br>             340                      345                  350 | 1056 |
| cag aac gac gag ggc acc ttc ttt ggc acc ctg ctg ttg aac gtg acc<br>Gln Asn Asp Glu Gly Thr Phe Phe Gly Thr Leu Leu Leu Asn Val Thr<br>             355                      360                  365 | 1104 |
| acg gat gcc cag gcc cgc gag tac ttc aag cag ctg ttt gtc cac gcc<br>Thr Asp Ala Gln Ala Arg Glu Tyr Phe Lys Gln Leu Phe Val His Ala<br>370                      375                      380 | 1152 |
| agc gac gcg gag atc gac acg ttg atg acg gcg tac ccc ggc gac atc<br>Ser Asp Ala Glu Ile Asp Thr Leu Met Thr Ala Tyr Pro Gly Asp Ile<br>385                      390                      395                  400 | 1200 |
| acc cag ggc ctg ccg ttc gac acg ggt att ctc aac gcc ctc acc ccg<br>Thr Gln Gly Leu Pro Phe Asp Thr Gly Ile Leu Asn Ala Leu Thr Pro | 1248 |

```
                          405                 410                 415
cag ttc aag aga atc ctg gcg gtg ctc ggc gac ctt ggc ttt acg ctt          1296
Gln Phe Lys Arg Ile Leu Ala Val Leu Gly Asp Leu Gly Phe Thr Leu
            420                 425                 430 gct cgt cgc tac ttc ctc aac cac tac acc ggc ggc acc aag tac tca          1344
Ala Arg Arg Tyr Phe Leu Asn His Tyr Thr Gly Gly Thr Lys Tyr Ser
        435                 440                 445 ttc ctc ctg aag cag ctc ctg ggc ttg ccg gtg ctc gga acg ttc cac          1392
Phe Leu Leu Lys Gln Leu Leu Gly Leu Pro Val Leu Gly Thr Phe His
450                 455                 460 tcc aac gac att gtc ttc cag gac tac ttg ttg ggc agc ggc tcg ctc          1440
Ser Asn Asp Ile Val Phe Gln Asp Tyr Leu Leu Gly Ser Gly Ser Leu
465                 470                 475                 480 atc tac aac aac gcg ttc att gcg ttt gcc acg gac ttg gac ccc aac          1488
Ile Tyr Asn Asn Ala Phe Ile Ala Phe Ala Thr Asp Leu Asp Pro Asn
                485                 490                 495 acc gcg ggg ttg ttg gtg aag tgg ccc gag tac acc agc agc ctg cag          1536
Thr Ala Gly Leu Leu Val Lys Trp Pro Glu Tyr Thr Ser Ser Leu Gln
            500                 505                 510 ctg ggc aac aac ttg atg atg atc aac gcc ttg ggc ttg tac acc ggc          1584
Leu Gly Asn Asn Leu Met Met Ile Asn Ala Leu Gly Leu Tyr Thr Gly
        515                 520                 525 aag gac aac ttc cgc acc gcc ggc tac gac gcg ttg ttc tcc aac ccg          1632
Lys Asp Asn Phe Arg Thr Ala Gly Tyr Asp Ala Leu Phe Ser Asn Pro
530                 535                 540 ccg ctg ttc ttt gtg taa                                                  1650
Pro Leu Phe Phe Val
545

<210> SEQ ID NO 12
<211> LENGTH: 549
<212> TYPE: PRT
<213> ORGANISM: Candida rugosa

<400> SEQUENCE: 12

Met Glu Leu Ala Leu Ala Leu Leu Ile Ala Ser Val Ala Ala
1               5                   10                  15

Pro Thr Ala Thr Leu Ala Asn Gly Asp Thr Ile Thr Gly Leu Asn Ala
            20                  25                  30

Ile Ile Asn Glu Ala Phe Leu Gly Ile Pro Phe Ala Glu Pro Pro Val
        35                  40                  45

Gly Asn Leu Arg Phe Lys Asp Pro Val Pro Tyr Ser Gly Ser Leu Asp
    50                  55                  60

Gly Gln Lys Phe Thr Leu Tyr Gly Pro Leu Cys Met Gln Gln Asn Pro
65                  70                  75                  80

Glu Gly Thr Tyr Glu Glu Asn Leu Pro Lys Ala Ala Leu Asp Leu Val
                85                  90                  95

Met Gln Ser Lys Val Phe Glu Ala Val Leu Pro Leu Ser Glu Asp Cys
            100                 105                 110

Leu Thr Ile Asn Val Val Arg Pro Pro Gly Thr Lys Ala Gly Ala Asn
        115                 120                 125

Leu Pro Val Met Leu Trp Ile Phe Gly Gly Gly Phe Glu Val Gly Gly
    130                 135                 140

Thr Ser Thr Phe Pro Pro Ala Gln Met Ile Thr Lys Ser Ile Ala Met
145                 150                 155                 160

Gly Lys Pro Ile Ile His Val Ser Val Asn Tyr Arg Val Ser Ser Trp
                165                 170                 175
```

```
Gly Phe Leu Ala Gly Asp Glu Ile Lys Ala Glu Gly Ser Ala Asn Ala
                180                 185                 190

Gly Leu Lys Asp Gln Arg Leu Gly Met Gln Trp Val Ala Asp Asn Ile
            195                 200                 205

Ala Ala Phe Gly Gly Asp Pro Thr Lys Val Thr Ile Phe Gly Glu Leu
210                 215                 220

Ala Gly Ser Met Ser Val Met Cys His Ile Leu Trp Asn Asp Gly Asp
225                 230                 235                 240

Asn Thr Tyr Lys Gly Lys Pro Leu Phe Arg Ala Gly Ile Met Gln Leu
                245                 250                 255

Gly Ala Met Val Pro Leu Asp Ala Val Asp Gly Ile Tyr Gly Asn Glu
            260                 265                 270

Ile Phe Asp Leu Leu Ala Ser Asn Ala Gly Cys Gly Ser Ala Ser Asp
        275                 280                 285

Lys Leu Ala Cys Leu Arg Gly Val Leu Ser Asp Thr Leu Glu Asp Ala
290                 295                 300

Thr Asn Asn Thr Pro Gly Phe Leu Ala Tyr Ser Ser Leu Arg Leu Leu
305                 310                 315                 320

Tyr Leu Pro Arg Pro Asp Gly Val Asn Ile Thr Asp Asp Met Tyr Ala
                325                 330                 335

Leu Val Arg Glu Gly Lys Tyr Ala Asn Ile Pro Val Ile Ile Gly Asp
            340                 345                 350

Gln Asn Asp Glu Gly Thr Phe Phe Gly Thr Leu Leu Leu Asn Val Thr
        355                 360                 365

Thr Asp Ala Gln Ala Arg Glu Tyr Phe Lys Gln Leu Phe Val His Ala
370                 375                 380

Ser Asp Ala Glu Ile Asp Thr Leu Met Thr Ala Tyr Pro Gly Asp Ile
385                 390                 395                 400

Thr Gln Gly Leu Pro Phe Asp Thr Gly Ile Leu Asn Ala Leu Thr Pro
                405                 410                 415

Gln Phe Lys Arg Ile Leu Ala Val Leu Gly Asp Leu Gly Phe Thr Leu
            420                 425                 430

Ala Arg Arg Tyr Phe Leu Asn His Tyr Thr Gly Gly Thr Lys Tyr Ser
        435                 440                 445

Phe Leu Leu Lys Gln Leu Leu Gly Leu Pro Val Leu Gly Thr Phe His
450                 455                 460

Ser Asn Asp Ile Val Phe Gln Asp Tyr Leu Leu Gly Ser Gly Ser Leu
465                 470                 475                 480

Ile Tyr Asn Asn Ala Phe Ile Ala Phe Ala Thr Asp Leu Asp Pro Asn
                485                 490                 495

Thr Ala Gly Leu Leu Val Lys Trp Pro Glu Tyr Thr Ser Ser Leu Gln
            500                 505                 510

Leu Gly Asn Asn Leu Met Met Ile Asn Ala Leu Gly Leu Tyr Thr Gly
        515                 520                 525

Lys Asp Asn Phe Arg Thr Ala Gly Tyr Asp Ala Leu Phe Ser Asn Pro
530                 535                 540

Pro Leu Phe Phe Val
545

<210> SEQ ID NO 13
<211> LENGTH: 1647
<212> TYPE: DNA
<213> ORGANISM: Candida rugosa
<220> FEATURE:
<221> NAME/KEY: CDS
```

<222> LOCATION: (1)..(1647)

<400> SEQUENCE: 13

```
atg aag ctc tgt ttg ctt gct ctt ggt gct gcg gtg gcg gca gcc ccc      48
Met Lys Leu Cys Leu Leu Ala Leu Gly Ala Ala Val Ala Ala Ala Pro
1               5                   10                  15 acg gcc acc ctc gcc aac ggc gac acc atc acc ggt ctc aac gcc att      96
Thr Ala Thr Leu Ala Asn Gly Asp Thr Ile Thr Gly Leu Asn Ala Ile
            20                  25                  30 gtc aac gaa aag ttt ctc ggc ata ccg ttt gcc gag ccg ccc gtg ggc     144
Val Asn Glu Lys Phe Leu Gly Ile Pro Phe Ala Glu Pro Pro Val Gly
        35                  40                  45 acg ctc cgc ttc aag ccg ccc gtg ccg tac tcg gcg tcg ctc aac ggc     192
Thr Leu Arg Phe Lys Pro Pro Val Pro Tyr Ser Ala Ser Leu Asn Gly
50                  55                  60 cag cag ttt acc ctg tac ggc ccg ctg tgc atg cag atg aac cct atg     240
Gln Gln Phe Thr Leu Tyr Gly Pro Leu Cys Met Gln Met Asn Pro Met
65                  70                  75                  80 ggc tcg ttt gag gac aca ctt ccc aag aat gcg cgg cat ttg gtg ctc     288
Gly Ser Phe Glu Asp Thr Leu Pro Lys Asn Ala Arg His Leu Val Leu
                85                  90                  95 cag tcc aag atc ttc caa gtg gtg ctt ccc aac gac gag gac tgt ctc     336
Gln Ser Lys Ile Phe Gln Val Val Leu Pro Asn Asp Glu Asp Cys Leu
            100                 105                 110 acc atc aac gtg atc cgg ccg ccc ggc acc agg gcc agt gct ggt ctc     384
Thr Ile Asn Val Ile Arg Pro Pro Gly Thr Arg Ala Ser Ala Gly Leu
        115                 120                 125 ccg gtg atg ctc tgg atc ttt ggc ggt ggg ttt gag ctt ggc ggc tcc     432
Pro Val Met Leu Trp Ile Phe Gly Gly Gly Phe Glu Leu Gly Gly Ser
130                 135                 140 agc ctc ttt cca gga gac cag atg gtg gcc aag agc gtg ctc atg ggt     480
Ser Leu Phe Pro Gly Asp Gln Met Val Ala Lys Ser Val Leu Met Gly
145                 150                 155                 160 aaa ccg gtg atc cac gtg agc atg aac tac cgc gtg gcg tca tgg ggg     528
Lys Pro Val Ile His Val Ser Met Asn Tyr Arg Val Ala Ser Trp Gly
                165                 170                 175 ttc ttg gcc ggc ccc gac atc cag aac gaa ggc agc ggg aac gcc ggc     576
Phe Leu Ala Gly Pro Asp Ile Gln Asn Glu Gly Ser Gly Asn Ala Gly
            180                 185                 190 ttg cat gac cag cgc ttg gcc atg cag tgg gtg gcg gac aac att gct     624
Leu His Asp Gln Arg Leu Ala Met Gln Trp Val Ala Asp Asn Ile Ala
        195                 200                 205 ggg ttt ggc ggc gac ccg agc aag gtg acc ata tac ggc gag ctg gcg     672
Gly Phe Gly Gly Asp Pro Ser Lys Val Thr Ile Tyr Gly Glu Leu Ala
210                 215                 220 ggc agc atg tcg acg ttt gtg cac ctt gtg tgg aac gac ggc gac aac     720
Gly Ser Met Ser Thr Phe Val His Leu Val Trp Asn Asp Gly Asp Asn
225                 230                 235                 240 acg tac aac ggc aag ccg ttg ttc cgc gcc gcc atc atg cag ctg ggc     768
Thr Tyr Asn Gly Lys Pro Leu Phe Arg Ala Ala Ile Met Gln Leu Gly
                245                 250                 255 tgc atg gtg ccg ctg gac ccg gtg gac ggc acg tac ggc acc gag atc     816
Cys Met Val Pro Leu Asp Pro Val Asp Gly Thr Tyr Gly Thr Glu Ile
            260                 265                 270 tac aac cag gtg gtg gcg tct gcc ggg tgt ggc agt gcc agc gac aag     864
Tyr Asn Gln Val Val Ala Ser Ala Gly Cys Gly Ser Ala Ser Asp Lys
        275                 280                 285 ctc gcg tgc ttg cgc ggc ctt ctg cag gac acg ttg tac cag gcc acg     912
Leu Ala Cys Leu Arg Gly Leu Leu Gln Asp Thr Leu Tyr Gln Ala Thr
290                 295                 300
```

```
agc gac acg ccc ggc gtg ttg gcg tac ccg tcg ttg cgg ttg ctg tat      960
Ser Asp Thr Pro Gly Val Leu Ala Tyr Pro Ser Leu Arg Leu Leu Tyr
305                 310                 315                 320 ctc ccg cgg ccc gac ggc acc ttc atc acc gac gac atg tat gcc ttg     1008
Leu Pro Arg Pro Asp Gly Thr Phe Ile Thr Asp Asp Met Tyr Ala Leu
                325                 330                 335 gtg cgg gac ggc aag tac gca cac gtg ccg gtg atc atc ggc gac cag     1056
Val Arg Asp Gly Lys Tyr Ala His Val Pro Val Ile Ile Gly Asp Gln
            340                 345                 350 aac gac gag ggc act ttg ttt ggg ctc ctg ttg aac gtg acc aca         1104
Asn Asp Glu Gly Thr Leu Phe Gly Leu Leu Leu Asn Val Thr Thr
        355                 360                 365 gat gct cag gca cgg gcg tac ttc aag cag ctg ttc atc cac gcc agc     1152
Asp Ala Gln Ala Arg Ala Tyr Phe Lys Gln Leu Phe Ile His Ala Ser
    370                 375                 380 gat gcg gag atc gac acg ttg atg gcg gcg tac acc agc gac atc acc     1200
Asp Ala Glu Ile Asp Thr Leu Met Ala Ala Tyr Thr Ser Asp Ile Thr
385                 390                 395                 400 cag ggt ctg ccg ttc gac acc ggc atc ttc aat gcc atc acc ccg cag     1248
Gln Gly Leu Pro Phe Asp Thr Gly Ile Phe Asn Ala Ile Thr Pro Gln
                405                 410                 415 ttc aaa cgg atc ctg gcg ttg ctt ggc gac ctt gcg ttc acg ctt gcg     1296
Phe Lys Arg Ile Leu Ala Leu Leu Gly Asp Leu Ala Phe Thr Leu Ala
            420                 425                 430 cgt cgc tac ttc ctc aac tac tac cag ggc ggc acc aag tac tcg ttt     1344
Arg Arg Tyr Phe Leu Asn Tyr Tyr Gln Gly Gly Thr Lys Tyr Ser Phe
        435                 440                 445 ctc ctg aag cag ctt ctg ggg ttg ccc gtc ttg ggc acc ttc cac ggc     1392
Leu Leu Lys Gln Leu Leu Gly Leu Pro Val Leu Gly Thr Phe His Gly
    450                 455                 460 aac gac atc atc tgg cag gac tac ttg gtg ggc agc ggc agt gtg atc     1440
Asn Asp Ile Ile Trp Gln Asp Tyr Leu Val Gly Ser Gly Ser Val Ile
465                 470                 475                 480 tac aac aac gcg ttc att gcg ttt gcc aac gac ctc gac ccg aac aag     1488
Tyr Asn Asn Ala Phe Ile Ala Phe Ala Asn Asp Leu Asp Pro Asn Lys
                485                 490                 495 gcg ggc ttg tgg acc aac tgg ccc acg tac acc agc agt ctg cag ctg     1536
Ala Gly Leu Trp Thr Asn Trp Pro Thr Tyr Thr Ser Ser Leu Gln Leu
            500                 505                 510 ggc aac aac ttg atg cag atc aac ggc ttg ggg ttg tac acc ggc aag     1584
Gly Asn Asn Leu Met Gln Ile Asn Gly Leu Gly Leu Tyr Thr Gly Lys
        515                 520                 525 gac aac ttc cgc ccg gat gcg tac agc gcc ctc ttt tcc aac ccg cca     1632
Asp Asn Phe Arg Pro Asp Ala Tyr Ser Ala Leu Phe Ser Asn Pro Pro
    530                 535                 540 ctg ttc ttt gtg tag                                                 1647
Leu Phe Phe Val
545

<210> SEQ ID NO 14
<211> LENGTH: 548
<212> TYPE: PRT
<213> ORGANISM: Candida rugosa

<400> SEQUENCE: 14

Met Lys Leu Cys Leu Leu Ala Leu Gly Ala Ala Val Ala Ala Ala Pro
1               5                   10                  15

Thr Ala Thr Leu Ala Asn Gly Asp Thr Ile Thr Gly Leu Asn Ala Ile
            20                  25                  30
```

```
Val Asn Glu Lys Phe Leu Gly Ile Pro Phe Ala Glu Pro Val Gly
         35                  40                  45
Thr Leu Arg Phe Lys Pro Pro Val Pro Tyr Ser Ala Ser Leu Asn Gly
 50                  55                  60
Gln Gln Phe Thr Leu Tyr Gly Pro Leu Cys Met Gln Met Asn Pro Met
 65                  70                  75                  80
Gly Ser Phe Glu Asp Thr Leu Pro Lys Asn Ala Arg His Leu Val Leu
                 85                  90                  95
Gln Ser Lys Ile Phe Gln Val Val Leu Pro Asn Asp Glu Asp Cys Leu
                100                 105                 110
Thr Ile Asn Val Ile Arg Pro Pro Gly Thr Arg Ala Ser Ala Gly Leu
             115                 120                 125
Pro Val Met Leu Trp Ile Phe Gly Gly Gly Phe Glu Leu Gly Gly Ser
130                 135                 140
Ser Leu Phe Pro Gly Asp Gln Met Val Ala Lys Ser Val Leu Met Gly
145                 150                 155                 160
Lys Pro Val Ile His Val Ser Met Asn Tyr Arg Val Ala Ser Trp Gly
                165                 170                 175
Phe Leu Ala Gly Pro Asp Ile Gln Asn Glu Gly Ser Gly Asn Ala Gly
                180                 185                 190
Leu His Asp Gln Arg Leu Ala Met Gln Trp Val Ala Asp Asn Ile Ala
            195                 200                 205
Gly Phe Gly Gly Asp Pro Ser Lys Val Thr Ile Tyr Gly Glu Leu Ala
        210                 215                 220
Gly Ser Met Ser Thr Phe Val His Leu Val Trp Asn Asp Gly Asp Asn
225                 230                 235                 240
Thr Tyr Asn Gly Lys Pro Leu Phe Arg Ala Ala Ile Met Gln Leu Gly
                245                 250                 255
Cys Met Val Pro Leu Asp Pro Val Asp Gly Thr Tyr Gly Thr Glu Ile
                260                 265                 270
Tyr Asn Gln Val Val Ala Ser Ala Gly Cys Gly Ser Ala Ser Asp Lys
            275                 280                 285
Leu Ala Cys Leu Arg Gly Leu Leu Gln Asp Thr Leu Tyr Gln Ala Thr
        290                 295                 300
Ser Asp Thr Pro Gly Val Leu Ala Tyr Pro Ser Leu Arg Leu Leu Tyr
305                 310                 315                 320
Leu Pro Arg Pro Asp Gly Thr Phe Ile Thr Asp Met Tyr Ala Leu
                325                 330                 335
Val Arg Asp Gly Lys Tyr Ala His Val Pro Val Ile Ile Gly Asp Gln
            340                 345                 350
Asn Asp Glu Gly Thr Leu Phe Gly Leu Leu Leu Asn Val Thr Thr
        355                 360                 365
Asp Ala Gln Ala Arg Ala Tyr Phe Lys Gln Leu Phe Ile His Ala Ser
    370                 375                 380
Asp Ala Glu Ile Asp Thr Leu Met Ala Ala Tyr Thr Ser Asp Ile Thr
385                 390                 395                 400
Gln Gly Leu Pro Phe Asp Thr Gly Ile Phe Asn Ala Ile Thr Pro Gln
                405                 410                 415
Phe Lys Arg Ile Leu Ala Leu Leu Gly Asp Leu Ala Phe Thr Leu Ala
            420                 425                 430
Arg Arg Tyr Phe Leu Asn Tyr Tyr Gln Gly Gly Thr Lys Tyr Ser Phe
        435                 440                 445
```

```
Leu Leu Lys Gln Leu Leu Gly Leu Pro Val Leu Gly Thr Phe His Gly
    450                 455                 460

Asn Asp Ile Ile Trp Gln Asp Tyr Leu Val Gly Ser Gly Ser Val Ile
465                 470                 475                 480

Tyr Asn Asn Ala Phe Ile Ala Phe Ala Asn Asp Leu Asp Pro Asn Lys
                485                 490                 495

Ala Gly Leu Trp Thr Asn Trp Pro Thr Tyr Thr Ser Ser Leu Gln Leu
            500                 505                 510

Gly Asn Asn Leu Met Gln Ile Asn Gly Leu Gly Leu Tyr Thr Gly Lys
            515                 520                 525

Asp Asn Phe Arg Pro Asp Ala Tyr Ser Ala Leu Phe Ser Asn Pro Pro
530                 535                 540

Leu Phe Phe Val
545

<210> SEQ ID NO 15
<211> LENGTH: 720
<212> TYPE: DNA
<213> ORGANISM: Escherichia coli
<220> FEATURE:
<221> NAME/KEY: CDS
<222> LOCATION: (1)..(717)

<400> SEQUENCE: 15 atg gtc att aag gcg caa agc ccg gcg ggt ttc gcg gaa gag tac att      48
Met Val Ile Lys Ala Gln Ser Pro Ala Gly Phe Ala Glu Glu Tyr Ile
1               5                   10                  15 att gaa agt atc tgg aat aac cgc ttc cct ccc ggg act att ttg ccc      96
Ile Glu Ser Ile Trp Asn Asn Arg Phe Pro Pro Gly Thr Ile Leu Pro
                20                  25                  30 gca gaa cgt gaa ctt tca gaa tta att ggc gta acg cgt act acg tta     144
Ala Glu Arg Glu Leu Ser Glu Leu Ile Gly Val Thr Arg Thr Thr Leu
            35                  40                  45 cgt gaa gtg tta cag cgt ctg gca cga gat ggc tgg ttg acc att caa     192
Arg Glu Val Leu Gln Arg Leu Ala Arg Asp Gly Trp Leu Thr Ile Gln
50                  55                  60 cat ggc aag ccg acg aag gtg aat aat ttc tgg gaa act tcc ggt tta     240
His Gly Lys Pro Thr Lys Val Asn Asn Phe Trp Glu Thr Ser Gly Leu
65                  70                  75                  80 aat atc ctt gaa aca ctg gcg cga ctg gat cac gaa agt gtg ccg cag     288
Asn Ile Leu Glu Thr Leu Ala Arg Leu Asp His Glu Ser Val Pro Gln
                85                  90                  95 ctt att gat aat ttg ctg tcg gtg cgt acc aat att tcc act att ttt     336
Leu Ile Asp Asn Leu Leu Ser Val Arg Thr Asn Ile Ser Thr Ile Phe
            100                 105                 110 att cgc acc gcg ttt cgt cag cat ccc gat aaa gcg cag gaa gtg ctg     384
Ile Arg Thr Ala Phe Arg Gln His Pro Asp Lys Ala Gln Glu Val Leu
        115                 120                 125 gct acc gct aat gaa gtg gcc gat cac gcc gat gcc ttt gcc gag ctg     432
Ala Thr Ala Asn Glu Val Ala Asp His Ala Asp Ala Phe Ala Glu Leu
130                 135                 140 gat tac aac ata ttc cgc ggc ctg gcg ttt gct tcc ggc aac ccg att     480
Asp Tyr Asn Ile Phe Arg Gly Leu Ala Phe Ala Ser Gly Asn Pro Ile
145                 150                 155                 160 tac ggt ctg att ctt aac ggg atg aaa ggg ctg tat acg cgt att ggt     528
Tyr Gly Leu Ile Leu Asn Gly Met Lys Gly Leu Tyr Thr Arg Ile Gly
                165                 170                 175 cgt cac tat ttc gcc aat ccg gaa gcg cgc agt ctg gcg ctg ggc ttc     576
Arg His Tyr Phe Ala Asn Pro Glu Ala Arg Ser Leu Ala Leu Gly Phe
            180                 185                 190
```

```
tac cac aaa ctg tcg gcg ttg tgc agt gaa ggc gcg cac gat cag gtg      624
Tyr His Lys Leu Ser Ala Leu Cys Ser Glu Gly Ala His Asp Gln Val
        195                 200                 205 tac gaa aca gtg cgt cgc tat ggg cat gag agt ggc gag att tgg cac      672
Tyr Glu Thr Val Arg Arg Tyr Gly His Glu Ser Gly Glu Ile Trp His
    210                 215                 220 cgg atg cag aaa aat ctg ccg ggt gat tta gcc att cag ggg cga taa      720
Arg Met Gln Lys Asn Leu Pro Gly Asp Leu Ala Ile Gln Gly Arg
225                 230                 235

<210> SEQ ID NO 16
<211> LENGTH: 63
<212> TYPE: DNA
<213> ORGANISM: Artificial
<220> FEATURE:
<223> OTHER INFORMATION: Primer for fadR amplification

<400> SEQUENCE: 16
tatgatgagt ccaactttgt tttgctgtgt tatggaaatc tcacttgaag cctgcttttt      60
tat                                                                   63

<210> SEQ ID NO 17
<211> LENGTH: 63
<212> TYPE: DNA
<213> ORGANISM: Artificial
<220> FEATURE:
<223> OTHER INFORMATION: Primer for fadR amplification

<400> SEQUENCE: 17
caaaaaaccc ctcgtttgag gggtttgctc tttaaacgga agggacgctc aagttagtat      60
aaa                                                                   63

<210> SEQ ID NO 18
<211> LENGTH: 720
<212> TYPE: DNA
<213> ORGANISM: Cryptococcus
<220> FEATURE:
<221> NAME/KEY: CDS
<222> LOCATION: (1)..(717)
<220> FEATURE:
<221> NAME/KEY: sig_peptide
<222> LOCATION: (1)..(102)
<220> FEATURE:
<221> NAME/KEY: mat_peptide
<222> LOCATION: (103)..(717)

<400> SEQUENCE: 18 atg ctc gtc tcc gct ctc gct ctc gcg gtg ctg tcc gct gct tct ctc       48
Met Leu Val Ser Ala Leu Ala Leu Ala Val Leu Ser Ala Ala Ser Leu
                -30                 -25                 -20 ggc cga gcc gca cca acg ccc gag tcc gcc gag gcg cac gag ctc gag       96
Gly Arg Ala Ala Pro Thr Pro Glu Ser Ala Glu Ala His Glu Leu Glu
            -15                 -10                  -5 gcc cgc gcc acg tcc agc gct tgt ccg cag tac gtc ctg atc aac acg      144
Ala Arg Ala Thr Ser Ser Ala Cys Pro Gln Tyr Val Leu Ile Asn Thr
     -1   1                  5                  10 cga ggc acg ggc gag ccg caa ggc cag tcg gcc ggc ttc cga acg atg      192
Arg Gly Thr Gly Glu Pro Gln Gly Gln Ser Ala Gly Phe Arg Thr Met
 15                  20                  25                  30 aac agc cag atc acc gcc gcg ctg tcg ggt ggc acc atc tac aac act      240
Asn Ser Gln Ile Thr Ala Ala Leu Ser Gly Gly Thr Ile Tyr Asn Thr
                 35                  40                  45
```

| | | | | | | | | | | | | | | | |
|---|---|---|---|---|---|---|---|---|---|---|---|---|---|---|---|
| gtc | tac | acc | gcc | gat | ttc | agc | cag | aac | agc | gcg | gcc | ggc | acg | gcc | gac | 288 |
| Val | Tyr | Thr | Ala | Asp | Phe | Ser | Gln | Asn | Ser | Ala | Ala | Gly | Thr | Ala | Asp | |
| | | | 50 | | | | | 55 | | | | | 60 | | | |

| atc | atc | cgc | cgg | atc | aac | tcg | ggt | ctc | gcg | gcc | aac | ccg | aac | gtg | tgc | 336 |
| Ile | Ile | Arg | Arg | Ile | Asn | Ser | Gly | Leu | Ala | Ala | Asn | Pro | Asn | Val | Cys | |
| | | | | 65 | | | | | 70 | | | | | 75 | | |

| tac | atc | ctc | caa | ggg | tac | agc | cag | ggc | gcg | gct | gct | acc | gtc | gtc | gcg | 384 |
| Tyr | Ile | Leu | Gln | Gly | Tyr | Ser | Gln | Gly | Ala | Ala | Ala | Thr | Val | Val | Ala | |
| | 80 | | | | | 85 | | | | | 90 | | | | | |

| ctg | caa | cag | ctc | ggc | acg | agt | gga | gcg | gcg | ttc | aac | gcc | gtc | aag | ggt | 432 |
| Leu | Gln | Gln | Leu | Gly | Thr | Ser | Gly | Ala | Ala | Phe | Asn | Ala | Val | Lys | Gly | |
| 95 | | | | | 100 | | | | | 105 | | | | | 110 | |

| gtg | ttc | ctc | att | ggc | aac | ccg | gac | cac | aag | tcg | ggc | ctg | act | tgc | aac | 480 |
| Val | Phe | Leu | Ile | Gly | Asn | Pro | Asp | His | Lys | Ser | Gly | Leu | Thr | Cys | Asn | |
| | | | | 115 | | | | | 120 | | | | | 125 | | |

| gtc | gac | tcg | aac | ggc | ggc | act | acc | aca | cgc | aat | gtc | aac | ggc | ctg | tcg | 528 |
| Val | Asp | Ser | Asn | Gly | Gly | Thr | Thr | Thr | Arg | Asn | Val | Asn | Gly | Leu | Ser | |
| | | | 130 | | | | | 135 | | | | | 140 | | | |

| gtc | gcg | tac | cag | ggc | tcg | gtc | ccc | tca | gga | tgg | gtc | agc | aag | act | ctc | 576 |
| Val | Ala | Tyr | Gln | Gly | Ser | Val | Pro | Ser | Gly | Trp | Val | Ser | Lys | Thr | Leu | |
| | | 145 | | | | | 150 | | | | | 155 | | | | |

| gat | gtc | tgc | gct | tat | ggc | gac | ggc | gtg | tgc | gac | acc | gcg | cac | gga | ttc | 624 |
| Asp | Val | Cys | Ala | Tyr | Gly | Asp | Gly | Val | Cys | Asp | Thr | Ala | His | Gly | Phe | |
| | 160 | | | | | 165 | | | | | 170 | | | | | |

| ggt | atc | aac | gca | cag | cac | ctg | tcg | tac | cct | agt | gac | caa | ggc | gtc | cag | 672 |
| Gly | Ile | Asn | Ala | Gln | His | Leu | Ser | Tyr | Pro | Ser | Asp | Gln | Gly | Val | Gln | |
| 175 | | | | | 180 | | | | | 185 | | | | | 190 | |

| acc | atg | gga | tac | aag | ttt | gcc | gtc | aac | aag | ctt | ggc | ggg | tcg | gcc | taa | 720 |
| Thr | Met | Gly | Tyr | Lys | Phe | Ala | Val | Asn | Lys | Leu | Gly | Gly | Ser | Ala | | |
| | | | | 195 | | | | | 200 | | | | | 205 | | |

<210> SEQ ID NO 19
<211> LENGTH: 239
<212> TYPE: PRT
<213> ORGANISM: Cryptococcus

<400> SEQUENCE: 19

Met Leu Val Ser Ala Leu Ala Leu Ala Val Leu Ser Ala Ala Ser Leu
                -30                 -25                 -20

Gly Arg Ala Ala Pro Thr Pro Glu Ser Ala Glu Ala His Glu Leu Glu
            -15                 -10                  -5

Ala Arg Ala Thr Ser Ser Ala Cys Pro Gln Tyr Val Leu Ile Asn Thr
     -1   1               5                   10

Arg Gly Thr Gly Glu Pro Gln Gly Gln Ser Ala Gly Phe Arg Thr Met
 15                  20                  25                  30

Asn Ser Gln Ile Thr Ala Ala Leu Ser Gly Thr Ile Tyr Asn Thr
                 35                  40                  45

Val Tyr Thr Ala Asp Phe Ser Gln Asn Ser Ala Ala Gly Thr Ala Asp
                 50                  55                  60

Ile Ile Arg Arg Ile Asn Ser Gly Leu Ala Ala Asn Pro Asn Val Cys
             65                  70                  75

Tyr Ile Leu Gln Gly Tyr Ser Gln Gly Ala Ala Ala Thr Val Val Ala
         80                  85                  90

Leu Gln Gln Leu Gly Thr Ser Gly Ala Ala Phe Asn Ala Val Lys Gly
 95                 100                 105                 110

Val Phe Leu Ile Gly Asn Pro Asp His Lys Ser Gly Leu Thr Cys Asn
                115                 120                 125

```
Val Asp Ser Asn Gly Gly Thr Thr Thr Arg Asn Val Asn Gly Leu Ser
        130                 135                 140

Val Ala Tyr Gln Gly Ser Val Pro Ser Gly Trp Val Ser Lys Thr Leu
        145                 150                 155

Asp Val Cys Ala Tyr Gly Asp Gly Val Cys Asp Thr Ala His Gly Phe
        160                 165                 170

Gly Ile Asn Ala Gln His Leu Ser Tyr Pro Ser Asp Gln Gly Val Gln
175                 180                 185                 190

Thr Met Gly Tyr Lys Phe Ala Val Asn Lys Leu Gly Gly Ser Ala
                195                 200                 205
```